US006358971B1

(12) United States Patent
Ezquerra-Carrera et al.

(10) Patent No.: US 6,358,971 B1
(45) Date of Patent: Mar. 19, 2002

(54) ANTI-VIRAL COMPOUNDS

(75) Inventors: Jesus Ezquerra-Carrera, Madrid (ES); Joseph Michael Gruber, Brownsburg, IN (US); Chafiq Hamdouchi Hamdouchi, Carmel, IN (US); Richard Elmer Holmes, Indianapolis, IN (US); Wayne Alfred Spitzer, Faywood, NM (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/674,037

(22) PCT Filed: May 20, 1998

(86) PCT No.: PCT/US98/10299

§ 371 Date: Dec. 4, 2000

§ 102(e) Date: Dec. 4, 2000

(87) PCT Pub. No.: WO99/59587

PCT Pub. Date: Nov. 25, 1999

(51) Int. Cl.[7] .................. A61K 31/437; C07D 471/04; A61P 31/12

(52) U.S. Cl. ........................ 514/300; 546/121

(58) Field of Search ................... 546/121; 514/300

(56) References Cited

U.S. PATENT DOCUMENTS

| | | | |
|---|---|---|---|
| 4,008,243 A | 2/1977 | Wikel et al. ............... | 260/306 |
| 4,018,790 A | * 4/1977 | Paget .................... | 260/309.2 |
| 4,096,264 A | 6/1978 | Bochis et al. ............. | 424/256 |
| 4,118,573 A | 10/1978 | Paget et al. ............... | 548/306 |
| 4,118,742 A | 10/1978 | Paget et al. ............... | 548/306 |
| 4,174,454 A | 11/1979 | Paget et al. ............... | 548/306 |
| 4,177,274 A | 12/1979 | Bochis et al. ............. | 424/256 |
| 4,221,796 A | 9/1980 | Wade et al. ............... | 424/256 |
| 4,250,174 A | 2/1981 | Bochis et al. ............ | 424/248.5 |
| 5,840,732 A | 11/1998 | Takatani et al. ........... | 514/300 |

OTHER PUBLICATIONS

Moutou, Jean–Luc, et al., *Heterocycles*, 45:5, 897–910 (1997).

*Textbook of Human Virology*, edited by Robert B. Belshe, Chapter 16, "Rhinoviruses," Roland A. Levandowski, 391–405 (1985).

Teulade, Jean–Claude, et al., *Eur. J. Med. Chem.*, 13:3, pp. 271–276 (1978).

King, Frank D., *Medicinal Chemistry: Principles and Practice*. The Science Park, Cambridge: The Royal Society of Chemistry, Thomas Graham House, pp. 206–209 (1994).

Bochis, Richard, et al., *J. of Med. Chem.*, 21:2, pp. 235–237 (1978).

Duanmu, Chi, et al., *Cancer Research*, 49, pp. 1344–1348 (1989).

Yamanaka, Motosuke, et al., *Chem. Pharm. Bull.*, 40:3, pp. 666–674 (1992).

* cited by examiner

Primary Examiner—Evelyn Mei Huang
(74) Attorney, Agent, or Firm—Manisha A. Desai

(57) ABSTRACT

The present invention relates to compounds of Formula (I) below, which inhibit the growth of picornaviruses, Hepatitus viruses, enteroviruses, cardioviruses, polioviruses, coxsackieviruses of the A and B groups, echo virus and Mengo virus.

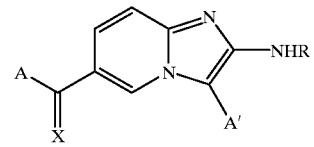

(I)

wherein:

A is phenyl, pyridyl, substituted phenyl, substituted pyridyl, or benzyl;

R is hydrogen, $COR^4$, or $COCF_3$;

X is N—OH, O, or $CHR^1$;

$R^1$ is hydrogen, halo, CN, $C_1$–$C_4$ alkyl, —C≡CH, $CO(C_1$–$C_4$ alkyl), $CO_2(C_1$–$C_4$ alkyl), or $CONR^2R^3$;

$R^2$ and $R^3$ are independently hydrogen or $C_1$–$C_4$ alkyl;

A' is hydrogen, halo, $C_1$–$C_6$ alkyl, benzyl, naphthyl, thienyl, furyl, pyridyl, pyrollyl, $COR^4$, $S(O)_nR^4$, or a group of the formula

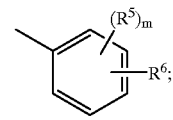

$R^4$ is $C_1$–$C_6$ alkyl, phenyl, or substituted phenyl;

n is 0, 1, or 2;

$R^5$ is independently at each occurrence hydrogen or halo;

m is 1, 2, 3, or 4; and $R^6$ is hydrogen, halo, $CF_3$, OH, $CO_2H$, $NH_2$, $NO_2$, $CONHOCH_3$, $C_1$–$C_4$ alkyl, or $CO_2(C_1$–$C_4$ alkyl), $C_1$–$C_4$ alkoxy;

or a pharmaceutically acceptable salt thereof.

8 Claims, No Drawings

ANTI-VIRAL COMPOUNDS

This application is the 371 of PCT/US98/10299, filed May 20, 1998.

FIELD OF THE INVENTION

The present invention relates to anti-viral compounds and their use in the fields of pharmaceutical and medicinal chemistry.

BACKGROUND OF THE INVENTION

The incidence of viral upper respiratory disease, the common cold, is immense. It has been estimated that nearly a billion cases annually appear in the United States alone. Rhinovirus, a member of the picornaviridae family, is the major cause of the common cold in humans. Since more than 110 strains of rhinovirus have been identified, the development of a comprehensive rhinovirus vaccine is not practical. Accordingly, chemotherapy appears to be a more desirable approach. Another member of the picornavirus family is the enterovirus, which includes approximately eighty human pathogens. Many of these enteroviruses cause cold-like symptoms; others can cause more serious diseases such as polio, conjunctivitis, aseptic meningitis and myocarditis.

Illness related to rhinovirus infection is evidenced by nasal discharge and obstruction. Furthermore, it has been implicated in otitis media, predisposes the development of bronchitis, exacerbates sinusitis, and has been implicated in the precipitation of asthmatic disease. Although it is considered by many to be a mere nuisance, its frequent occurrence in otherwise healthy individuals and the resulting economic importance has made rhinovirus infection the subject of extensive investigation.

The ability of chemical compounds to suppress the growth of viruses in vitro may be readily demonstrated using a virus plaque suppression test or a cytopathic effect test (CPE). Cf Siminoff, Applied Microbiology, 9(1), 66 (1961). Although a number of chemical compounds that inhibit picornaviruses have been identified, many are unacceptable due to 1) limited spectrum of activity, 2) undesirable side effects or 3) inability to prevent infection or illness in animals or humans. See *Textbook of Human Virology*, edited by Robert B. Belshe, chapter 16, "Rhinoviruses," Roland A. Levandowski, 391–405 (1985). Thus, despite the recognized therapeutic potential associated with a rhinovirus inhibitor and the research efforts expended thus far, a viable therapeutic agent has not yet emerged. For example, antiviral benzimidazole compounds have been disclosed in U.S. Pat. Nos. 4,008,243, 4,018,790, 4,118,573, 4,118,742 and 4,174,454.

Accordingly, the present invention provides novel pyridoimidazole compounds which inhibit the growth of picornaviruses, such as rhinoviruses (bovine and human) and the like; enteroviruses, such as polioviruses and the like; coxsackieviruses of the A and B groups, or echo virus; cardioviruses, such as encephalomyocarditis virus (EMC) and the like; apthoviruses, such as foot and mouth disease virus and the like; and Hepatitis viruses, such as Hepatitis C virus, and the like.

SUMMARY OF THE INVENTION

The present invention provides compounds of Formula (I):

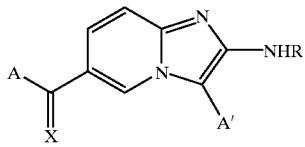

wherein:

A is phenyl, pyridyl, substituted phenyl, substituted pyridyl, or benzyl;
R is hydrogen, $COR^4$, or $COCF_3$;
X is N—OH, O, or $CHR^1$;
$R^1$ is hydrogen, halo, CN, $C_1$–$C_4$ alkyl, —C≡CH, $CO(C_1$–$C_4$ alkyl), $CO_2(C_1$–$C_4$ alkyl), or $CONR^2R^3$;
$R^2$ and $R^3$ are independently hydrogen or $C_1$–$C_4$ alkyl;
A' is hydrogen, halo, $C_1$–$C_6$ alkyl, benzyl, naphthyl, thienyl, furyl, pyridyl, pyrrolyl, $COR^4$, $S(O)_nR^4$, or a group of the formula

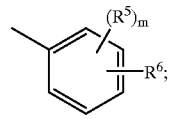

$R^4$ is $C_1$–$C_6$ alkyl, phenyl, or substituted phenyl;
n is 0, 1, or 2;
$R^5$ is independently at each occurance hydrogen or halo;
m is 1, 2, 3, or 4; and
$R^6$ is hydrogen, halo, $CF_3$, OH, $CO_2H$, $NH_2$, $NO_2$, $CONHOCH_3$, $C_1$–$C_4$ alkyl, or $CO_2(C_1$–$C_4$ alkyl), $C_1$–$C_4$ alkoxy;

or pharmaceutically acceptable salts thereof.

The present invention also provides pharmaceutical formulations comprising a compound of the present invention, or a pharmaceutically acceptable salt thereof, in combination with a pharmaceutically acceptable carrier, diluent or excipient thereof.

The present invention also provides a method for inhibiting a picornavirus comprising administering to a host in need thereof, an effective amount of a compound of Formula I, or a pharmaceutically acceptable salt thereof.

The present invention also provides a method for inhibiting a Hepatitis C virus comprising administering to a host in need thereof, an effective amount of a compound of Formula I, or a pharmaceutically acceptable salt thereof.

The present invention also provides for the use of compounds of Formula (I) for inhibiting a picornavirus, a rhinovirus, or a Hepatitis virus.

DETAILED DESCRIPTION OF THE INVENTION

The present invention relates to compounds of formula (I), as described above, that are useful as antiviral agents.

All temperatures stated herein are in degrees Celsius (° C.). All units of measurement employed herein are in weight units except for liquids which are in volume units.

The term "$C_1$–$C_6$ alkyl", as used herein, represents a straight or branched alkyl chain having from one to six carbon atoms. Typical $C_1$–$C_6$ alkyl groups include, but are not intended to be limited to; methyl, ethyl, propyl, isopropyl, butyl, isobutyl, sec-butyl, t-butyl, pentyl, neopentyl, hexyl, and the like. The term "$C_1$–$C_6$ alkyl" includes within its definition the term "$C_1$–$C_4$ alkyl", and includes within its definition cycloalkyl groups wherein the alkyl-group is formed into a ring.

The term "halo" represents chloro, fluoro, bromo, or iodo.

The term "substituted phenyl", when used herein, represents a phenyl ring substituted with 1, 2 or 3 substituents independently selected from the group consisting of; halo, $C_1$–$C_4$ alkyl, $C_1$–$C_6$ alkoxy, or trifluoromethyl.

The term "substituted pyridyl", when used herein, represents a pyridyl ring substituted with 1, 2 or 3 substituents independently selected from the group consisting of; halo, $C_1$–$C_4$ alkyl, $C_1$–$C_6$ alkoxy, or trifluoromethyl.

As mentioned above, the invention includes the pharmaceutically acceptable salts of the compounds defined by Formula (I). Although generally neutral, a compound of this invention can possess a sufficiently acidic, a sufficiently basic, or both functional groups, and accordingly react with any of a number of inorganic bases, and inorganic acids and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts include, but are not intended to be limited to, inorganic acids such as; hydrochloric acid, hydrobromic acid, hydroiodic acid, sulfuric acid, phosphoric acid, and the like; and organic acids such as; p-toluenesulfonic acid, methanesulfonic acid, oxalic acid, p-bromophenylsulfonic acid, carbonic acid, succinic acid, citric acid, benzoic acid, acetic acid, and the like.

Examples of such pharmaceutically acceptable salts include, but are not intended to be limited to; sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napthhalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include, but are not intended to be limited to, those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The pharmaceutically acceptable salts of the invention are typically formed by reacting a compound of Formula (I) with an equimolar or excess amount of acid or base. The reactants are generally combined in a neutral solvent such as diethyl ether, benzene, and the like, for acid addition salts, or water, alcohols, and the like for base addition salts. The salts normally precipitate out of solution within about one hour to about ten days, and can be isolated by filtration or other conventional methods.

The compounds of the present invention can occur in either the cis or trans configuration, wherein, cis refers to those compounds where the substituent on the alkene moiety is cis to the ring designated "A" and trans refers to those compounds where the substituent on the alkene moiety is trans to the ring designated "A". Both isomers and mixtures thereof are included within the scope of the present invention.

The following lettered paragraphs represent preferred embodiments of the present invention, however, it is to be understood that the present invention is not limited to such embodiments and that other embodiments are contemplated. Preferred compounds of Formula (I) are those wherein:

a) A is phenyl, pyridyl, substituted phenyl, or substituted pyridyl;
b) A is phenyl or substituted phenyl;
c) A is difluorophenyl or fluorophenyl;
d) A is pyridyl, substituted phenyl, or substituted pyridyl;
e) R is hydrogen
f) R is $COCF_3$;
g) X is NOH;
h) X is $CHR^1$;
i) $R^1$ is $CONR^2R^3$, $CO_2(C_1$–$C_4$ alkyl), or CN;
j) $R^1$ is $CONR^2R^3$;
k) $R^1$ is $CO_2(C_1$–$C_4$ alkyl);
l) $R^2$ and $R^3$ are independently methyl or hydrogen;
m) A' is $C_1$–$C_6$ alkyl, naphthyl, thienyl, $COR^4$, $S(O)_nR^4$, or a group of the formula

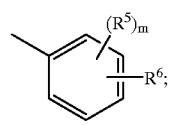

n) A' is $C_1$–$C_6$ alkyl, $COR^4$, $S(O)_nR^4$, or a group of the formula

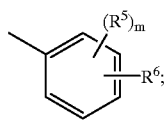

o) A' is a group of the formula

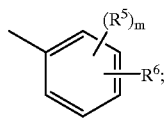

herein. The compounds of formula (I) wherein A' is; hydrogen, $C_1$–$C_6$ alkyl, napthyl, thienyl, furyl, pyridyl, pyrrolyl, or a group of the formula

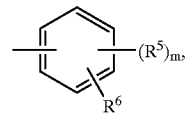

can be prepared according to Scheme I shown below.

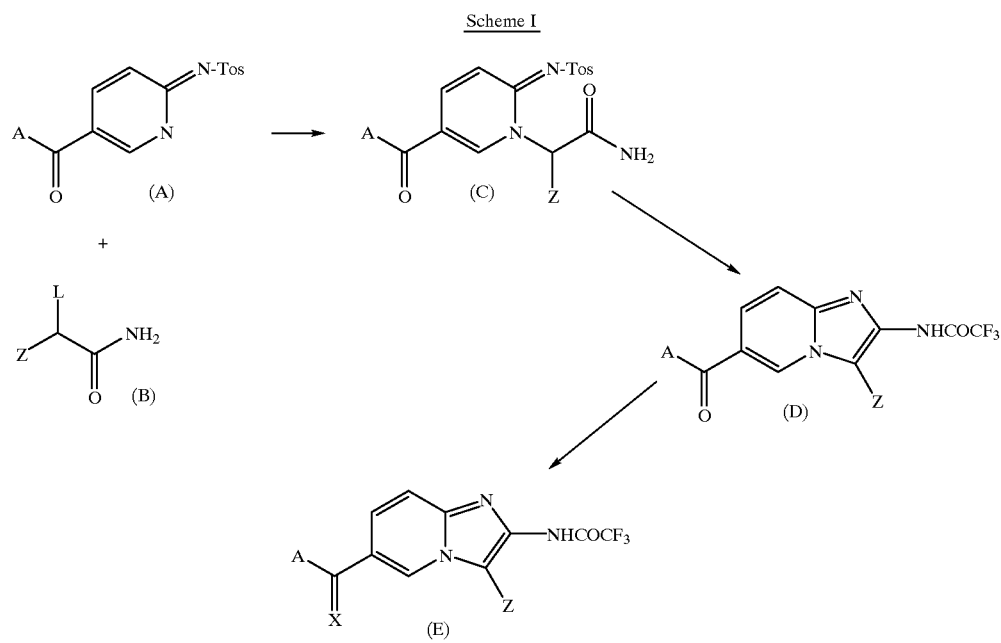

p) A' is $C_1$–$C_6$ alkyl, $COR^4$, or $S(O)_nR^4$;
q) A' is $COR^4$, or $S(O)_nR^4$;
r) $R^5$ is fluoro and m is 5;
s) m is 1, 2, 3, or 5.
t) R6 is $CF_3$, OH, $CO_2H$, $NH_2$, $NO_2$, $CONHOCH_3$, $C_1$–$C_4$ alkyl, $C_1$–$C_4$ alkoxy;
u) R6 is $CF_3$, OH, $CONHOCH_3$, $C_1$–$C_4$ alkyl, $C_1$–$C_4$ alkoxy; and
v) R6 is $CF_3$, OH, $C_1$–$C_4$ alkyl, $C_1$–$C_4$ alkoxy.

SCHEMES

The compounds of formula (I) can be prepared by synthetic methods known in the art and by methods disclosed L represents a leaving group selected from the group consisting of: halo, O-triflate, O-mesylate, O-tosylate, and the like.

Z represents hydrogen, $C_1$–$C_6$ alkyl, napthyl, thienyl, furyl, pyridyl, pyrrolyl, or a group of the formula

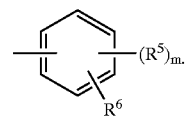

Compounds of Formula (A) can be prepared by synthetic methods known in the art and by methods disclosed herein. For example, compounds of Formula (A) can be prepared according to Scheme II shown below.

Scheme II

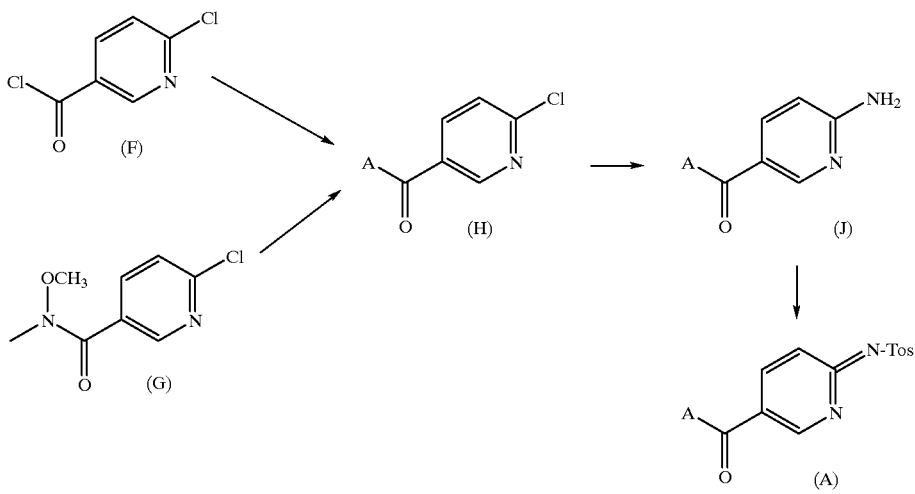

An appropriately substituted aryl group can be acylated under Friedel-Crafts conditions, in the presence of a Lewis Acid, with an appropriately substituted acid anhydride, carboxylic acid, or acid chloride to form the compounds of Formula (H). (See e.g.; *Friedel-Crafts and Related Reactions*, Ed. G. A., Olah, J. Wiley and Sons, N.Y., chapters 31,32 (1964)) Suitable Lewis acid catalysts include, but are not limited to, trifluoroacetic anhydride/phosphoric acid, trifluoromethanesulfonic acid, iron(III) chloride, zinc chloride, copper triflate (CuOTf), phosphorous oxychloride, trifluoroacetic acid, aluminum trichloride, and the like. Aluminum trichloride is the preferred Lewis acid. Suitable solvents include, but are not limited to, methylene chloride, acetonitrile, 1,2-dichloroethane, nitromethane, lower alcohols, acetonitrile, dimethylsulfoxide, and the like. The reaction is preferably run "neat" using the substituted aryl group as the preferred solvent. The substituted aryl group is generally employed in a substantial molar excess. For example, an approximately 3 to 10 molar excess, relative to the 6-chloronicotinoylchloride, is generally employed. A molar excess of about 3.8 is typically preferred. The reaction is preferably carried out at about 80° C.

Alternatively, compounds of formula (H) can be prepared by reacting a compound of formula (G) with an aryl anion by methods well known in the art. The Weinreb amide of formula (G) can be prepared from the corresponding 1-chloro-5-nicotinic acid by methods well known in the art. Likewise, the acyl anions utilized to prepare the compounds of formula (H) are well known in the art and can be prepared by methods described in the art. For example, an appropriately substituted bromo or iodo aryl group can be subjected to metal-halogen exchange conditions to afford the metal aryl anion by methods well known in the art and disclosed herein. See *Organic Reactions*, vol. 6, pg. 339, (1951) for a general discussion of metal-halogen exchange conditions. Suitable solvents include, but are not limited to, toluene, dimethylformamide, methylene chloride, diethyl ether, acetonitrile, tetrahydrofuran, and the like. Tetrahydrofuran is the preferred solvent. Suitable sources of metal include, but are not limited to, molecular lithium, alkyl lithiums, and the like including especially t-butyl lithium. N-Butyl lithium is a preferred source of metal. The metal is generally employed in a slight molar excess. For example, approximately a 1 to 1.1 molar excess is generally employed. A 1.03 molar excess is typically preferred. The reaction is preferably carried out at about −78° C. for approximately 15 minutes.

Compounds of formula (H) can be aminated with ammonia under high pressures to yield compounds of formula (J). A compound of Formula (H) is dissolved in a suitable solvent, liquid ammonia added, and the reaction sealed in a vessel resistant to elevated pressures. Suitable solvents include, but are not limited to, toluene, lower alcohols, acetontrile, ethyl ether, tetrahydrofuran, dimethylformamide, chloroform, methylenechloride, and the like. Ethanol is the preferred solvent. The reaction is preferably carried out at about 145° C. for approximately 16 hours.

The compounds of formula (A) can be prepared by procedures well known in the art. For example, a compound of formula (J) can be tosylated in an inert solvent by addition of a base and tosyl chloride. Suitable solvents include, but are not limited to, tetrahydrofuran, lower alcohols, ethyl acetate, methylene chloride, acetonitrile, chloroform, and the like. Suitable bases include triethylamine, sodium bicarbonate, sodium hydroxide, imidazole, and the like. Pyridine is the preferred base and solvent. The tosyl chloride is generally employed in a slight molar excess. For example, approximately a 1 to 2 molar excess, relative to the compound of formula (J), is generally employed. A 1.1 molar excess is typically preferred. The reaction is preferably carried out at about 90° C. for approximately 16 hours.

Compounds of formula (B) can be prepared by synthetic methods known in the art and by methods disclosed herein. For example, compounds of formula (B), wherein L is bromide, can be prepared according to Scheme III shown below.

Scheme III

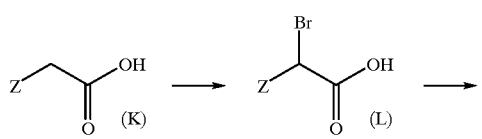

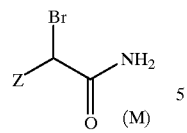

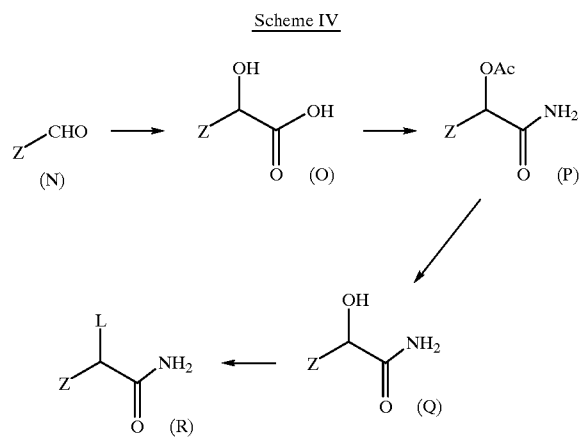

An appropriately substituted acetic acid of formula (K) is brominated in an appropriate solvent in the presence of a radical initiator to afford compounds of formula (L). Suitable brominating agents include, but are not limited to, molecular bromine, N-Bromosuccinimide, and the like. N-Bromosuccinimide is the preferred brominating agent. Suitable solvents include, but are not limited to, diethyl ether, tetrahydrofuran, methylene chloride, chloroform, acetonitrile, benzene, dimethylsulfoxide, carbon tetrachloride, and the like. Carbon tetrachloride is the preferred solvent. Suitable radical initiators include, but are not limited to, phosphorous trichloride, molecular phosphorous, benzoylperoxide, UV radiation, and the like. Preferred initators are benzoylperoxide and UV radiation. The brominating reagent is generally employed in a stoichiometric amount. For example, 1 equivalent, relative to the compound of formula (K), is generally employed and is typically preferred. The initiator is generally employed in a catalytic amount. For example, an approximately 0.1 to 1 mole percent, relative to the compound of formula (K), is generally employed. A 0.4 mole percentage is typically preferred. The reaction is preferably carried out at about 77° C. for approximately 5 hours.

Compounds of formula (M) can be prepared by amidation of compounds of formula (L) by procedures known in the art. For example, the transformation can be carried out by dissolving or suspending the compound of formula (L) in an appropriate solvent and then adding a nucleophilic source of chlorine to afford the corresponding acid chlorides, which can then be amidated in situ with gaseous ammonia. Suitable solvents include, but are not limited to, alkanes, dimethylformamide, lower alcohols, ethyl acetate, methylene chloride, tetrahydrofuran, diethyl ether, acetonitrile, chloroform, and the like. Dimethylformamide, methylene chloride, hexanes and toluene are the preferred solvents. Suitable chlorinating agents include, but are not limited to, thionyl chloride, phosphorous pentachloride, bis (trichloromethyl)carbonate, allyl chloroformate, phosphorous trichloride, triphosgene, oxalyl chloride, and the like. Oxalyl chloride is the preferred chlorinating agent. The chlorinating agent is generally employed in a slight molar excess. For example, approximately a 1 to 2 molar excess, relative to the compound of formula (L), is generally employed. A 1.6 molar excess is typically preferred. The ammonia is generally employed in a substantial molar excess. For example, ammonia gas is preferably bubbled through the reaction mixture for approximately one hour delivering an unspecified amount of ammonia. The reaction is preferably carried out at about 0° C. when adding the chlorinating agent and then for approximately 3 hours at about 22° C. before adding the gaseous ammonia over approximately 1 hour at about 22° C.

Additionally, compounds of Formula (B), wherein L is O-tosylate, can be prepared according to Scheme IV shown below.

The compounds of formula (O) can be prepared from appropriately substituted aldehydes by methods known in the art. For example, a compound of formula (N) is mixed with the acyl anion equivalent of a carboxylate, such as trimethylsilylcyanide, to afford, upon hydrolysis, the compounds of formula (O). Suitable solvents include, but are not limited to, lower alcohols, ethyl acetate, methylene chloride, acetonitrile, chloroform, and the like. The reaction is preferably run "neat" when either the aldehyde or acyl anion equivalent is a liquid. The acyl anion equivalent is generally employed in a stoichiometric ratio. For example, 1 equivalent of acyl anion, relative to the benzaldehyde, is generally employed and is typically preferred. The reaction is preferably carried out at about 25° C. for approximately 72 hours after addition of the acylanion equivalent and then at about 100° C. for approximately 18 hours to yield compounds of formula (O).

The compounds of Formula (P) can be prepared from compounds of Formula (O) by methods well known in the art. Acetylation of hydroxyacids is described throughout the art. For example, see Greene T. W., Protective Groups in Organic Synthesis, John Wiley & Sons (1981).

Compounds of formula (Q) can be prepared by amidation of compounds of Formula (P) by procedures well known in the art and disclosed herein. The amidation is substantially analogous to the method utilized to prepare compounds of formula (M) from compounds of formula (L).

The compounds of Formula (Q) can be prepared by removal of the acetyl protecting group in compounds of Formula (P) by methods well known in the art. For example, see Greene T. W., Protective Groups in Organic Synthesis, John Wiley & Sons (1981).

The compounds of Formula (R) which have an alcohol moiety converted to a leaving group are prepared by procedures well known in the art. For example, see Stang, et. al., *Synthesis*, pp. 85–1266 (1982).

Compounds of Formula (C) can be prepared by methods known in the art and by methods disclosed herein. For example, a compound of Formula (A) is combined with a compound of Formula (B) to afford the compounds of Formula (C). Suitable solvents include, but are not limited to, toluene, tetrahydrofuran, methylene chloride, diethyl ether, acetonitrile, and the like. Dimethylformamide is typically the preferred solvent. Suitable bases include, but are not limited to, cesium fluoride, cesium carbonate, hindered alkyl amines, and the like, including especially diisopropylethyl amine. Sodium hydride is typically the preferred base. The base is generally employed in a slight molar excess. For example, approximately a 1 to 1.25 molar excess, relative to the compound of Formula (A), is generally employed. A 1.1 molar excess is typically preferred. The compound of Formula (B) is generally employed in a slight molar excess. For example, approximately a 1 to 1.1 molar excess, relative to the compound of Formula (A), is generally employed. A 1.05 molar excess is typically preferred. The deprotanation is preferably carried out at room temperature for approximately 1.5 hours. After addition of the compound of Formula (B), the reaction is typically preferably carried out at room temperature for about 7 days.

Compounds of Formula (D) can be prepared by methods known in the art and by methods disclosed herein. For example, a compound of formula (C) can be cyclized by dissolving a compound of formula (C) in a suitable solvent and adding trifluoroacetic anyhdride to afford the compounds of Formula (D). Suitable solvents include, but are not limited to, toluene, dimethylformamide, tetrahydrofuran, diethyl ether, acetonitrile, and the like. Methylenechloride is typically the preferred solvent. The trifluoroacetic anhydride is generally employed in a substantial molar excess. For example, approximately a 5 to 20 molar excess, relative to the compound of Formula (C), is generally employed. A 12.4 molar excess is typically preferred. The reaction is typically preferably carried out at about the reflux temperature of methylene chloride (40° C.) for approximately 3 hours.

Compounds of Formula (E) can be prepared by methods known in the art and by methods disclosed herein.

The compounds of Formula (E), wherein X is CHR$^1$ and R$^1$ is CONH$_2$, CO(C$_1$–C$_4$ alkyl), CONR$^2$R$^3$, or CO$_2$(C$_1$–C$_4$ alkyl) can be prepared from compounds of formula (D) by procedures known in the art as well as procedures disclosed herein. For example, an appropriately substituted Horner-Emmons reagent (see *Organic Reactions*, 1977 Volume 25, pg. 73.) is deprotonated with a strong base in an aprotic solvent and a compound of Formula (D) added to afford compounds of Formula (E). Suitable strong bases include, but are not limited to, alkyl lithiums, lithium diisopropylamine, lithium bistrimethylsilylamide, and the like. Potassium t-butoxide is the preferred base. Suitable solvents include, but are not limited to, diethyl ether, tetrahydrofuran, methylene chloride, chloroform, dimethylsulfoxide, and the like. Dimethylformamide and tetrahydrofuran are the preferred solvents. The Horner-Emmons reagent is generally employed in a slight molar excess. For example, from about a 1 to 2 molar excess, relative to the compound of formula (D), is common. A 1.1 molar excess is typically preferred. The reaction is preferably carried out at about 0° C. when adding the compound of Formula (A), and then at about 25° C. for approximately 1 hour.

The compounds of Formula (E), wherein X is NOH, can be prepared from compounds of Formula (D) by procedures known in the art as well as procedures disclosed herein. For example, compounds of Formula (D) can be dissolved or suspended in an appropriate solvent and hydroxylamine added to afford the compounds of Formula (E). Suitable solvents include, but are not limited to, lower alcohols, ethyl acetate, methylene chloride, chloroform, and the like. Methanol or pyridine is the preferred solvent. The hydroxylamine is generally employed in a substantial molar excess. For example, from about a 3 to 10 molar excess, relative to the compound of Formula (E), is common. A 5.0 molar excess is typically preferred. The reaction is preferably carried out at about 25° C. for approximately 24 hours.

The compounds of Formula (E), wherein X is CHR$^1$, and R$^1$ is H, or CN; can be prepared from compounds of Formula (D) by procedures known in the art as well as procedures disclosed herein. For example, an appropriately substituted Peterson Olefination Reagent (see Organic Reactions, 1990, volume 38, pg. 1.) can be dissolved in a suitable solvent and deprotonated with a strong base. A compound of Formula (D) can then added to the product. Suitable strong bases include, but are not limited to, potassium t-butoxide, alkyl lithiums, lithium diisopropylamine, lithium bistrimethylsilylamide, and the like. N-Butyl lithium is the preferred base. Suitable solvents include, but are not limited to, diethyl ether, methylene chloride, chloroform, dimethylformamide, dimethylsulfoxide, and the like. Tetrahydrofuran is the preferred solvent. The Peterson Reagent is generally employed in a substantial molar excess. For example, from about a 3 to 10 molar excess, relative to the compound of Formula (D), is common. A 5.0 molar excess is typically preferred. The reaction is preferably carried out at about –78° C. when deprotonating the Peterson Reagent and when adding the compound of Formula (D), and then at about 25° C. for approximately 24 hours.

The compounds of Formula (E), wherein X is CHR$^1$ and R$^1$ is halo, can be prepared from compounds of Formula (E), wherein X is CH$_2$, by procedures known in the art as well as procedures disclosed herein. For example, a compound of Formula (E), wherein X is CH$_2$, can be dissolved in a suitable solvent and an appropriate halogenating agent added to form the product. Suitable solvents include, but are not limited to, methylene chloride, tetrahydrofuran, chloroform, acetonitrile, acetic acid, and the like. Tetrahydrofuran and carbon tetrachloride are the preferred solvents. Suitable halogenating agents include, but are not limited to, benzene seleninyl chloride/aluminum chloride, thionyl chloride, molecular bromine, CsSO$_4$F, NFTh, and the like. The halogenating reagent is generally employed in a slight molar excess. For example, from about a 1 to 2 molar excess, relative to the starting material. A 1.1 molar excess is typically preferred. The reaction is preferably carried out at about –10° C. when adding the halogenating agent and then at about 22° C. for approximately 1 hour.

A skilled artisan would appreciate that the ratio of cis/trans products isolated by the schemes disclosed herein can vary widely, from completely cis or trans to equally proportions of both, depending upon the starting materials employed and the reaction conditions utilized.

Compounds of formula (I) wherein A' is COR$^5$ can be prepared according procedures shown in Scheme V outlined below.

Scheme V

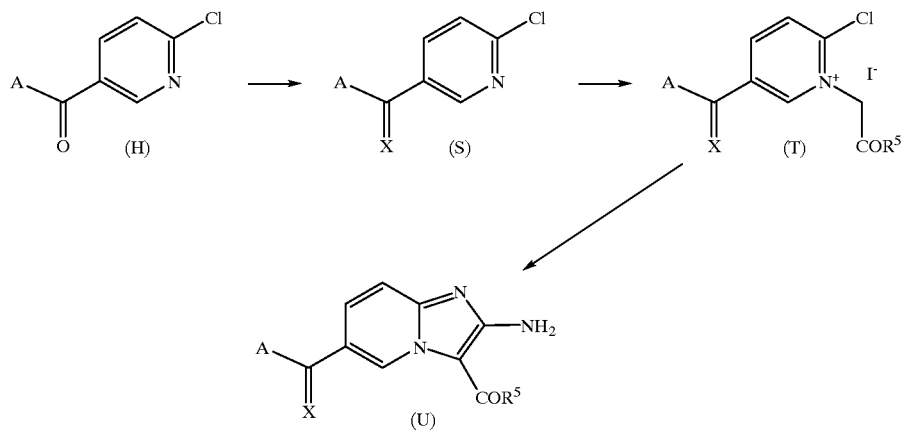

Compounds of Formula (S) can be prepared by methods known in the art and disclosed herein. For example, compounds of Formula (H) can be converted to compounds of Formula (S) in a manner substantially analogous to the conversion of compounds of Formula (D) to those of Formula (E) described herein.

Compounds of Formula (T) can be prepared by methods known in the art and disclosed herein. For example, a compound of Formula (S) and a compound of the formula $BrCH_2COR^5$ can be dissolved in an appropriate solvent in the presence of iodide anion to afford the compounds of formula (T). Suitable solvents include, but are not limited to, toluene, dimethylformamide, methylene chloride, tetrahydrofuran, diethyl ether, acetonitrile, and the like. Acetonitrile is the preferred solvent. Suitable sources of iodide anion include, but are not limited to, iodide salts such as sodium, potassium, and ammonium iodide, and the like. Sodium iodide is the preferred source of iodide anion. The compound of the formula $BrCH_2COR^5$ is generally employed in a substantial molar excess. For example, approximately a 2 to 10 molar excess, relative to the compound of Formula (S), is generally employed. A 3.7 molar excess is typically preferred. The iodide anion is generally employed in a substantial molar excess. For example, approximately 2 to 10 molar excess, relative to the compound of Formula (S), is generally employed. A 3.8 molar excess is typically preferred. The reaction is preferably carried out at about the reflux temperature of the solvent for approximately 40 hours.

Compounds of Formula (U) can be prepared by methods known in the art and disclosed herein. For example, a compound of Formula (T), aminonitrile, and a base can be combined and dissolved in an appropriate solvent to afford the compounds of formula (U). Suitable solvents include, but are not limited to, toluene, dimethylformamide, methylene chloride, tetrahydrofuran, diethyl ether, acetonitrile, and the like. Acetonitrile is the preferred solvent. Suitable bases include, but are not limited to, carbonates, hydroxides, and the like. Potassium carbonate is the preferred base. The aminonitrile is generally employed in a slight molar excess. For example, approximately a 1 to 1.05 molar excess, relative to the compound of Formula (T), is generally employed. A 1.02 molar excess is typically preferred. The base is generally employed in a substantial molar excess. For example, approximately a 2 to 5 molar excess, relative to the compound of Formula (T), is generally employed. A 3.05 molar excess is typically preferred. The reaction is typically preferably carried out at about the reflux temperature of the solvent for approximately 14 hours.

Compounds of formula (I) wherein A' is $S(O)_nR^5$ can be prepared according procedures shown in Scheme VI outlined below.

Scheme VI

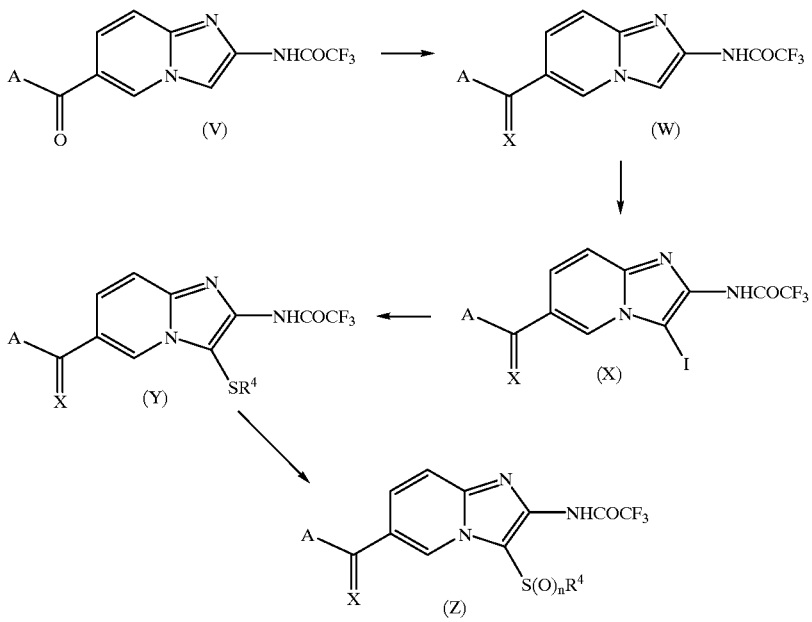

Scheme VI

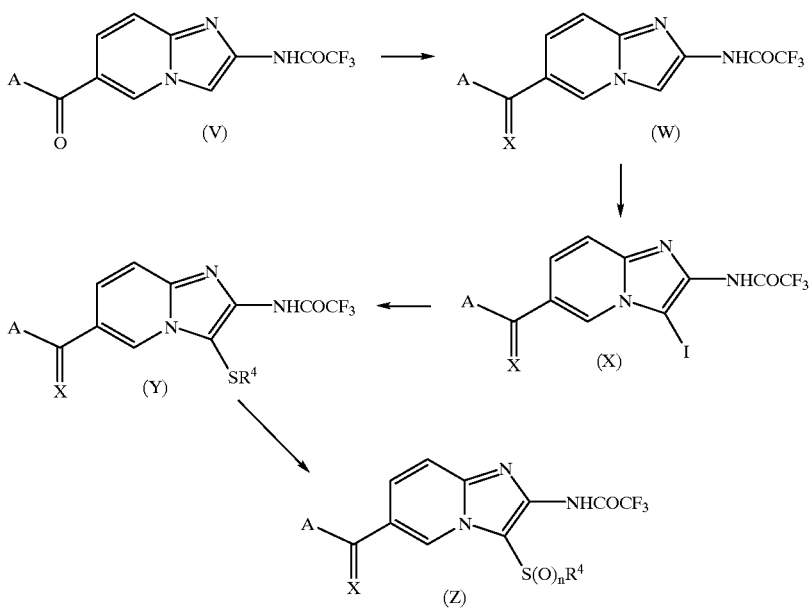

Compounds of Formula (W) can be prepared by methods known in the art and disclosed herein. For example, compounds of Formula (V) can be converted to compounds of Formula (W) in a manner substantially analogous to the conversion of compounds of Formula (D) to those of Formula (E) described previously within.

Compounds of Formula (X) can be prepared by methods known in the art and disclosed herein. For example, compounds of Formula (W) can be dissolved in a suitable solvent and an iodinating reagent added to form the compounds of Formula (X). Suitable solvents include, but are not limited to, toluene, dimethylformamide, methylene chloride, tetrahydrofuran, diethyl ether, acetonitrile, and the like. Acetonitrile is the preferred solvent. Suitable iodinating reagents include, but are not limited to, molecular iodine, N-iodosuccinimide, and the like. N-iodosuccinimide is the preferred iodinating reagent. The iodinating reagent is generally and preferably employed in a stoichiometric or equimolar amount relative to the compound of Formula (W). The reaction is preferably carried out at about 0° C. for approximately 15 minutes.

Compounds of Formula (Y) can be prepared by methods known in the art and disclosed within. For example, appropriately substituted sulfides can be reacted with an imidazopyridyl anion or anion equivalent by methods well known in the art. Suitable sulfides include but are not limited to, symetrical sulfides, unsymetrical disulfides, and thiolsulfonates. The thiol sulfonates can be prepared from the generally commercially available disulfides by methods well known in the art and taught in *J. Am. Chem. Soc.* 1977, 4405.

Compounds of Formula (Y) can be prepared from compounds of Formula (X) by methods well known in the art and methods disclosed herein. For example, a metal-halogen exchange reaction with a compound of Formula (X), substantially analogous to that described previously in the preparation of compounds of Formula (H), followed by the addition of an appropriately substituted sulfide. The skilled artisan will recognize that in contrast to the preparation of the phenyl anion, which is used to form compounds of Formula (H), where there are no acidic protons, the analogous compounds of Formula (X) have one acidic proton and therefore should be deprotonated with a base before attempting the metal-halogen exchange reaction. Suitable bases include, but are not limited to, molecular lithium, alkyl lithiums, lithium amines such as lithium diisopropyl amine, lithium hydride and the like. Phenyl lithium is the preferred base. T-Butyl lithium is the preferred metal source. Suitable solvents include, but are not limited to, toluene, dimethylformamide, methylene chloride, acetonitrile, diethyl ether, tetrahydrofuran, and the like. Tetrahydrofuran is the preferred solvent. The base is generally employed in a slight to substantial molar excess. For example, approximately 1.5 to 3 molar excess relative to the compound of Formula (X) is generally employed. A 2.2 molar excess is typically preferred. The metal is generally employed in a slight to substantial molar excess. For example, approximately 1.5 to 3 molar excess relative to the compound of Formula (X) is generally employed. A 2.5 molar excess is typically preferred. The reaction is preferably carried out at about −78° C. for approximately 3 minutes after the addition of the base, for approximately 10 minutes after the addition of the metal source, and for approximately 30 minutes after addition of the sulfide.

Alternatively, compounds of Formula (Y), can be prepared from an imidazopyridyl anion equivalent, prepared from compounds of Formula (X) under Ullmann like coupling conditions. See *Synthesis*, 9–21, (1974) for a review of the Ullmann reaction. For example, a compound of the Formula (X) can be dissolved in a suitable solvent, a copper source is added, followed by an appropriately substituted sulfide. Suitable solvents include, but are not limited to, toluene, dimethylformamide, methylene chloride, acetonitrile, diethyl ether, tetrahydrofuran, pyridine, and the like. Pyridine is the preferred solvent. Suitable sources of copper include, but are not limited to, molecular copper, copper(I)oxide, and the like. Copper bronze or powdered copper is the preferred source. The copper is generally employed in a slight to substantial molar excess. For example, approximately 1.2 to 3 molar excess relative to the compound of Formula (X) is generally employed. A 1.5 molar excess is typically preferred. The sulfide is generally employed in a slight molar deficiency. For example, approximately a 50 to 95 molar percent, relative to the compound of Formula (X), is generally employed. A 78 molar percent is typically preferred. The reaction is preferably carried out at about 100° C. for approximately 80 hours.

As another alternative, compounds of formula (Y) can be prepared from compounds of formula (X) by the use of a palladium catalyzed cross coupling reaction between a compound of the Formula (X) and an appropriately substituted trimethyl-thio-tin, i.e. $R^4S-Sn(Alkyl)_3$. See for example *Synth.Commun*, 22, (5), p. 683, (1992).

Compounds of Formula (Z) can be prepared by oxidation of compounds of Formula (Y) by procedures well known in the art and disclosed herein. For a general review of the oxidation of sulfides to sulfones, see *Comprehenive Organic Synthesis,* Volume 7, Ch. 6.2, pg. 762, Pergamon Press, Inc. New York, (1991).

The skilled artisan will recognize that it may become advantageous, although not necessary, to remove the trifluoroacetyl protecting group, found in the above schemes, at various points in the syntheses of the compounds of the present invention. The removal of this protecting group can be accomplished by methods well known in the art and disclosed herein. For example, the trifluoroacetylgroup can be removed by dissolving compounds of Formula (D), (E), (V), (W), (X), (Y), or (Z) in an appropriate solvent then adding a base to afford the corresponding deprotected products. Appropriate bases include, but are not limited to, hydroxides, carbonates, amines, and the like. The preferred base is diisopropylethylamine. Alternatively, the protecting group can be hydrolyzed on a silica gel support. See also Greene T. W., Protective Groups in Organic Synthesis, John Wiley & Sons (1981).

In general, the reactions of Schemes I–VI are substantially complete in about 15 minutes to 72 hours when conducted at a temperature range of from about −78° C. to the reflux temperature of the reaction mixture. A skilled artisan would appreciate that the rate of a reaction generally increases with an increase in temperature. It is often advantageous, although not necessary, however, to conduct reactions at a slower rate to better control the number and quantity of side products generated. The choice of reaction solvent is not critical so long as the solvent employed is inert to the ongoing reaction and the reactants are sufficiently solubilized to effect the desired reaction. Once a reaction is complete, the intermediate compound may be isolated, if desired, by procedures known in the art. For example, the compound may be crystallized and then collected by filtration, or the reaction solvent may be removed by extraction, evaporation, or decantation. The intermediate may be further purified, if desired by common techniques such as recrystallization or chromatography over solid supports such as silica gel or alumina. The compounds of Formula A–Z are preferably isolated before use in subsequent reactions.

PREPARATIONS AND EXAMPLES

The following Preparations and Examples further illustrate specific aspects of the present invention. It is to be understood, however, that these examples are included for illustrative purposes only and are not intended to limit the scope of the invention in any respect and should not be so construed.

The compounds employed as initial starting materials in the synthesis of the compounds of this invention are known in the art, and, to the extent not commercially available are readily synthesized by standard procedures commonly employed in the art.

It will be understood by those skilled in the art that in performing the processes described above it may be desirable to introduce chemical protecting groups into the reactants in order to prevent secondary reactions from taking place. For example, any amine, alcohol, alkylamine or carboxy groups which may be present on the reactants may be protected using any standard protecting group which does not adversely affect the remainder of the molecule's ability to react in the manner desired. The various protective groups may then be removed simultaneously or successively using methods known in the art.

The cis and trans forms of the compounds of the present invention can be separated using column chromatography, for example reverse phase HPLC. The compounds may be eluted from the column using an appropriate ratio of acetonitrile and water or methanol and water.

In the following Preparations and Examples, the terms melting point, nuclear magnetic resonance spectra, electron impact mass spectra, field desorption mass spectra, fast atom bombardment mass spectra, high resolution mass spectra, infrared spectra, ultraviolet spectra, elemental analysis, high performance liquid chromatography, thin layer chromatography, nitrogen, water, ethyl acetate, ethyl ether, dichloromethane, dimethylformamide, chloroform, methanol, ethanol, acetonitrile, tetrahydrofuran, sodium hydroxide, potassium hydroxide, sodium bicarbonate, sulfuric acid, hydrobromic acid, hydrochloric acid, ammonium hydroxide, sodium sulfite, sodium hydrosulfite, sodium nitrite, sodium sulfate, saturated sodium chloride, sodium bromide, ammonium chloride, magnesium sulfate, sodium acetate, and room temperature are abbreviated "m.p.", "NMR", "EIMS", "MS(FD)", "MS(FAB)", "MS(HR), "IR", "UV", "Analysis", "HPLC", and "TLC", "$N_2$", "$H_2O$", "EtOAc", "$E_2O$", "$CH_2Cl_2$", "DMF", "$CHCL_3$", "MeOH", "EtOH", "$CH_3CN$", "THF", "NaOH", "KOH", "$NaHCO_3$", "$H_2SO_4$", "HBr", "HCl", "$NH_4OH$", "$Na_2SO_3$", "$NaHSO_3$", "$NaNO_2$", "$Na_2SO_4$", "brine", "NaBr", "$NH_4Cl$", "$MgSO_4$", "NaOAc", and "RT" respectively. The values reported for MS(FD) correspond to mass numbers unless otherwise indicated. In addition, the absorption maxima listed for the IR spectra are only those of interest and not all of the maxima observed.

The NMR spectra were obtained on a Brüker Corp. 270 MHz instrument or on a General Electric QE-300 300 MHz instrument. The chemical shifts are expressed in delta (δ) values (parts per million downfield from tetramethyl-silane). The MS(FD) spectra were taken on a Varian-MAT 731 Spectrometer using carbon dendrite emitters. EIMS spectra were obtained on a CEC 21-110 instrument from Consolidated Electrodynamics Corporation. IR spectra were obtained on a Perkin-Elmer 281 instrument. UV spectra were obtained on a Cary 118 instrument. TLC was carried out on E. Merck silica gel plates. Melting points are uncorrected.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

When used within the preparations, the terms "MS", "Analysis", "IR", "UV", and "NMR" indicate that the corresponding mass spectrum, elemental analysis, infrared spectrum, ultraviolet spectrum, and nuclear magnetic resonance spectrum were consistent with the desired product.

Preparation 1

2-Chloro-5-benzoylpyridine

Aluminum chloride (100 g, 0.730 mol) was suspended in 200 ml benzene under $N_2$. A solution of 6-chloronicotinoyl chloride (53 g, 0.30 mol) in 100 ml benzene was added to the rapidly stirring suspension then refluxed overnight. The reaction was cooled to RT, 1 L EtOAc was added, and the pH was adjusted to 8.5 with 5N NaOH. Aluminum salts precipitated and were filtered away. The filtrate was washed with $H_2O$, dried over $Na_2SO_4$, and concentrated in vacuo.

The resulting tan solid was recrystallized from 3:2 $Et_2O$:hexanes yielding 54.6 g (83%) of product as tan crystals. EA, MS(FD).

Preparation 2

2-Chloro-5-(4-fluorobenzoyl)pyridine

The fluorobenzene (150 ml, 1.60 mmol) and 6-chloronicotinoyl chloride (17.7 g, 100 mmol) were converted to product in a manner substantially analogous to Preparation 1 to yield 15.2 g. (66.1%). EA, MS(FD), NMR.

Preparation 3

2-amino-5-benzoylpyridine

The 2-chloro-5-benzoylpyridine (100 g, 0.460 mol) was dissolved in 500 ml of 3A EtOH and 400 ml of anhydrous ammonia, placed in a bomb, then heated at 145° C. for 16 hours. The solvents were removed in vacuo and the remaining tan solid was recrystallized from EtOH/$H_2O$ yielding 77.4 g (85%) of product as a tan solid. EA, MS(FD).

Preparation 4

2-amino-5-(4-fluorobenzoyl)pyridine

The 2-chloro-5-(4-fluorobenzoyl)pyridine (59.1 g, 251 mmol) was converted to product in a manner substantially analogous to Preparation 3 to yield 35.4 g. (65.3%). EA, MS(FD).

Preparation 5

1,2-Dihydro-2-toluenesulfonimido-5-benzoylpyridine

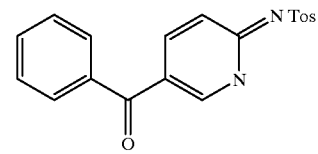

The 2-amino-5-benzoylpyridine (77.44 g, 0.390 mol) and p-toluenesulfonyl chloride (82.03 g, 0.43 mol) were combined in 300 ml of pyridine and heated to 90° C. under $N_2$ for 16 hours. The pyridine was removed in vacuo and the solids stirred in 1.5 L of $H_2O$ for 1 hour. The solids were filtered away and recrystallized from EtOAc yielding 118.7 g (86%) of product as off-white crystals. EA, MS(FD).

Preparation 6

1,2-Dihydro-2-toluenesulfonimido-5-(4-fluorobenzoyl)pyridine

The 2-amino-5-(4-fluorobenzoyl)pyridine (35.0 g, 162 mmol) was converted to product in a manner substantially analogous to Preparation 5 to yield 47.7 g. (79.6%). MS(FD), NMR.

Preparation 7

α-Bromo-(4-fluorophenyl)acetic acid

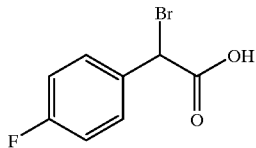

The 4-fluorophenylacetic acid (20 g, 0.13 mol), benzoyl peroxide (130 mg, 0.540 mmol), and N-bromosuccinimide (23.1 g, 0.130 mol) were combined in 500 ml carbon tetrachloride under $N_2$ and refluxed under UV irradiation (GE sunlamp) for 5 hours. The reaction was cooled to RT and the succinimide filtered away. The carbon tetrachloride was removed in vacuo and the remaining oil recrystallized from hexanes yielding 26.2 g (87%) of product as a light yellow solid. EA, MS(FD).

Preparation 8

α-Bromo-(4-methoxyphenyl)acetic acid

The 4-methoxyphenylacetic acid (25.0 g, 150 mmol) was converted to product in a manner substantially analogous to Preparation 7 to yield 36.6 g. (100%). MS(FD), NMR.

Preparation 9

α-Bromo-(napth-2-yl)acetic acid

The (napth-2-yl)acetic acid (37.2 g, 200 mmol) was converted to product in a manner substantially analogous to Preparation 7 to yield 34.5 g. (65%). MS(FD), NMR.

Preparation 10

α-Bromo-napthylacetic acid

The napthylacetic acid (37.2 g, 200 mmol) was converted to product in a manner substantially analogous to Preparation 7 to yield 32.4 g. (60.8%). MS(FD), NMR.

Preparation 11

α-Bromo-(2-fluorophenyl)acetic acid

The (2-fluorophenyl)acetic acid (19.9 g, 129 mmol) was converted to product in a manner substantially analogous to Preparation 7 to yield 24.0 g. (79.9%).

Preparation 12

α-Bromo-(3-fluorophenyl)acetic acid

The (3-fluorophenyl)acetic acid (20.0 g, 130 mmol) was converted to product in a manner substantially analogous to Preparation 7 to yield 24.3 g. (80.0%).

Preparation 13

α-Bromo-(2,4-difluorophenyl)acetic acid

The 2,4-difluorophenylacetic acid (21.3 g, 124 mmol) was converted to product in a manner substantially analogous to Preparation 7 to yield 24.8 g. (79.5%). NMR.

Preparation 14

α-Bromo-(3,5-difluorophenyl)acetic acid

The (3,5-difluorophenyl)acetic acid (20.4 g, 118 mmol) was converted to product in a manner substantially analogous to Preparation 7 to yield 21.0 g. (70.9%). NMR.

Preparation 15

α-Bromo-(2,5-difluorophenyl)acetic acid

The (2,5-difluorophenyl)acetic acid (20.5 g, 119 mmol) was converted to product in a manner substantially analogous to Preparation 7 to yield 27.3 g. (91.0%).

Preparation 16

α-Bromo-(3-trifluoromethylphenyl)acetic acid

The (3-trifluoromethylphenyl)acetic acid (20 g, 90 mmol) was converted to product in a manner substantially analogous to Preparation 7 to yield 27.7 g. (100%). NMR.

Preparation 17

α-Bromo-(4-bromophenyl)acetic acid

The (4-bromophenyl)acetic acid (25.8 g, 120 mmol) was converted to product in a manner substantially analogous to Preparation 7 to yield 30.2 g. (85.7%). NMR.

Preparation 18

α-Bromo-(2,3,4-trifluorophenyl)acetic acid

The (2,3,4-trifluorophenyl)acetic acid (9.55 g, 50.3 mmol) was converted to product in a manner substantially analogous to Preparation 7 to yield 13.5 g. (100%). NMR.

Preparation 19

α-Bromo-(3,4-difluorophenyl)acetic acid

The (3,4-difluorophenyl)acetic acid (15.2 g, 88.2 mmol) was converted to product in a manner substantially analogous to Preparation 7 to yield 22.2 g. (100%). NMR.

Preparation 20

α-Bromo-(3,4-dichlorophenyl)acetic acid

The (3,4-dichlorophenyl)acetic acid (25.0 g, 122 mmol) was converted to product in a manner substantially analogous to Preparation 7 to yield 34.6 g. (100%).

Preparation 21

α-Bromo-(2,4,5-trifluorophenyl)acetic acid

The (2,4,5-trifluorophenyl)acetic acid (9.56 g, 50.3 mmol) was converted to product in a manner substantially analogous to Preparation 7 to yield 13.6 g. (100%). NMR.

Preparation 22

α-Bromo-(2-chlorophenyl)acetic acid

The (2-chlorophenyl)acetic acid (25.3 g, 148 mmol) was converted to product in a manner substantially analogous to Preparation 7 to yield 22.8 g. (62.0%). MS(FD), NMR.

Preparation 23

α-Bromo-(3-chlorophenyl)acetic acid

The (3-chlorophenyl)acetic acid (20.9 g, 123 mmol) was converted to product in a manner substantially analogous to Preparation 7 to yield 30.5 g. (100%). NMR.

Preparation 24

α-Bromo-(4-chlorophenyl)acetic acid

The (4-chlorophenyl)acetic acid (25.0 g, 147 mmol) was converted to product in a manner substantially analogous to Preparation 7 to yield 21.7 g. (60.0%). NMR.

Preparation 25

α-Bromo-(4-trifluoromethoxyphenyl)acetic acid

The (4-trifluoromethoxyphenyl)acetic acid (9.91 g, 45.1 mmol) was converted to product in a manner substantially analogous to Preparation 7 to yield 13.5 g. (100%). NMR.

Preparation 26

α-Bromo-(3-trifluoromethoxyphenyl)acetic acid

The (3-trifluoromethoxyphenyl)acetic acid (9.75 g, 44.3 mmol) was converted to product in a manner substantially analogous to Preparation 7 to yield 13.3 g. (100%). NMR.

Preparation 27

α-Bromo-(2-fluoro-4-trifluoromethylphenyl)acetic acid

The (2-fluoro-4-trifluoromethylphenyl)acetic acid (9.56 g, 43.1 mmol) was converted to product in a manner substantially analogous to Preparation 7 to yield 13.0 g. (100%). NMR.

Preparation 28

α-Bromo-(2-methoxyphenyl)acetic acid

The (2-methoxyphenyl)acetic acid (25.0 g, 150 mmol) was converted to product in a manner substantially analogous to Preparation 7 to yield 26.5 g. (72%). MS(FD), NMR.

Preparation 29

α-Bromo-(4-nitrophenyl)acetic acid

The (4-nitrophenyl)acetic acid (25.5 g, 141 mmol) was converted to product in a manner substantially analogous to Preparation 7 to yield 36.6 g. (100%). NMR.

Preparation 30

α-Bromo-(3-thienyl)acetic acid

The (thiophen-3-yl)mandelic acid (8.60 g, 54.4 mmol) was dissolved in 100 ml of 30% HBr in acetic acid. The solution was stirred for 18 hours at RT. The clear black solution was poured onto 2.5 L of ice water and immediately extracted with Et$_2$O (4×400 ml). The ether was dried over Na$_2$SO$_4$ and treated with decolorizing carbon. The Et$_2$O was evaporated and the residue was azeotroped with toluene to remove residual acetic acid. The crude solid product was recrystalized from hexanes to yield 9.07 g. (75.%). EA, MS(FD).

Preparation 31

α-Bromo-benzylacetic acid

To a solution of L-phenylalanine (55.0 g, 330 mmol) and NaBr (130 g, 1.09 mol) dissolved in 550 ml of 3N H$_2$SO$_4$ cooled to 0° C., was added slowly NaNO$_2$ (32.0 g, 469 mmol) keeping the temperature of the reaction between 0 and 5° C. The stirring was continued at about 0° C. for 1 hour and then for 1.5 hours at RT. The mixture was extracted with Et$_2$O (4×300 ml). The Et$_2$O was washed with brine (2×500 ml), dried over MgSO$_4$, and then removed in vacuo. The residue was recrystalized from 50 ml of cyclohexane to give the phenylalanine starting material as crystals. The solids were filtered and the filtrate was concentrated in vacuo to yield 64 g of crude product to be used without further purification. (84.7%).

Preparation 32

α-Bromo-(4-fluorophenyl)acetamide

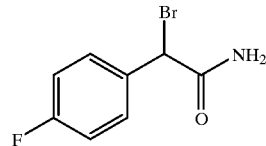

The α-bromo-(4-fluorophenyl)acetic acid (26.1 g, 112 mmol), in 175 ml of dry CH$_2$Cl$_2$, and 3 drops of DMF were cooled in an ice bath under N$_2$. Oxalyl chloride (25.0 g, 224 mmol) in 25 ml of dry CH$_2$Cl$_2$ was added dropwise over 25 minutes. The ice bath was removed and the reaction stirred for 3 hours. The solvent was removed in vacuo then azeotroped with toluene (3×25 ml). The remaining oil was dissolved in 300 ml of toluene and 300 ml hexanes and stirred vigorously with a mechanical stirrer. Ammonia gas was then blown through a gas dispersion tube over the top of this solution for 1 hour. The resulting solid was filtered and the solvents removed in vacuo. The solid was dissolved in EtOAc/H$_2$O and the organic layer washed with 1N HCl, saturated NaHCO$_3$, brine, then dried over Na$_2$SO$_4$. The Na$_2$SO$_4$ was filtered and the EtOAc was removed in vacuo. The remaining solid was recrystallized from EtOAc/hexanes yielding 19.6 g (75%) of the desired product. MS(FD), NMR.

Preparation 33

α-Bromo-(4-methoxyphenyl)acetamide

The α-bromo-(4-methoxyphenyl)acetic acid (36.6 g, 150 mmol) was converted to product in a manner substantially analogous to Preparation 32 to yield 13.5 g. (37%). MS(FD), NMR.

Preparation 34

α-Bromo-(napth-2-yl)phenylacetamide

The α-bromo-(napth-2-yl)acetic acid (34.5 g, 130 mmol) was converted to product in a manner substantially analogous to Preparation 32 to yield 11.5 g. (33.5%). EA, MS(FD).

Preparation 35

α-Bromo-napthylacetamide

The α-bromo-napthylacetic acid (32.4 g, 122 mmol) was converted to product in a manner substantially analogous to Preparation 32 to yield 14.6 g. (46%). MS(FD), NMR.

Preparation 36

α-Bromo-(2-fluorophenyl)acetamide

The α-bromo-(2-fluorophenyl)acetic acid (24.0 g, 103 mmol) was converted to product in a manner substantially analogous to Preparation 32 to yield 14.0 g. (60%). MS(FD), NMR.

Preparation 37

α-Bromo-(3-fluorophenyl)acetamide

The α-bromo-(3-fluorophenyl)acetic acid (24.3 g, 104 mmol) was converted to product in a manner substantially

Preparation 38

α-Bromo-(2,4-difluorophenyl)acetamide

The α-bromo-(2,4-difluorophenyl)acetic acid (23.3 g, 93.0 mmol) was converted to product in a manner substantially analogous to Preparation 32 to yield 7.88 g. (34.3%). NMR.

Preparation 39

α-Bromo-(3,5-difluorophenyl)acetamide

The α-bromo-(3,5-difluorophenyl)acetic acid (21.0 g, 83.8 mmol) was converted to product in a manner substantially analogous to Preparation 32 to yield 14.4 g. (68.7%). NMR.

Preparation 40

α-Bromo-(2,5-difluorophenyl)acetamide

The α-bromo-(2,5-difluorophenyl)acetic acid (27.3 g, 109 mmol) was converted to product in a manner substantially analogous to Preparation 32 to yield 18.5 g. (68.0%). MS(FD), NMR.

Preparation 41

α-Bromo-(3-trifluoromethylphenyl)acetamide

The α-bromo-(3-trifluoromethylphenyl)acetic acid (27.7 g, 98.0 mmol) was converted to product in a manner substantially analogous to Preparation 32 to yield 14.2 g. (51.4%). MS(FD), NMR.

Preparation 42

α-Bromo-(4-bromophenyl)acetamide

The α-bromo-(4-bromophenyl)acetic acid (30.2 g, 103 mmol) was converted to product in a manner substantially analogous to Preparation 32 to yield 23.5 g. (78.1%). MS(FD), NMR.

Preparation 43

α-Bromo-(2,3,4-trifluorophenyl)acetamide

The α-bromo-(2,3,4-trifluorophenyl)acetic acid (13.5 g, 50.3 mmol) was converted to product in a manner substantially analogous to Preparation 32 to yield 10.2 g. (75.7%). MS(FD), NMR.

Preparation 44

α-Bromo-(3,4-difluorophenyl)acetamide

The α-bromo-(3,4-difluorophenyl)acetic acid (22.2 g, 88.0 mmol) was converted to product in a manner substantially analogous to Preparation 32 to yield 7.88 g. (35.7%). MS(FD), NMR.

Preparation 45

α-Bromo-(3,4-dichlorophenyl)acetamide

The α-bromo-(3,4-dichlorophenyl)acetic acid (34.6 g, 122 mmol) was converted to product in a manner substantially analogous to Preparation 32 to yield 11.8 g. (34.2%). MS(FD), NMR.

Preparation 46

α-Bromo-(2,4,5-trifluorophenyl)acetamide

The α-bromo-(2,4,5-trifluorophenyl)acetic acid (13.6 g, 50.3 mmol) was converted to product in a manner substantially analogous to Preparation 32 to yield 7.34 g. (54.4%). NMR.

Preparation 47

α-Bromo-(2-chlorophenyl)acetamide

The α-bromo-(2-chlorophenyl)acetic acid (22.8 g, 91.7 mmol) was converted to product in a manner substantially analogous to Preparation 32 to yield 17.5 g. (77%). MS(FD), NMR.

Preparation 48

α-Bromo-(3-chlorophenyl)acetamide

The α-bromo-(2-chlorophenyl)acetic acid (30.5 g, 123 mmol) was converted to product in a manner substantially analogous to Preparation 32 to yield 17.8 g. (59%). MS(FD), NMR.

Preparation 49

α-Bromo-(4-chlorophenyl)acetamide

The α-bromo-(4-chlorophenyl)acetic acid (21.7 g, 86.9 mmol) was converted to product in a manner substantially analogous to Preparation 32 to yield 15.7 g. (73%). MS(FD), NMR.

Preparation 50

α-Bromo-(4-trifluoromethoxyphenyl)acetamide

The α-bromo-(4-trifluoromethoxyphenyl)acetic acid (13.5 g, 45.1 mmol) was converted to product in a manner substantially analogous to Preparation 32 to yield 11.1 g. (83%). MS(FD), NMR.

Preparation 51

α-Bromo-(3-trifluoromethoxyphenyl)acetamide

The α-bromo-(3-trifluoromethoxyphenyl)acetic acid (13.3 g, 44.3 mmol) was converted to product in a manner substantially analogous to Preparation 32 to yield 9.43 g. (71%). MS(FD), NMR.

Preparation 52

α-Bromo-(2-fluoro-4-trifluoromethylphenyl) acetamide

The α-bromo-(2-fluoro-4-trifluoromethylphenyl)acetic acid (13.0 g, 43.1 mmol) was converted to product in a manner substantially analogous to Preparation 32 to yield 11.1 g. (86%). MS(FD), NMR.

Preparation 53

α-Bromo-phenylacetamide

The α-bromo-phenylacetic acid (21.5 g, 100 mmol) was converted to product in a manner substantially analogous to Preparation 32 to yield 16.8 g. (78%). NMR.

Preparation 54

α-Bromo-(thiophen-3-yl)acetamide

The α-bromo(thiophen-3-yl)acetic acid (9.07 g, 41.0 mmol) was converted to product in a manner substantially analogous to Preparation 32 to yield 6.50 g. (72.0%). MS, MP.

Preparation 55

α-Bromo-(2-methoxyphenyl)acetamide

The α-bromo-(2-methoxyphenyl)acetic acid (26.5 g, 108 mmol) was converted to product in a manner substantially analogous to Preparation 32 to yield 21.6 g. (82.0%). NMR.

Preparation 56

α-Bromo-isobutylacetamide

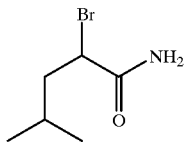

The α-bromo-(4-methyl)pentanoic acid (35.0 g, 179 mmol) was converted to product in a manner substantially analogous to Preparation 32 to yield 20.9 g. (60.1%). EA, MS(EI).

Preparation 57

α-Bromo-benzylacetamide

The α-bromo-benzylacetic acid (64.0 g, 279 mmol) was converted to product in a manner substantially analogous to Preparation 32 to yield 22.5 g. (35.4%). EA, MS(FD).

Preparation 58

α-Bromo-(4-nitrophenyl)acetamide

The α-bromo-(4-nitrophenyl)acetic acid (36.6 g, 141 mmol) was converted to product in a manner substantially analogous to Preparation 32 to yield 19.3 g. (52.9%). NMR.

Preparation 59

2,6-Difluoromandelic acid

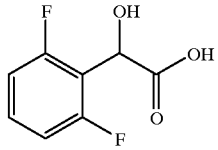

The 2,6-difluorobenzaldehyde (25.0 g, 176 mmol) and zinc iodide (5.0 mg, 0.02 mmol) were placed in a flame-dried 250 ml 3-necked round bottom flask under $N_2$. Trimethylsilyl cyanide (17.45 g, 176.0 mmol) was added dropwise over 20 minutes and the reaction was allowed to stir for 72 hours. 9N HCl (200 ml) was added and the solution was refluxed overnight. The reaction was cooled to RT and extracted with $Et_2O$. The $Et_2O$ was extracted with saturated $NaHCO_3$ then acidified to pH 1 with 5N HCl. The acidic solution was extracted with $Et_2O$ and the organic layer dried over $Na_2SO_4$. The $Na_2SO_4$ was filtered and the $Et_2O$ removed in vacuo leaving a white solid which was recrystallized from $CHCl_3$ yielding 23.6 g (71%) of product as a white solid. NMR, MS, IR, EA.

Preparation 60

2,3,4,5,6-Pentafluoromandelic acid

The 2,3,4,5,6-pentafluorobenzaldehyde (49.4 g, 252 mmol) was converted to product in a manner substantially analogous to Preparation 59 to yield 52.3 g. (86.0). EA, MS(FD).

Preparation 61

2-Trifluoromethylmandelic acid

The 2-trifluoromethylbenzaldehyde (43.9 g, 252 mmol) was converted to product in a manner substantially analogous to Preparation 59 to yield 39.1 g. (70.5%). EA, MS(FD).

Preparation 62

Thiophen-3-ylmandelic acid

The thiophen-3-ylcarboxaldehyde (28.3 g, 252 mmol) was converted to product in a manner substantially analogous to Preparation 59 to yield 13.4 g. (33.8%). EA, MS(FD).

Preparation 63

2-Trifluoromethyl-4-fluoromandelic acid

The 2-trifluoromethyl-4-fluorobenzaldehyde (48.4 g, 252 mmol) was converted to product in a manner substantially analogous to Preparation 59 to yield 50.1 g. (84%). EA, MS(FD).

Preparation 64

2-Fluoro-6-trifluoromethylmandelic acid

The 2-fluoro-6-trifluoromethylbenzaldehyde (48.4 g, 252 mmol) was converted to product in a manner substantially analogous to Preparation 59 to yield 49.7 g. (84%). EA, MS(FD).

Preparation 65

4-Carboxymandelic acid

The 4-cyanobenzaldehyde (33.0 g, 252 mmol) was converted to product in a manner substantially analogous to Preparation 59 to yield 27.0 g. (54.6%). MS(FD), NMR.

Preparation 66

α-O-acetyl-(2,6-difluorophenyl)acetic acid

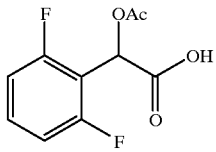

30% HBr in acetic acid (150 ml) was added to 2,6-difluoromandelic acid (16.9 g, 89.9 mmol) in 50 ml of acetic acid and stirred overnight. The reaction was poured onto 1.5 L of ice water and stirred for 1 hour. The aqueous solution was extracted with $Et_2O$ and the organic layer dried over $Na_2SO_4$. The $Na_2SO_4$ was filtered and the $Et_2O$ removed in vacuo leaving a white solid which was recrystallized from $Et_2O$/hexanes yielding 18.54 (90%) of product as a white solid. EA, MS(FD).

Preparation 67

α-O-acetyl-(2,3,4,5,6-pentafluorophenyl)acetic acid

The 2,3,4,5,6-pentafluoromandelic acid (70.5 g, 291 mmol) was converted to product in a manner substantially analogous to Preparation 66 to yield 82.8 g. (100%). EA, MS(FD).

Preparation 68

α-O-acetyl-(2-trifluoromethylphenyl)acetic acid

The 2-trifluoromethylmandelic acid (19.8 g, 90.0 mmol) was converted to product in a manner substantially analogous to Preparation 66 to yield 20.8 g. (88.0%). EA, MS(FD).

Preparation 69

α-O-acetyl-(2-trifluoromethyl-4-fluorophenyl)acetic acid

The 2-trifluoromethyl-4-fluoromandelic acid (49.4 g, 208 mmol) was converted to product in a manner substantially analogous to Preparation 66 to yield 58.1 g. (100%). EA, MS(FD).

Preparation 70

α-O-acetyl-(2-fluoro-6-trifluoromethylphenyl)acetic acid

The 2-fluoro-6-trifluoromethylmandelic acid (48.4 g, 252 mmol) was converted to product in a manner substantially analogous to Preparation 66 to yield 50.1 g. (84%). EA, MS(FD).

Preparation 71

α-O-acetyl-(4-trifluoromethylphenyl)acetic acid

The 4-trifluoromethylmandelic acid (19.8 g, 89.9 mmol) was converted to product in a manner substantially analogous to Preparation 66 to yield 20.3 g. (86%). MS(FD), NMR.

Preparation 72

α-O-acetyl-(4-carboxyphenyl)acetic acid

The 4-carboxymandelic acid (27.0 g, 138 mmol) was converted to product in a manner substantially analogous to Preparation 66 to yield 27.5 g. (83.9%). MS(FD), NMR.

Preparation 73

α-O-acetyl-(2,6-difluorophenyl)acetamide

The α-O-acetyl-(2,6-difluorophenyl)acetic acid (18.5 g, 80.4 mmol), in 200 ml of dry $CH_2Cl_2$, and 3 drops DMF were cooled in an ice bath under $N_2$. Oxalyl chloride (50.0 g, 448 mmol) in 50 ml dry $CH_2Cl_2$ was added dropwise over 25 minutes. The ice bath was removed and the reaction was allowed to stir for 3 hours. The solvent was removed in vacuo then azeotroped with toluene (3×25 ml). The remaining oil was dissolved in 100 ml of toluene and 700 ml of hexanes and stirred vigorously with a mechanical stirrer. Ammonia gas was then blown through a gas dispersion tube over the top of this solution for 1 hour. The resulting solid was filtered and solvents removed in vacuo. The solid was dissolved in $EtOAc/H_2O$ and the organic layer washed with 1N HCl, saturated $NaHCO_3$, brine, then dried over $Na_2SO_4$. The $Na_2SO_4$ was filtered and the EtOAc removed in vacuo. The remaining solid was recrystallized from EtOAc/hexanes yielding 16.7 g (90%) of the desired product.

Preparation 74

α-O-acetyl-(2,3,4,5,6-pentafluorophenyl)acetamide

The α-O-acetyl-(2,3,4,5,6-pentafluorophenyl)acetic acid (106 g, 373 mmol) was converted to product in a manner substantially analogous to Preparation 73 to yield 94.0 g. (89%). EA, MS(FD).

Preparation 75

α-O-acetyl-(2-trifluoromethylphenyl)acetamide

The α-O-acetyl-(2-trifluoromethylphenyl)acetic acid (20.8 g, 79.4 mmol) was converted to product in a manner substantially analogous to Preparation 73 to yield 18.8 g. (90.7%). EA, MS(FD).

Preparation 76

α-O-acetyl-(2-trifluoromethyl-4-fluorophenyl) acetamide

The α-O-acetyl-(2-trifluoromethyl-4-fluorophenyl)acetic acid (58.1 g, 208 mmol) was converted to product in a manner substantially analogous to Preparation 73 to yield 52.4 g. (90.0%). EA, MS(FD).

Preparation 77

α-O-acetyl-(2-fluoro-6-trifluoromethylphenyl) acetamide

The α-O-acetyl-(2-fluoro-4-trifluoromethylphenyl)acetic acid (53.4 g, 191 mmol) was converted to product in a manner substantially analogous to Preparation 73 to yield 47.9 g. (90%). EA, MS(FD).

Preparation 78

α-O-acetyl-(4-trifluoromethylphenyl)acetamide

The α-O-acetyl-(4-trifluoromethylphenyl)acetic acid (20.3 g, 77.3 mmol) was converted to product in a manner substantially analogous to Preparation 73 to yield 18.8 g. (93%).

Preparation 79

Methyl-(α-hydroxy-4-carbomethoxybenzyl)acetate

The α-O-acetyl-(4-carboxyphenyl)acetic acid (23.2 g, 97.3 mmol) was suspended in 300 ml of $CH_2Cl_2$ and 3 drops of DMF was added while the reaction stirred under $N_2$ in an ice bath. Oxalyl chloride (50.0 g, 448 mmol) in 50 ml of dry $CH_2Cl_2$ was added dropwise over 20 minutes. The ice bath was removed and the reaction stirred at RT for about 5 hours (until all solids in solution). The solvents were removed and the residue and 200 ml of MeOH were placed in an addition funnel and stirred overnight. The solvents were then removed and the residue taken up in EtOAc. The EtOAc was washed with $NaHCO_3$ (3×100 ml), brine, and then dried over $NaSO_4$. The EtOAc was removed in vacuo to give 22 g of an oil. (100%). EA, MS(FD).

Preparation 80

α-Hydroxy-(2,6-difluorophenyl)acetamide

The α-O-acetyl-(2,6-difluorophenyl)acetamide (16.7 g, 73.0 mmol) was dissolved in 125 ml of methanol and 35 ml of diisopropylethylamine then refluxed for 3 hours. The solvents were removed in vacuo and the remaining solid was recrystallized from EtOAc/hexanes yielding 11.42 g (84%) of product as a white solid. EA, MS(FD).

Preparation 81

α-Hydroxy-(2,3,4,5,6-pentafluorophenyl)acetamide

The α-O-acetyl-(2,3,4,5,6-pentafluorophenyl)acetamide (83.0 g, 293 mmol) was converted to product in a manner substantially analogous to Preparation 80 to yield 66.6 g. (94%). EA, MS(FD).

Preparation 82

α-Hydroxy-(2-trifluoromethylphenyl)acetamide

The α-O-acetyl-(2-trifluoromethylphenyl)acetamide (18.4 g, 70.6 mmol) was converted to product in a manner substantially analogous to Preparation 80 to yield 14.3 g. (92.4%). MS(FD), NMR.

Preparation 83

α-Hydroxy-(2-trifluoromethyl-4-fluorophenyl) acetamide

The α-O-acetyl-(2-trifluoromethyl-4-fluorophenyl) acetamide (50.4 g, 181 mmol) was converted to product in a manner substantially analogous to Preparation 80 to yield 40.9 g. (95%). EA, MS(FD).

Preparation 84

α-Hydroxy-(2-fluoro-6-trifluoromethylphenyl) acetamide

The α-O-acetyl-(2-fluoromethyl-6-trifluoromethylphenyl)acetamide (44.6 g, 160 mmol) was converted to product in a manner substantially analogous to Preparation 80 to yield 32.1 g. (85%). EA, MS(FD).

Preparation 85

α-Hydroxy-(4-trifluoromethylphenyl)acetamide

The α-O-acetyl-(4-trifluoromethylphenyl)acetamide (18.8 g, 65.3 mmol) was converted to product in a manner substantially analogous to Preparation 80 to yield 13.8 g. (96.1w). EA, MS(FD).

Preparation 86

α-Hydroxy-(4-carbomethoxyphenyl)acetamide

Freshly prepared ammonia in methanol (300 ml) was added to methyl-(α-hydroxy-4-carbomethoxybenzyl)acetate (21.8 g, 97.3 mmol) and stirred overnight. The solvents were removed in vacuo and the residue recrystalized from $CH_2Cl_2$ to give 17.5 g of product. (85.7%). EA, MS(FD).

Preparation 87

α-O-toluenesulfonylimido-(2,6-difluorophenyl) acetamide

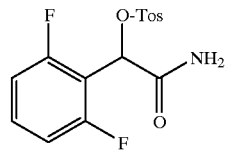

The α-hydroxy-(2,6-difluorophenyl)acetamide (9.80 g, 52.4 mmol), 4-dimethylaminopyridine (500 mg, 4.10 mmol), and diisopropylethylamine (10.04 ml, 57.6 mmol) were combined in 300 ml of dry $CH_2Cl_2$ under $N_2$. The p-toluenesulfonyl chloride (11.0 g, 57.6 mmol) was added and the reaction was stirred overnight. The solvents were removed in vacuo and the remaining solids dissolved in EtOAc. The EtOAc was washed with 1N HCl, saturated $NaHCO_3$, brine, then dried over $Na_2SO_4$. The $Na_2SO_4$ was filtered and the EtOAc removed in vacuo leaving a white solid. The solids were recrystallized from EtOAc/hexanes yielding 15.8 g (88%) of the desired product as a white powder. EA, MS(FD).

Preparation 88

α-O-toluenesulfonylimido-(2,3,4,5,6-pentafluorophenyl)acetamide

The α-hydroxy-(2,3,4,5,6-pentafluorophenyl)acetamide (12.1 g, 50.0 mmol) was converted to product in a manner substantially analogous to Preparation 87 to yield 18.3 g. (92%). EA, MS(FD).

Preparation 89

α-O-toluenesulfonylimido-(2-trifluoromethylphenyl) acetamide

The α-hydroxy-(2-trifluoromethylphenyl)acetamide (14.3 g, 65.2 mmol) was converted to product in a manner substantially analogous to Preparation 87 to yield 21.0 g. (86%). EA, MS(FD), Preparation 90

α-O-toluenesulfonylimido-(2-trifluoromethyl-4-fluorophenyl)acetamide

The α-hydroxy-(2-trifluoromethyl-4-fluorophenyl) acetamide (11.9 g, 50.0 mmol) was converted to product in a manner substantially analogous to Preparation 87 to yield 17.0 g. (87%). EA, MS(FD).

Preparation 91

α-O-toluenesulfonylimido-(2-fluoro-6-trifluoromethylphenyl)acetamide

The α-hydroxy-(2-fluoro-4-trifluoromethylphenyl) acetamide (11.9 g, 50.0 mmol) was converted to product in a manner substantially analogous to Preparation 87 to yield 17.8 g. (91%). EA, MS(FD).

Preparation 92

α-O-toluenesulfonylimido-(4-trifluoromethylphenyl) acetamide

The α-hydroxy-(4-trifluoromethylphenyl)acetamide (9.35 g, 42.7 mmol) was converted to product in a manner substantially analogous to Preparation 87 to yield 12.7 g. (80%). EA, MS(FD).

Preparation 93

α-O-toluenesulfonylimido-(4-carbomethoxyphenyl) acetamide

The α-hydroxy-(4-carbomethoxyphenyl)acetamide (10.5 g, 50.0 mmol) was converted to product in a manner substantially analogous to Preparation 87 to yield 14.6 g. (80.2%). EA, MS(FD).

Preparation 94

1,2-Dihydro-2-toluenesulfonylimido-5-benzoyl-N-(1-[2,4-difluorophenyl]-carbamoylmethyl)-pyridine

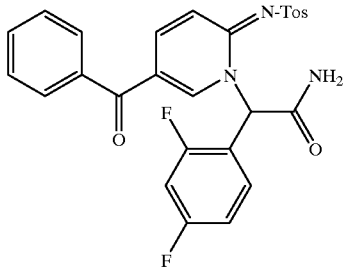

The 1,2-dihydro-2-toluenesulfonylimido-5-benzoylpyridine (10.6 g, 30.0 mmol) was dissolved in 75 ml of DMF and stirred in a flame dried flask under $N_2$. Sodium hydride (1.32 g, 33.0 mmol) was added and the solution stirred for 1.5 hours. The α-bromo-(2,4-difluorophenyl) acetamide (7.88 g, 31.5 mmol) was then added and the solution was allowed to stir at RT for 7 days. The reaction was worked up by pouring the solution onto 2.5 L of $H_2O$ and stirring for 1 hour. The resulting precipitate was collected by filtration. The filter cake was recrystalized from EtOAc/hexane to yield 13.2 g. (84%). EA, MS(FD).

Preparation 95

1,2-Dihydro-2-toluenesulfonylimido-5-benzoyl-N-(1-[4-fluorophenyl]-carbamoylmethyl)-pyridine The 1,2-dihydro-2-toluenesulfonylimido-5-benzoylpyridine (27.1 g, 77.0 mmol) and α-bromo-(4-fluorophenyl)acetamide (19.6 g, 84.5 mmol) were converted to product in a manner substantially analogous to Preparation 94 to yield 35.0 g. (90.4%). EA, MS(FD).

Preparation 96

1,2-Dihydro-2-toluenesulfonylimido-5-benzoyl-N-(1-[4-methoxyphenyl]-carbamoylmethyl)-pyridine The 1,2-dihydro-2-toluenesulfonylimido-5-benzoylpyridine (10.6 g, 30.0 mmol) and α-bromo-(4-methoxyphenyl)acetamide (8.05 g, 33.0 mmol) were converted to product in a manner substantially analogous to Preparation 94, except cesium fluoride was employed instead of sodium hydride and sodium iodide (4.50 g, 30.0 mmol) was added, to yield 6.32 g. (41.0%). EA, MS(FD).

Preparation 97

1,2-Dihydro-2-toluenesulfonylimido-5-benzoyl-N-(1-[napth-2-yl]-carbamoylmethyl)-pyridine The 1,2-dihydro-2-toluenesulfonylimido-5-benzoylpyridine (18.5 g, 52.7 mmol) and α-bromo-(napth-2-yl)acetamide (14.6 g, 55.3 mmol) were converted to product in a manner substantially analogous to Preparation 94 to yield 15.0 g. (53.3w). EA, MS(FD).

Preparation 98

1,2-Dihydro-2-toluenesulfonylimido-5-benzoyl-N-(1-napthyl-carbamoylmethyl)-pyridine The 1,2-dihydro-2-toluenesulfonylimido-5-benzoylpyridine (14.6 g, 41.5 mmol) and α-bromo-(napth-1-yl)acetamide (11.5 g, 43.6 mmol) were converted to product in a manner substantially analogous to Preparation 94 to yield 14.3 g. (64%). EA, MS(FD).

Preparation 99

1,2-Dihydro-2-toluenesulfonylimido-5-benzoyl-N-(1-(2-fluorophenyl]-carbamoylmethyl)-pyridine The 1,2-dihydro-2-toluenesulfonylimido-5-benzoylpyridine (12.3 g, 35.1 mmol) and α-bromo-(2-fluorophenyl)acetamide (8.54 g, 36.8 mmol) were converted to product in a manner substantially analogous to Preparation 94 to yield 16.5 g. (93.6%). EA, MS(FD).

Preparation 100

1,2-Dihydro-2-toluenesulfonylimido-5-benzoyl-N-(1-[3-fluorophenyl-carbamoylmethyl)-pyridine The 1,2-dihydro-2-toluenesulfonylimido-5-benzoylpyridine (23.6 g, 66.9 mmol) and α-bromo-(3-fluorophenyl)acetamide (16.3 g, 70.3 mmol) were converted to product in a manner substantially analogous to Preparation 94 to yield 29.8 g. (88.5%). EA, MS(FD).

Preparation 101

1,2-Dihydro-2-toluenesulfonylimido-5-benzoyl-N-(1-[3,5-difluorophenyl]-carbamoylmethyl)-pyridine The 1,2-dihydro-2-toluenesulfonylimido-5-benzoylpyridine (10.6 g, 30.0 mmol) and α-bromo-(3,5-difluorophenyl)acetamide (7.88 g, 31.5 mmol) were converted to product in a manner substantially analogous to Preparation 94 to yield 14.2 g. (91.0%). EA, MS(FD).

Preparation 102

1,2-Dihydro-2-toluenesulfonylimido-5-benzoyl-N-(1-[2,5-difluorophenyl]-carbamoylmethyl)-pyridine The 1,2-dihydro-2-toluenesulfonylimido-5-benzoylpyridine (10.6 g, 30.0 mmol) and α-bromo-(2,5-difluorophenyl)acetamide (7.88 g, 31.5 mmol) were converted to product in a manner substantially analogous to Preparation 94 to yield 15.3 g. (98%). EA, MS(FD).

Preparation 103

1,2-Dihydro-2-toluenesulfonylimido-5-benzoyl-N-(1-[3-trifluoromethylphenyl]-carbamoylmethyl)-pyridine The 1,2-dihydro-2-toluenesulfonylimido-5-benzoylpyridine (10.6 g, 30.0) and α-bromo-(3- trifluoromethylphenyl)acetamide (8.88 g, 31.5 mmol) were converted to product in a manner substantially analogous to Preparation 94 to yield 12.7 g. (76%). EA, MS(FD).

Preparation 104

1,2-Dihydro-2-toluenesulfonylimido-5-benzoyl-N-(1-[4-bromophenyl]-carbamoylmethyl)-pyridine The 1,2-dihydro-2-toluenesulfonylimido-5-benzoylpyridine (10.6 g, 30.0) and α-bromo-(4-bromophenyl)acetamide (9.23 g, 31.5 mmol) were converted to product in a manner substantially analogous to Preparation 94 to yield 13.7 g. (81%). EA, MS(FD).

Preparation 105

1,2-Dihydro-2-toluenesulfonylimido-5-benzoyl-N-(1-[2,3,4-trifluorophenyl]-carbamoylmethyl)-pyridine The 1,2-dihydro-2-toluenesulfonylimido-5-benzoylpyridine (10.6 g, 30.0 mmol) and α-bromo-(2,3,4-trifluorophenyl)acetamide (8.44 g, 31.5 mmol) were converted to product in a manner substantially analogous to Preparation 94 to yield 11.3 g. (70%).

Preparation 106

1,2-Dihydro-2-toluenesulfonylimido-5-benzoyl-N-(1-[3,4-difluorophenyl]-carbamoylmethyl)-pyridine The 1,2-dihydro-2-toluenesulfonylimido-5-benzoylpyridine (10.6 g, 30.0 mmol) and α-bromo-(3,4-difluorophenyl)acetamide (7.88 g, 31.5 mmol) were converted to product in a manner substantially analogous to Preparation 94 to yield 9.53 g. (61%). EA, MS(FD).

Preparation 107

1,2-Dihydro-2-toluenesulfonylimido-5-benzoyl-N-(1-[3,4-dichlorophenyl]-carbamoylmethyl)-pyridine The 1,2-dihydro-2-toluenesulfonylimido-5-benzoylpyridine (10.6 g, 30.0 mmol) and α-bromo-(3,4-dichlorophenyl)acetamide (9.00 g, 31.5 mmol) were converted to product in a manner substantially analogous to Preparation 94 to yield 13.8 g. (83%). EA, MS(FD).

Preparation 108

1,2-Dihydro-2-toluenesulfonylimido-5-benzoyl-N-(1-[2,4,5-trifluorophenyl]-carbamoylmethyl)-pyridine The 1,2-dihydro-2-toluenesulfonylimido-5-benzoylpyridine (9.18 g, 26.1 mmol) and α-bromo-(2,4,5-trifluorophenyl)acetamide (7.34 g, 27.4 mmol) were converted to product in a manner substantially analogous to Preparation 94 to yield 11.6 g. (83%). MS(FAB), NMR.

Preparation 109

1,2-Dihydro-2-toluenesulfonylimido-5-benzoyl-N-(1-[2-chlorophenyl]-carbamoylmethyl)-pyridine The 1,2-dihydro-2-toluenesulfonylimido-5-benzoylpyridine (10.6 g, 30.0 mmol) and α-bromo-2-chlorophenylacetamide (7.83 g, 31.5 mmol) were converted to product in a manner substantially analogous to Preparation 94 to yield 10.4 g. (69%). EA, MS(FD).

Preparation 110

1,2-Dihydro-2-toluenesulfonylimido-5-benzoyl-N-(1-[3-chlorophenyl]-carbamoylmethyl)-pyridine The 1,2-dihydro-2-toluenesulfonylimido-5-benzoylpyridine (10.6 g, 30.0 mmol) and α-bromo-(3-chlorophenyl)acetamide (7.83 g, 31.5 mmol) were converted to product in a manner substantially analogous to Preparation 94 to yield 13.4 g. (77%). EA, MS(FD).

Preparation 111

1,2-Dihydro-2-toluenesulfonylimido-5-benzoyl-N-(1-[4-chlorophenyl]-carbamoylmethyl)-pyridine The 1,2-dihydro-2-toluenesulfonylimido-5-benzoylpyridine (10.6 g, 30.0 mmol) and α-bromo-(4-chlorophenyl)acetamide (7.81 g, 31.5 mmol) were converted to product in a manner substantially analogous to Preparation 94 to yield 13.8 g. (88%). EA, MS(FD).

Preparation 112

1,2-Dihydro-2-toluenesulfonylimido-5-benzoyl-N-(1-[4-trifluoromethoxyphenyl]-carbamoylmethyl)-pyridine The 1,2-dihydro-2-toluenesulfonylimido-5-benzoylpyridine (10.6 g, 30.0 mmol) and α-bromo-(4-trifluoromethoxyphenyl)acetamide (9.83 g, 33.0 mmol) were converted to product in a manner substantially analogous to Preparation 94, except cesium fluoride was employed instead of sodium hydride, to yield 13.2 g. (77%). EA, MS(FD).

Preparation 113

1,2-Dihydro-2-toluenesulfonylimido-5-benzoyl-N-(1-[3-trifluoromethoxyphenyl]-carbamoylmethyl)-pyridine The 1,2-dihydro-2-toluenesulfonylimido-5-benzoylpyridine (10.6 g, 30.0 mmol) and α-bromo-(3-trifluoromethoxyphenyl)acetamide (9.43 g, 31.6 mmol) were converted to product in a manner substantially analogous to Preparation 94 to yield 12.5 g. (73%). EA, MS(FD).

Preparation 114

1,2-Dihydro-2-toluenesulfonylimido-5-benzoyl-N-(1-[2-fluoro-4-trifluoromethylphenyl]-carbamoylmethyl)-pyridine The 1,2-dihydro-2-toluenesulfonylimido-5-benzoylpyridine (7.04 g, 20.0 mmol) and α-bromo-(2-fluoro-4-trifluoromethylphenyl)acetamide (6.50 g, 21.7 mmol) were converted to product in a manner substantially analogous to Preparation 94 to yield 10.1 g. (88%). EA, MS(FD).

Preparation 115

1,2-Dihydro-2-toluenesulfonylimido-5-benzoyl-N-(1-phenyl-carbamoylmethyl)-pyridine The 1,2-dihydro-2-toluenesulfonylimido-5-benzoylpyridine (10.6 g, 30.0 mmol) and α-bromo-phenylacetamide (6.74 g, 31.5 mmol) were converted to product in a manner substantially analogous to Preparation 94, except cesium fluoride was employed instead of sodium hydride, to yield 13.3 g. (91%). EA, MS(FD).

Preparation 116

1,2-Dihydro-2-toluenesulfonylimido-5-benzoyl-N-(1-[4-trifluoromethylphenyl]-carbamoylmethyl)-pyridine The 1,2-dihydro-2-toluenesulfonylimido-5-benzoylpyridine (10.0 g, 28.5 mmol) and α-O-toluenesulfonylimido-(4-trifluoromethylphenyl)acetamide (11.1 g, 29.9 mmol) were converted to product in a manner substantially analogous to Preparation 94 to yield 13.9 g. (88%). EA, MS(FD).

Preparation 117

1,2-Dihydro-2-toluenesulfonylimido-5-benzoyl-N-(1-[2-fluoro-6-trifluoromethylphenyl]-carbamoylmethyl)-pyridine The 1,2-dihydro-2-toluenesulfonylimido-5-benzoylpyridine (10.6 g, 30.0 mmol) and α-O-toluenesulfonylimido-(2-trifluoromethyl-6-fluorophenyl) acetamide (12.9 g, 33.0 mmol) were converted to product in a manner substantially analogous to Preparation 94, except that diisopropylethylamine was employed instead of sodium hydride and the reaction was conducted between 90 and 100° C., to yield 2.90 g. (16.9%). MS(FD), NMR.

Preparation 118

1,2-Dihydro-2-toluenesulfonylimido-5-benzoyl-N-(1-[2,3,4,5,6-pentafluorophenyl]-carbamoylmethyl)-pyridine The 1,2-dihydro-2-toluenesulfonylimido-5-benzoylpyridine (5.28 g, 15.0 mmol) and α-O-toluenesulfonylimido-(2,3,4,5,6-pentafluorophenyl) acetamide (5.93 g, 15.0 mmol) were converted to product in a manner substantially analogous to Preparation 94, except that cesium carbonate was employed instead of sodium hydride and the reaction was conducted at 60° C., to yield 5.07 g. (59%). EA, MS(FD).

Preparation 119

1,2-Dihydro-2-toluenesulfonylimido-5-benzoyl-N-(1-[2,6-difluorophenyl]-carbamoylmethyl)-pyridine The 1,2-dihydro-2-toluenesulfonylimido-5-benzoylpyridine (10.6 g, 30.0 mmol) and α-O-toluenesulfonylimido-(2,6-difluorophenyl)acetamide (10.7 g, 31.5 mmol) were converted to product in a manner substantially analogous to Preparation 94 except that the reaction was run at 60° C. to yield 7.44 g. (48%). EA, MS(FD).

Preparation 120

1,2-Dihydro-2-toluenesulfonylimido-5-benzoyl-N-(1-[2-trifluoromethylphenyl]-carbamoylmethyl)-pyridine The 1,2-dihydro-2-toluenesulfonylimido-5-benzoylpyridine (10.6 g, 30.0 mmol) and α-O-toluenesulfonylimido-(2-trifluoromethylphenyl)acetamide (11.8 g, 31.5 mmol) were converted to product in a manner substantially analogous to Preparation 94 except that the reaction was run at 70° C. to yield 7.37 g. (44.4%). EA, MS(FD).

Preparation 121

1,2-Dihydro-2-toluenesulfonylimido-5-benzoyl-N-(1-[thiophen-3-yl]-carbamoylmethyl)-pyridine The 1,2-dihydro-2-toluenesulfonylimido-5-benzoylpyridine (9.90 g, 28.1 mmol) and α-O-toluenesulfonylimido-(thiophen-3-yl)acetamide (6.50 g, 29.6 mmol) were converted to product in a manner substantially analogous to Preparation 94 to yield 11.3 g. (81.7%). EA, MS(FD).

Preparation 122

1,2-Dihydro-2-toluenesulfonylimido-5-benzoyl-N-(1-[2-trifluoromethyl-4-fluorophenyl]-carbamoylmethyl)-pyridine The 1,2-dihydro-2-toluenesulfonylimido-5-benzoylpyridine (10.6 g, 30.0 mmol) and α-O-toluenesulfonylimido-(2-trifluoromethyl-6-fluorophenyl) acetamide (12.9 g, 33.0 mmol) were converted to product in a manner substantially analogous to Preparation 94, except that diisopropylethylamine was employed instead of sodium hydride and the reaction was conducted between 50 and 60° C., to yield 14.5 g. (84%). EA, MS(FD).

Preparation 123

1,2-Dihydro-2-toluenesulfonylimido-5-benzoyl-N-(1-benzyl-carbamoylmethyl)-pyridine The 1,2-dihydro-2-toluenesulfonylimido-5-benzoylpyridine (10.6 g, 30.0 mmol) and α-bromo-benzylacetamide (7.52 g, 33.0 mmol) were converted to product in a manner substantially analogous to Preparation 94 to yield 802 mg. (5.36%). MS(FD), NMR.

Preparation 124

1,2-Dihydro-2-toluenesulfonylimido-5-benzoyl-N-(1-isobutyl-carbamoylmethyl)-pyridine The 1,2-dihydro-2-toluenesulfonylimido-5-benzoylpyridine (7.04 g, 20.0 mmol) and α-bromo-isobutylacetamide (8.54 g, 44.0 mmol) were converted to product in a manner substantially analogous to Preparation 94, except that cesium carbonate was employed instead of sodium hydride, to yield 3.35 g. (36.0%). EA, MS(FD).

Preparation 125

1,2-Dihydro-2-toluenesulfonylimido-5-benzoyl-N-(1-[2-methoxyphenyl]-carbamoylmethyl)-pyridine The 1,2-dihydro-2-toluenesulfonylimido-5-benzoylpyridine (10.6 g, 30.0 mmol) and α-O-toluenesulfonylimido-(2-methoxyphenyl)acetamide (7.69 g, 31.5 mmol) were converted to product in a manner substantially analogous to Preparation 94 to yield 10.4 g. (68%). EA, MS(FD).

Preparation 126

1,2-Dihydro-2-toluenesulfonylimido-5-benzoyl-N-(1-[4-carbomethoxyphenyl]-carbamoylmethyl)-pyridine The 1,2-dihydro-2-toluenesulfonylimido-5-benzoylpyridine (12.0 g, 34.2 mmol) and α-O-toluenesulfonylimido-(4-carbomethoxyphenyl)acetamide (13.0 g, 35.9 mmol) were converted to product in a manner substantially analogous to Preparation 94 to yield 15.5 g. (83%). EA, MS(FD).

Preparation 127

1,2-Dihydro-2-toluenesulfonylimido-5-benzoyl-N-(1-[4-nitrophenyl]-carbamoylmethyl)-pyridine The 1,2-dihydro-2-toluenesulfonylimido-5-benzoylpyridine (10.6 g, 30.0 mmol) and α-bromo-(4- nitrophenyl)acetamide (8.55 g, 33.0 mmol) were converted to product in a manner substantially analogous to Preparation 94 to yield 15.3 g. (96.2%). MS(FD), NMR.

Preparation 128

1,2-Dihydro-2-toluenesulfonylimido-5-(4-fluorobenzoyl)-N-(1-[4-fluorophenyl]-carbamoylmethyl)-pyridine The 1,2-dihydro-2-toluenesulfonylimido-5-(4-fluorobenzoyl)pyridine (7.40 g, 20.0 mmol) and α-bromo-(4-fluorophenyl)acetamide (5.10 g, 22.0 mmol) were converted to product in a manner substantially analogous to Preparation 94 to yield 9.15 g. (88%). EA, MS(FD).

Preparation 129

1,2-Dihydro-2-toluenesulfonylimido-5-(4-fluorobenzoyl)-N-(1-[2-fluoro-4-trifluoromethylphenyl]-carbamoylmethyl)-pyridine The 1,2-dihydro-2-toluenesulfonylimido-5-benzoylpyridine (7.40 g, 20.0 mmol) and α-bromo-(2-fluoro-4-trifluoromethylphenyl)acetamide (8.60 g, 22.0 mmol) were converted to product in a manner substantially analogous to Preparation 94, except diisopropylethylamine was employed instead of sodium hydride, to yield 8.95 g. (76%). EA, MS(FD).

Preparation 130

2-Amino-5-carbomethoxy-pyridine

The 6-aminonicotinic acid (50.0 g, 0.362 mol) was dissolved in 3.5 L of MeOH under $N_2$ and chilled to 0° C. Hydrogen chloride gas was bubbled through the solution for 45 minutes with the temperature of the solution maintained between 0–15° C. The reaction was then heated to 65° C. for 4 hours. The MeOH was removed in vacuo and the residue taken up in 400 ml of $H_2O$. The pH was adjusted to about 6.3 with saturated $NaHCO_3$ to produce a precipitate. The precipitate was filtered and washed with $H_2O$. The filter cake was dried in vacuo at 80° C. to give 48.9 g of product. (88.7%). EA, MS(FD).

Preparation 131

2-toluenesulfonylimido-5-carbomethoxy pyridine

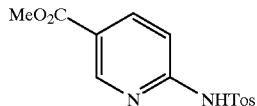

The 2-amino-5-carbomethoxy-pyridine (48.9 g, 0.321 mol) was dissolved in 400 ml of pyridine under $N_2$. p-Toluenesulfonic acid (73.5 g, 0.386 mol) was added and the solution heated to about 77.5° C. for 16 hours. The volume was reduced by ¾ in vacuo and 3.5 L of $H_2O$ was added. The resulting precipitate was filtered, washed with $H_2O$, and air dried to give 78.4 g of product. (79.7%). MS(FD), NMR.

Preparation 132

1,2-Dihydro-2-toluenesulfonylimido-5-carbomethoxy-(1-phenyl-carbamoylmethyl)pyridine

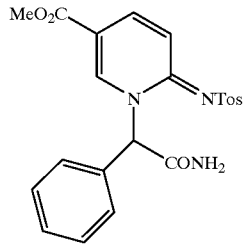

The 2-toluenesulfonylimido-5-methoxycarbonylpyridine (73.4 g, 0.240 mol) was suspended in 465 ml of DMF under $N_2$. Sodium hydride (60%, 10.1 g, 0.253 mol) was added in two portions. When the reactants were all in solution, (about 45 minutes) α-bromophenylacetamide (53.8 g, 0.252 mol) was added and the solution was allowed to stir for 64 hours. The volume was reduced by ⅔ in vacuo and the mixture was poured into 3 L of $H_2O$ and the mixture stirred for 2 hours. The precipitate was filtered and washed with $H_2O$. The filter cake was dried in vacuo at 60° C. to give 103.4 g of product. (98.2%). MS(FD), NMR.

Preparation 133

2-Trifluoroacetamido-3-phenyl-6-(carbomethoxy) imidazo[1,2-a]pyridine

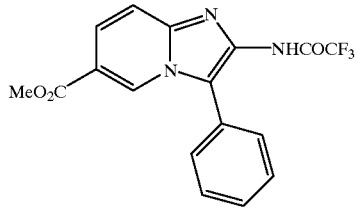

The 1,2-dihydro-2-toluenesulfonylimido-5-carbomethoxy-N-(1-phenyl-carbamoylmethyl)pyridine (103.3 g, 0.235 mol), trifluoroacetic anhydride (286 ml, 2.03 mol), and 573 ml of $CH_2Cl_2$ were combined under $N_2$ and heated to reflux. The solution was refluxed for 6 hours before concentrating in vacuo. The residue was dissolved in 1.5 L of $CH_2Cl_2$ and washed with saturated $NaHCO_3$ (3×500 ml), brine (2×500 ml), dried over $Na_2SO_4$, and filtered. The mother liquor was concentrated in vacuo, the residue taken up in 250 ml of hot EtOAc, and the product precipitated with 700 ml of hexanes. The precipatating mixture was placed in the freezer for 18 hours, then filtered, washed with hexane, and dried in vacuo at 40° C. to give 75.3 g of product. (quant. yeild). NMR.

Preparation 134

2-Amino-3-phenyl-6-(carbomethoxy)imidazo[1,2-a]pyridine

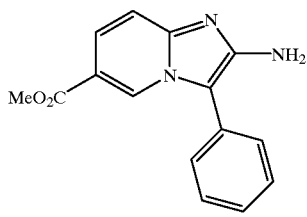

The 2-trifluoroacetamido-3-phenyl-6-(carbomethoxy)imidazo-[1,2-a]-pyridine (136 g, 0.440 mol) was dissolved in 845 ml of MeOH. The diisopropylethylamine (280 ml, 1.61 mol) was added over 15 minutes. The reaction was heated slowly to reflux and stirred for 68 hours. The reaction was cooled to 0° C. and the precipitate filtered. The filter cake was washed with cold MeOH and air dried to give 84.0 g of product. (71.4%). EA, MS(FD).

Preparation 135

2-Amino-3-phenyl-6-(carboxy)imidazo[1,2-a]pyridine

The 2-amino-3-phenyl-6-(carbomethoxy)imidazo-[1,2-a]-pyridine (83.9 g, 0.314 mol), lithium hyroxide monohydrate (65.9 g, 1.57 mol), 1113 ml of THF, and 371 ml of $H_2O$ were combined and stirred for 18 hours at RT. The reaction was concentrated in vacuo and the residue taken up in 5 L of $H_2O$. The pH was adjusted to 5 with 5N HCl. The resulting precipitate was filtered and air dried for 72 hours to give 80.5 g of product. (quant. yeild). NMR, MS(FD).

Preparation 136

2-Amino-3-phenyl-6-(N-methyl-N-methoxycarbamoyl)imidazo[1,2-a]pyridine

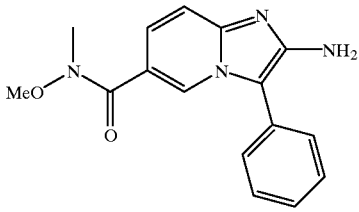

The 2-amino-3-phenyl-6-(carboxy)imidazo-[1,2-a]-pyridine (80.4 g, 0.317 mol) and N,O-dimethylhydroxylamine hydrochloride (92.8 g, 0.951 mol) were dissolved in 500 ml DMF under $N_2$. The diisopropylethylamine (123 g, 0.951 mol) was added and the mixture stirred for 30 minutes at RT. The 1-(3-dimethylaminopropyl)-3-ethylcarbodiimide hydrochloride (122 g, 0.634 mol) was added and allowed to stir for 19 hours at RT. The DMF was removed in vacuo and the residue was poured onto 4 L of $H_2O$. The aqueous layer was extracted with $CH_2Cl_2$ (3×500 ml) and the organic extracts were washed with brine, dried over $Na_2SO_4$, filtered, and concentrated in vacuo. The residue was taken up in 400 ml of EtOAc and stirred for 1 hour at RT to form the precipitate. The precipitate was filtered and washed with cold EtOAc. The filter cake was dried in vacuo at 40° C. to yield 55.5 g of product. (59.2%). MS(FD), NMR.

Preparation 137

2-Iodopyridine

A mixture of 2-bromopyridine (48.0 g, 303 mmol) and 240 ml of a 47% hydroiodic acid solution were refluxed for 8 hours and then stirred at RT for 3.5 days. The reaction mixture was poured onto aqueous NaOH (240 ml of 40% NaOH and 250 g of ice). The mixture was extracted with $Et_2O$ (3×200 ml) and the ether was washed with 100 ml of brine, dried over $Na_2SO_4$, filtered, and concentrated in vacuo. The residue was distilled in vacuo twice collecting fractions between 83 and 88° C. to yield 18.6 g of product. (30%). EA, MS(FD).

Preparation 138

4-Iodopyridine

The 4-bromopyridinehydrochloride (50.0 g, 257 mmol) was converted to product in a manner substantially analogous to Preparation 137 to yield 32.9 g. (62.4%). MS(FD), NMR.

Preparation 139

N-(3-phenyl-6-[N-methyl-N-carbamoyl]imidazo [1,2-a]pyridin-2-yl)-2,2,5,5-tetramethyl-1-aza-2,5-disilacyclopentane

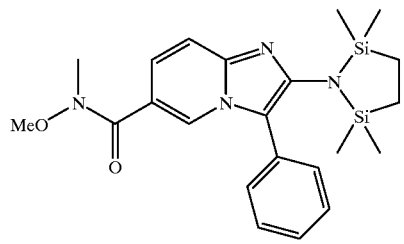

The 2-amino-3-phenyl-6-(N-methyl-N-methoxycarbamoyl)imidazo[1,2-a]pyridine (0.592 g, 2.00 mmol) was suspended in 20 ml of xylene. The 1,1'ethylenebis(N,N,1,1,-tetramethylsilanamine) (1.227 g, 5.28 mmol) and zinc iodide (10 mg, 0.031 mmol) were added and the mixture heated to reflux for 4 hours. The solvent was removed in vacuo and the crude product was used in subsequent reactions without further purification.

Preparation 140

1-Carbamoylmethyl-1,2-dihydro-2-toluenesulfonimido-6-benzoylpyridine

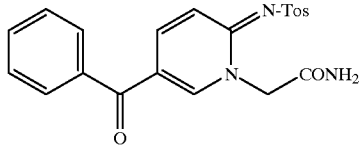

To a stirred suspension of 1,2-dihydro-2-toluenesulfonimido-5-benzoylpyridine (11.65 g, 32.10 mmol) in 100 ml of dry DMF was added diisopropylethylamine (6.34 ml, 34.2 mmol). After 15 minutes, the solution turned clear. Iodoacetamide (6.74 g, 34.2 mmol) was then added. The mixture was stirred for 24 hours and then poured onto H₂O (2 L) and stirred for an additional hour. The solids were collected and air-dried yielding 13.15 g (97%) of a white solid. EIMS, NMR.

Preparation 141

Diethyl-(N-methylcarbamoylmethyl)phosphonate

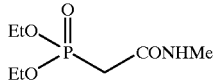

A solution of 4.12 mL of 400 methylamine (aqueous, 47 mmol) in 8.3 mL of MeOH was cooled to −78° C. Triethyl phosphonoacetate (8.85 mL, 44.2 mmol) was added dropwise over 10 minutes. The reaction mixture was allowed to warm to RT then stirred at this temperature for 29 hours (TLC: MeOH/CH₂CL₂: 1/9). The solvents were removed in vacuo at 35° C. and the resulting colorless liquid was purified by distillation (0.5 mmHg/130° C.). (87%). NMR.

Preparation 142

Isopropyl isopropanethiol-sulfonate iPr—S(O)₂—S-(iPr)

To a solution of diisopropylpropanethiol sulfonate (10.0 g, 66.5 mmol) in 55 ml of acetic acid was added dropwise 33% hydrogen peroxide (14.4 g, 140 mmol) over a 30 minute period at 0° C. After stirring for 24 hours at room temperature, the solvents were evaporated to dryness and the crude oil was purified by column chromatography (EtOAc/hexane) to give 8.5 g of a colorless oil product. (70%). ¹H-NMR, 13$^C$-NMR.

Preparation 143

1-Carbamoylmethyl-1,2-dihydro-2-toluenesulfonimido-6-(carbomethoxy)pyridine

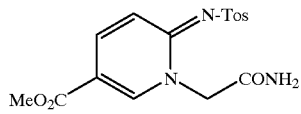

The 1,2-dihydro-2-toluenesulfonimido-5-methoxycarbonylpyridine (20 g, 65.3 mmol) was suspended in dry DMF (120 ml) and stirred under argon. Diisopropylethylamine (125.2 mL, 71.82 mmol) and 2-iodoacetamide (13.28 g, 71.82 mmol) were added and the reaction mixture was stirred at RT for 24 hours. The reaction was poured onto H₂O (60 mL) and stirred for 90 minutes. The solid was collected by filtration, washed with H₂O (1 L), Et₂O (200 mL), and dried in vacuo to give 21.8 g (91.7%) of desired product as a white solid. MS(FAB), NMR.

Preparation 144

2-Trifluoracetamido-6-carbomethoxy-imidazo[1,2-a]pyridine

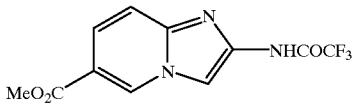

To a suspension of 1-carbamoylmethyl-1,2-dihydro-2-toluenesulfonimido-6-(carbomethoxy)pyridine (5.00 g, 13.8 mmol) in dry CH₂Cl₂ (75 mL), under an argon atmosphere, was added trifluoracetic anhydride (60 ml, 425 mmol). The resulting solution was refluxed for 3 hours. The solvents were removed in vacuo. The residue was taken up in EtOAc (150 mL) and the suspension was stirred for 30 minutes. The solids were collected, poured onto H₂O (50 mL) and stirred for 30 minutes. The solids were collected and dried in vacuo to give 1.92 g (49%) of product as a white solid. MS(FAB), NMR.

Preparation 145

2-Trifluoroacetamido-6-(N-methoxy-N-methylamido)-imidazo[1,2-a]pyridine

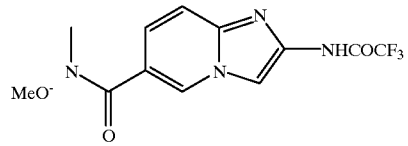

To a cooled solution (−20° C.) of 2-trifluoracetamido-6-carbomethoxy-imidazo[1,2-a]pyridine (1.50 g, 5.23 mmol) and N—O-dimethylaminohydrochloride (893 mg, 9.15 mmol) in 30 ml of THF was added dropwise isopropyl magnesium chloride (12.0 ml, 24.1 mmol) over 20 minutes. The reaction mixture was stirred at −20° C. for 1 hour. The solvent was removed and the residue was dissolved in EtOAc and washed with saturated NH₄Cl. The combined organic extracts were dried (Na₂SO₄) and the solvent was removed in vacuo to give 1.23 g of a white solid. (75%). HRMS calcd. for $C_{12}H_{11}N_4O_3F_3$: 316.0783. Found: 316.0782, NMR.

Preparation 146

2-Trifluoroacetamido-3-phenyl-6-(N-methyl-N-methoxycarbamoyl)-imidazo[1,2-a]pyridine

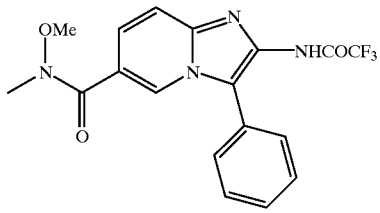

The 2-trifluoroacetamido-3-phenyl-6-carbomethoxy-imidazo[1,2-a]pyridine (12.0 g, 33 mol) was converted to product in a manner substantially analogous to Preparation 189 to yield 8.0 g. (68%). MS(FAB), NMR.

Preparation 147

2-Chloro-5-(N-methyl-N-methoxycarbamoyl) pyridine

To a solution of 2,6-dichloronicotine (880 mg, 5 mmol) in 20 ml of acetone was added N-methoxy-N-methylamino hydrochloride (500 mg, 5.13 mmol) and diisopropylethylamine (1.33 g, 10.2 mmol). The reaction mixture was stirred for 10 minutes. The solvent was removed in vacuo and the resulting residue was purified by column chromatography to give 950 mg of product as an oil. (95%).

Preparation 148

2-Chloro-5-(1-phenyl-2-N-methylcarbamoylvinyl) pyridine

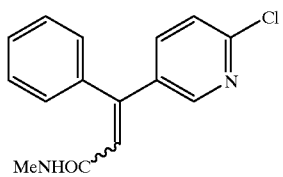

To a solution of potassium hexamethyldisilazide (9.2 g, 46 mmol) in 25 mL of dry DMF under an argon atmosphere at 0° C. was added a solution of diethyl(N-methylcarbamoylmethyl)phosphonate (4.81 g, 23.0 mmol) in 50 mL of dry DMF. The reaction mixture was stirred at 0° C. for about 2 hours. A solution of 2-chloro-5-benzoylpyridine (2.5 g, 11.5 mmol) in 25 mL of dry DMF was added via cannula. The ice bath was removed and the resulting brown solution was allowed to warm to RT and stir for 16 hours. The mixture was quenched with saturated $NH_4Cl$ (30 mL) and extracted with EtOAc. The organic layers were combined and washed with saturated $NH_4Cl$ and then with brine. After drying over $NaSO_4$, the solvent was removed in vacuo and the resulting residue was passed through a chromatography column (Hex/AcOEt 1:1) to give 1.5 g (50%) of a mixture of isomers E:Z in 1:1.5 ratio. The isomers were separated by crystallization. Z-isomer, IR, NMR and the E-isomer, IR, NMR.

Preparation 149

2-Chloro-5-(2,3-difluorobenzoyl)pyridine

To a solution of 1-bromo-2,3-difluorobenzene (0.114 g, 0.746 mmol) in 3 ml of dry THF was added, at −78° C., n-butyl lithium (1.6 M in hexane, 0.47 ml, 0.749 mmol). The reaction mixture was stirred at this temperature for 1 hour. A solution of 6-chloro-N-methoxy-N-methyl-nicotinamide (0.13 g, 0.68 mmol) in 5 ml of THF was added and the reaction mixture was allowed to warm to RT and stir for 6 hours. Saturated $NH_4Cl$ was added and the mixture was extracted with $CH_2Cl_2$ (3×10 ml). The organic layers were combined, washed with brine, and dried over $NaSO_4$. The solvents were removed in vacuo and the residue was purified by column chromatography (Hex/AcOEt 9:1) to give 130 mg (77%) of an oily product. IR, NMR.

Preparation 150

2-Chloro-5-(1-(2,3-difluorophenyl)-2-N-methylcarbamoylvinyl)pyridine

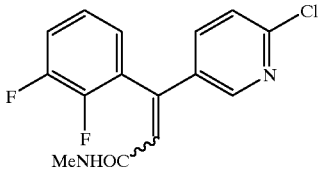

The 2-chloro-5-(2,3-difluorobenzoyl)pyridine was converted to product in a manner substantially analogous to preparation 203 to obtain a mixture of two isomers. After crystallization from EtOAc, the Z isomer was isolated in 35% yield, IR, NMR, while the E isomer was recovered from the filtrate in 17% yield, IR, NMR.

Preparation 151

1-(2-Oxo-2-phenylethyl)-2-chloro-5-[(E)-1-phenyl-2-methylcarbamoylvinyl]pyridinium iodide

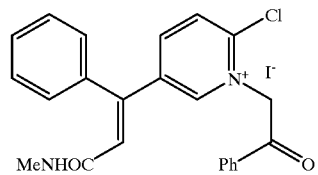

To a mixture of 2-chloro-5-[(E)-1-phenyl-2-N-methylcarbamoylvinyl]pyridine (100 mg, 0.367 mmol) and bromoacetophenone (0.270 g, 1.35 mmol) in 5 ml of $CH_3CN$ was added NaI (0.21 g, 1.4 mmol). The reaction mixture was refluxed for 40 hours. The $CH_3CN$ was removed in vacuo and the resulting residue was dissolved in hot EtOH (40–45° C.). After a rapid filtration, the filtrate was removed in vacuo and the resulting solid was washed with 100 mL of $Et_2O$ then with cold EtOAc to yield product as a solid in 85% yield. IR, NMR.

Preparation 152

1-[2-Oxo-2-(4-fluorophenyl)ethyl]-2-chloro-5-[(E)-1-phenyl-2-methylcarbamoylvinyl]pyridinium iodide

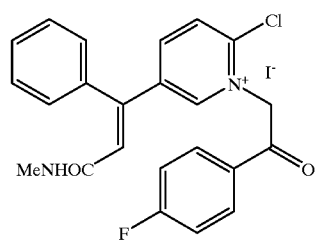

The 2-chloro-5-[(E)-1-phenyl-2-N-methylcarbamoylvinyl]pyridine (300 mg, 1.10 mmol) and 4-fluorobromoacetophenone were converted to product in a manner substantially analogous to Preparation 151 to yield 395 mg. (67%) IR, NMR.

Preparation 153

1-[2-Oxopropyl]-2-chloro-5-[(E)-1-phenyl-2-methylcarbamoylvinyl]pyridinium iodide

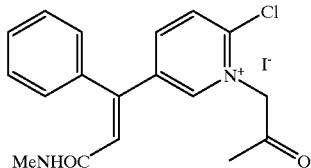

The 2-chloro-5-[(E)-1-phenyl-2-N-methylcarbamoylvinyl]pyridine (300 mg, 1.10 mmol) and chloropropanone were converted to product in a manner substantially analogous to Preparation 151 to yield 297 mg. (60%). NMR.

Preparation 154

1-[2-Oxo-3,3-dimethylbutyl]-2-chloro-5-[(E)-1-phenyl-2-methylcarbamoylvinyl]pyridinium iodide The 2-chloro-5-[(E)-1-phenyl-2-N-methylcarbamoylvinyl]pyridine (300 mg, 1.10 mmol) and chloropinacolone were converted to product in a manner substantially analogous to Preparation 151 to give 141 mg. (26%). IR.

Preparation 155

1-(N,N-diethylacetamidyl)-2-chloro-5-[(E)-1-phenyl-2-methylcarbamoylvinyl]pyridinium iodide

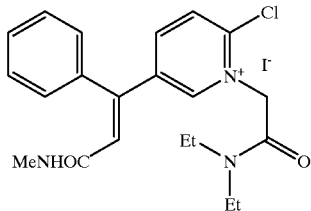

The 2-chloro-5-[(E)-1-phenyl-2-N-methylcarbamoylvinyl]pyridine (140 mg, 0.514 mmol) and 2-chloro-N,N-diethylacetamide were converted to product in a manner substantially analogous to Preparation 151 to give 75.9 mg. (29%). NMR.

Preparation 156

1-[2-Oxo-3,3-dimethylbutyl]-2-chloro-5-[(E)-1-(2,3-difluorophenyl)-2-methylcarbamoylvinyl]pyridinium iodide

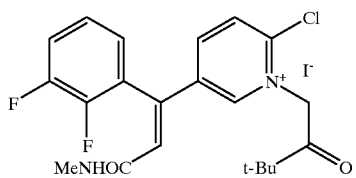

The 2-chloro-5-[(E)-1-(2,3-difluorophenyl)-2-N-methylcarbamoylvinyl]pyridine (250 mg, 0.810 mmol) and chloropinacolone were converted to product in a manner substantially analogous to Preparation 151 to give 199 mg. (46%). IR.

EXAMPLES

Example 1

2-Trifluoroacetamido-3-(2,5-difluorophenyl)-6-benzoyl-imidazo[1,2-a]pyridine

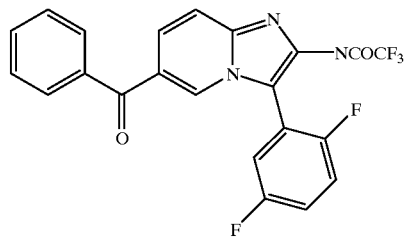

The 1,2-dihydro-2-toluenesulfonylimido-5-benzoyl-N-(1-[2,5-difluorophenyl]-carbamoylmethyl)-pyridine (14.9 g, 28.6 mmol) was dissolved in 400 ml of $CH_2Cl_2$ and trifluoroacetic anhydride (50 ml, 354 mmol) was added. The solution was heated to reflux (a dry ice condenser was used to keep volatiles refluxing) and allowed to stir for 3 hours. The solvents were removed in vacuo and the residue taken up in 700 ml of EtOAc. The solution was washed with saturated $NaHCO_3$ (3×100 ml), brine (3×100 ml), dried over $Na_2SO_4$, filtered, and concentrated in vacuo. The crude product was recrystalized from EtOAc/hexanes to yield 12.1 g. (94.6%). EA, MS(FD).

Example 2

2-Trifluoroacetamido-3-(4-methoxyphenyl)-6-benzoyl-imidazo[1,2-a]pyridine

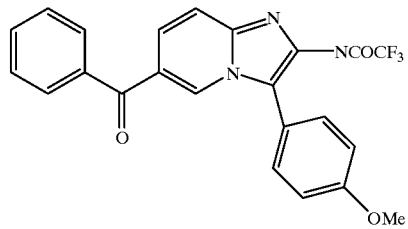

The 1,2-dihydro-2-toluenesulfonylimido-5-benzoyl-N-(1-[4-methoxyphenyl]-carbamoylmethyl)-pyridine (13.2 g, 23.3 mmol) was converted to product in a manner substantially analogous to Example 1 to yield 10.6 g. (92%). EA, MS(FD).

Example 3

2-Trifluoroacetamido-3-(napth-2-yl)-6-benzoyl-imidazo[1,2-a]pyridine

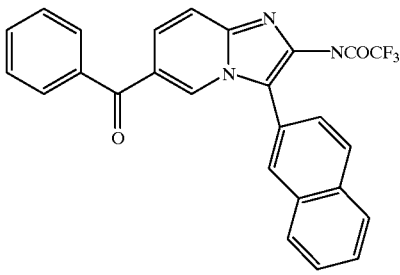

The 1,2-dihydro-2-toluenesulfonylimido-5-benzoyl-N-(1-[napth-2-yl]-carbamoylmethyl)-pyridine (14.7 g, 27.4 mmol) was converted to product in a manner substantially analogous to Example 1 to yield 10.4 g. (82.4%). EA, MS(FD).

Example 4

2-Trifluoroacetamido-3-napthyl-6-benzoyl-imidazo[1,2-a]pyridine

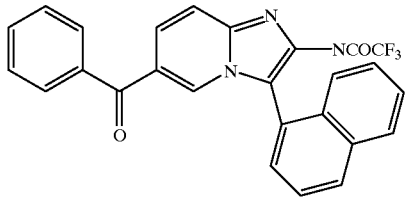

The 1,2-dihydro-2-toluenesulfonylimido-5-benzoyl-N-(1-napthyl-carbamoylmethyl)-pyridine (11.3 g, 22.0 mmol) was converted to product in a manner substantially analogous to Example 1 to yield 8.25 g. (82%). EA, MS(FD).

Example 5

2-Trifluoroacetamido-3-(2-fluorophenyl)-6-benzoyl-imidazo[1,2-a]pyridine

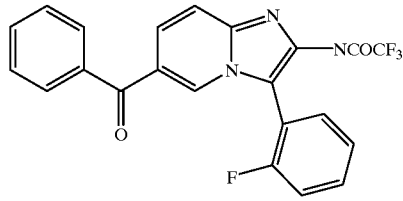

The 1,2-dihydro-2-toluenesulfonylimido-5-benzoyl-N-(1-[2-fluorophenyl]-carbamoylmethyl)-pyridine (12.3 g, 24.5 mmol) was converted to product in a manner substantially analogous to Example 1 to yield 10.2 g. (97%). EA, MS(FD).

Example 6

2-Trifluoroacetamido-3-(3-fluorophenyl)-6-benzoyl-imidazo[1,2-a]pyridine

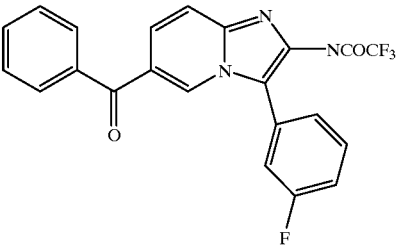

The 1,2-dihydro-2-toluenesulfonylimido-5-benzoyl-N-(1-[3-fluorophenyl]-carbamoylmethyl)-pyridine (26.6 g, 52.8 mmol) was converted to product in a manner substantially analogous to Example 1 to yield 21.6 g. (95.8%). EA, MS(FD).

Example 7

2-Trifluoroacetamido-3-(2,4-difluorophenyl)-6-benzoyl-imidazo[1,2-a]pyridine

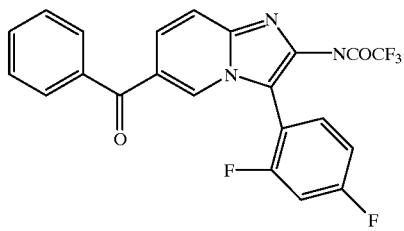

The 1,2-dihydro-2-toluenesulfonylimido-5-benzoyl-N-(1-[2,4-difluorophenyl]-carbamoylmethyl)-pyridine (11.0 g, 21.1 mmol) was converted to product in a manner substantially analogous to Example 1 to yield 9.24 g. (98.5%). EA, MS(FD).

Example 8

2-Trifluoroacetamido-3-(3,5-difluorophenyl)-6-benzoyl-imidazo[1,2-a]pyridine

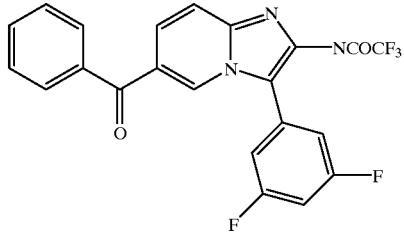

The 1,2-dihydro-2-toluenesulfonylimido-5-benzoyl-N-(1-[3,5-difluorophenyl]-carbamoylmethyl)-pyridine (13.3 g, 25.6 mmol) was converted to product in a manner substantially analogous to Example 1 to yield 10.2 g. (90.1%). EA, MS(FD).

Example 9

2-Trifluoroacetamido-3-(4-fluorophenyl)-6-benzoyl-imidazo[1,2-a]pyridine

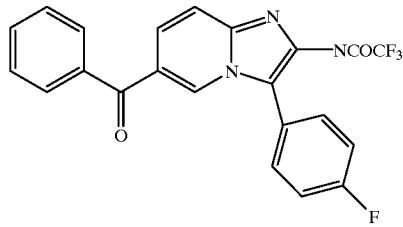

The 1,2-dihydro-2-toluenesulfonylimido-5-benzoyl-N-(1-[4-fluorophenyl]-carbamoylmethyl)-pyridine (35.0 g, 69.6 mmol) was converted to product in a manner substantially analogous to Example 1 to yield 18.6 g. (62.7%). EA, MS(FD).

Example 10

2-Trifluoroacetamido-3-(3-trifluoromethylphenyl)-6-benzoyl-imidazo[1,2-a]pyridine

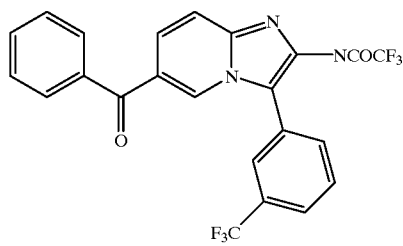

The 1,2-dihydro-2-toluenesulfonylimido-5-benzoyl-N-(1-[3-trifluoromethylphenyl]-carbamoylmethyl)-pyridine (13.3 g, 24.1 mmol) was converted to product in a manner substantially analogous to Example 1 to yield 9.08 g. (80%). EA, MS(FD).

Example 11

2-Trifluoroacetamido-3-(4-bromophenyl)-6-benzoyl-imidazo[1,2-a]pyridine

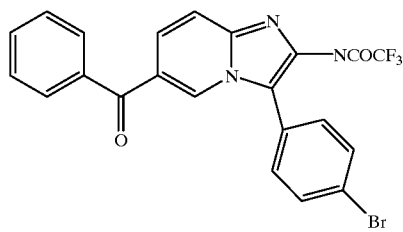

The 1,2-dihydro-2-toluenesulfonylimido-5-benzoyl-N-(1-[4-bromophenyl]-carbamoylmethyl)-pyridine (12.7 g, 22.5 mmol) was converted to product in a manner substantially analogous to Example 1 to yield 10.5 g. (95.4%). EA, MS(FD).

Example 12

2-Trifluoroacetamido-3-(2,3,4-trifluorophenyl)-6-benzoyl-imidazo[1,2-a]pyridine

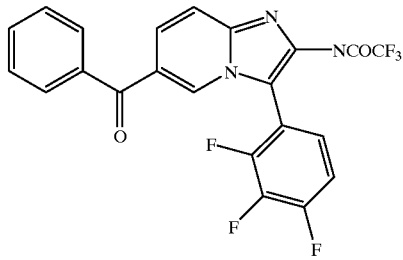

The 1,2-dihydro-2-toluenesulfonylimido-5-benzoyl-N-(1-[2,3,4-trifluorophenyl]-carbamoylmethyl)-pyridine (11.3 g, 20.9 mmol) was converted to product in a manner substantially analogous to Example 1 to yield 8.43 g. (87%). EA, MS(FD).

Example 13

2-Trifluoroacetamido-3-(3,4-difluorophenyl)-6-benzoyl-imidazo[1,2-a]pyridine

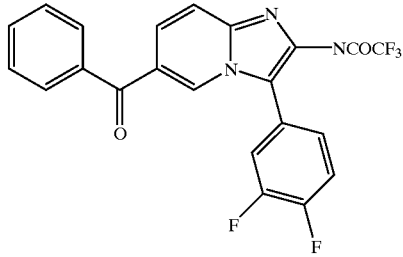

The 1,2-dihydro-2-toluenesulfonylimido-5-benzoyl-N-(1-[3,4-fluorophenyl]-carbamoylmethyl)-pyridine (9.53 g, 18.3 mmol) was converted to product in a manner substantially analogous to Example 1 to yield 7.44 g. (91%). EA, MS(FD).

Example 14

2-Trifluoroacetamido-3-(3,4-dichlorophenyl)-6-benzoyl-imidazo[1,2-a]pyridine

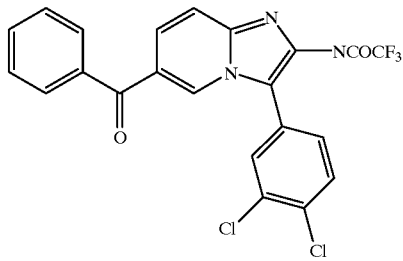

The 1,2-dihydro-2-toluenesulfonylimido-5-benzoyl-N-(1-[3,4-dichlorophenyl]-carbamoylmethyl)-pyridine (13.8 g, 24.9 mmol) was converted to product in a manner substantially analogous to Example 1 to yield 9.91 g. (83%). EA, MS(FAB).

Example 15

2-Trifluoroacetamido-3-(2,4,5-trifluorophenyl)-6-benzoyl-imidazo[1,2-a]pyridine

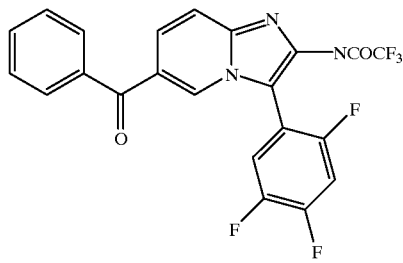

The 1,2-dihydro-2-toluenesulfonylimido-5-benzoyl-N-(1-[2,4,5-trifluorophenyl]-carbamoylmethyl)-pyridine (11.6 g, 21.5 mmol) was converted to product in a manner substantially analogous to Example 1 to yield 9.28 g. (93%). EA, MS(FD).

Example 16

2-Trifluoroacetamido-3-(2-chlorophenyl)-6-benzoyl-imidazo[1,2-a]pyridine

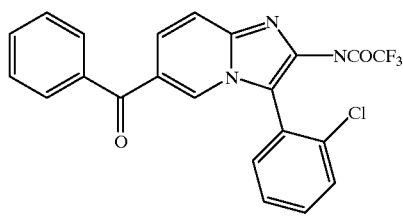

The 1,2-dihydro-2-toluenesulfonylimido-5-benzoyl-N-(1-[2-chlorophenyl]-carbamoylmethyl)-pyridine (14.2 g, 27.3 mmol) was converted to product in a manner substantially analogous to Example 1 to yield 10.8 g. (88%). EA, MS(FD).

Example 17

2-Trifluoroacetamido-3-(3-chlorophenyl)-6-benzoyl-imidazo[1,2-a]pyridine

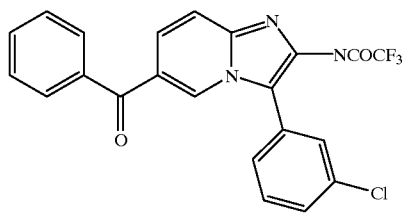

The 1,2-dihydro-2-toluenesulfonylimido-5-benzoyl-N-(1-[3-chlorophenyl]-carbamoylmethyl)-pyridine (12.0 g, 23.1 mmol) was converted to product in a manner substantially analogous to Example 1 to yield 8.97 g. (88%). EA, MS(FD).

Example 18

2-Trifluoroacetamido-3-(4-chlorophenyl)-6-benzoyl-imidazo[1,2-a]pyridine

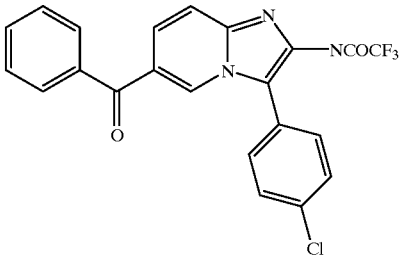

The 1,2-dihydro-2-toluenesulfonylimido-5-benzoyl-N-(1-[4-chlorophenyl]-carbamoylmethyl)-pyridine (13.8 g, 26.5 mmol) was converted to product in a manner substantially analogous to Example 1 to yield 10.7 g. (91%). EA, MS(FD).

Example 19

2-Trifluoroacetamido-3-(4-trifluoromethoxyphenyl)-6-benzoyl-imidazo[1,2-a]pyridine

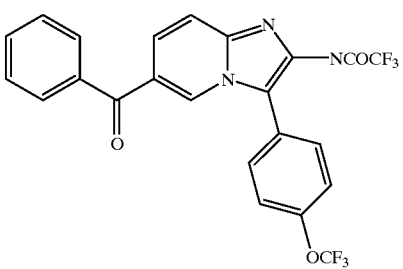

The 1,2-dihydro-2-toluenesulfonylimido-5-benzoyl-N-(1-[4-trifluoromethoxyphenyl]-carbamoylmethyl)-pyridine (13.2 g, 23.3 mmol) was converted to product in a manner substantially analogous to Example 1 to yield 10.6 g. (92%). EA, MS(FD).

Example 20

2-Trifluoroacetamido-3-(3-trifluoromethoxyphenyl)-6-benzoyl-imidazo[1,2-a]pyridine

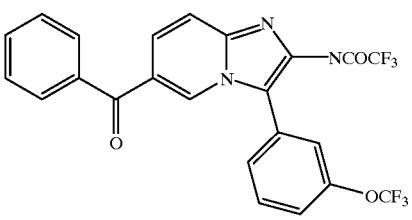

The 1,2-dihydro-2-toluenesulfonylimido-5-benzoyl-N-(1-[3-trifluoromethoxyphenyl]-carbamoylmethyl)-pyridine (12.5 g, 22.0 mmol) was converted to product in a manner substantially analogous to Example 1 to yield 10.4 g. (96%). EA, MS(FD).

Example 21

2-Trifluoroacetamido-3-(2-fluoro-4-trifluoromethylphenyl)-6-benzoyl-imidazo[1,2-a]pyridine

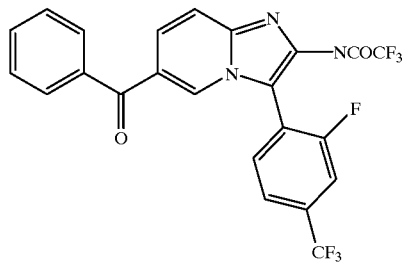

The 1,2-dihydro-2-toluenesulfonylimido-5-benzoyl-N-(1-[2-fluoro-4-trifluoromethylphenyl]-carbamoylmethyl)-pyridine (10.1 g, 17.7 mmol) was converted to product in a manner substantially analogous to Example 1 to yield 8.03 g. (92%). EA, MS(FD).

Example 22

2-Trifluoroacetamido-3-phenyl-6-benzoyl-imidazo[1,2-a]pyridine

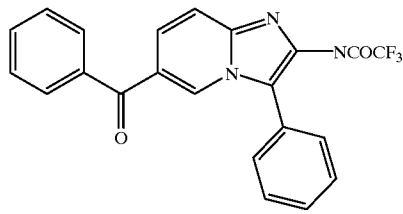

The 1,2-dihydro-2-toluenesulfonylimido-5-benzoyl-N-(1-phenyl-carbamoylmethyl)-pyridine (13.3 g, 27.3 mmol) was converted to product in a manner substantially analogous to Example 1 to yield 10.0 g. (90%). EA, MS(FD).

Example 23

2-Trifluoroacetamido-3-(2,6-difluorophenyl)-6-benzoyl-imidazo[1,2-a]pyridine

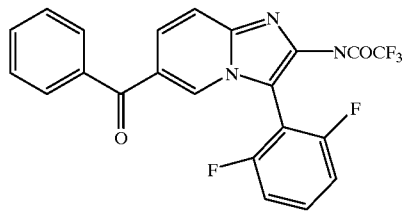

The 1,2-dihydro-2-toluenesulfonylimido-5-benzoyl-N-(1-[2,6-difluorophenyl)-carbamoylmethyl)-pyridine (7.44 g, 14.3 mmol) was converted to product in a manner substantially analogous to Example 1 to yield 5.26 g. (82.8%). EA, MS(FD).

Example 24

2-Trifluoroacetamido-3-(2,3,4,5,6-pentafluorophenyl)-6-benzoyl-imidazo[1,2-a]pyridine

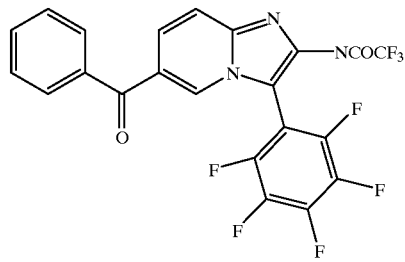

The 1,2-dihydro-2-toluenesulfonylimido-5-benzoyl-N-(1-[2,3,4,5,6-pentafluorophenyl]-carbamoylmethyl)-pyridine (3.00 g, 5.22 mmol) was converted to product in a manner substantially analogous to Example 1 to yield 1.58 g. (60.8%). EA, MS(FD).

Example 25

2-Trifluoroacetamido-3-(2-trifluoromethylphenyl)-6-benzoyl-imidazo[1,2-a]pyridine

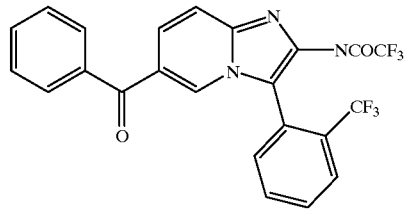

The 1,2-dihydro-2-toluenesulfonylimido-5-benzoyl-N-(1-[2-trifluoromethylphenyl]-carbamoylmethyl)-pyridine (7.37 g, 13.3 mmol) was converted to product in a manner substantially analogous to Example 1 to yield 6.22 g. (98%). EA, MS(FD)

Example 26

2-Trifluoroacetamido-3-(thiophen-3-yl)-6-benzoyl-imidazo[1,2-a]pyridine

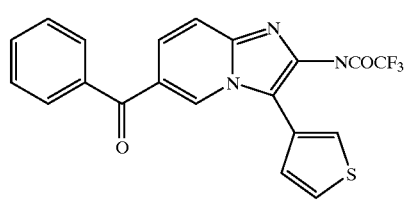

The 1,2-dihydro-2-toluenesulfonylimido-5-benzoyl-N-(1-[thiophen-3-yl]-carbamoylmethyl)-pyridine (11.4 g, 23.1 mmol) was converted to product in a manner substantially analogous to Example 1 to yield 8.88 g. (92.6%). EA, MS(FD).

Example 27

2-Trifluoroacetamido-3-(2-trifluoromethyl-4-fluorophenyl)-6-benzoyl-imidazo[1,2-a]pyridine

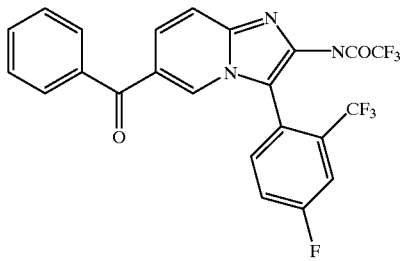

The 1,2-dihydro-2-toluenesulfonylimido-5-benzoyl-N-(1-[2-trifluoromethyl-4-fluorophenyl]-carbamoylmethyl)-pyridine (14.5 g, 25.3 mmol) was converted to product in a manner substantially analogous to Example 1 to yield 11.0 g. (88%). EA, MS(FD).

Example 28

2-Trifluoroacetamido-3-(2-fluoro-6-trifluoromethylphenyl)-6-benzoyl-imidazo[1,2-a]pyridine

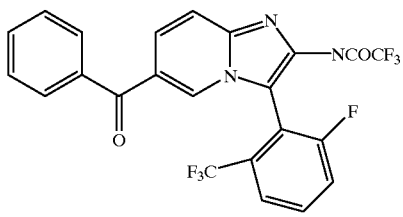

The 1,2-dihydro-2-toluenesulfonylimido-5-benzoyl-N-(1-[2-fluoro-6-trifluoromethylphenyl]-carbamoylmethyl)-pyridine (2.90 g, 5.08 mmol) was converted to product in a manner substantially analogous to Example 1 to yield 2.37 g. (94%). EA, MS(FD).

Example 29

2-Trifluoroacetamido-3-(4-trifluoromethylphenyl)-6-benzoyl-imidazo[1,2-a]pyridine

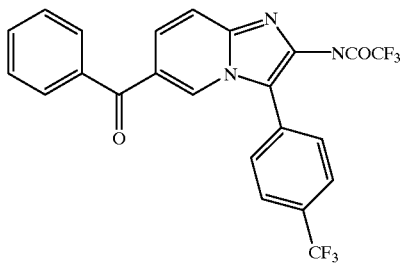

The 1,2-dihydro-2-toluenesulfonylimido-5-benzoyl-N-(1-[4-trifluoromethylphenyl]-carbamoylmethyl)-pyridine (13.3 g, 24.1 mmol) was converted to product in a manner substantially analogous to Example 1 to yield 10.1 g. (88.1%). EA, MS(FD).

Example 30

2-Trifluoroacetamido-3-(2-methoxyphenyl)-6-benzoyl-imidazo[1,2-a]pyridine

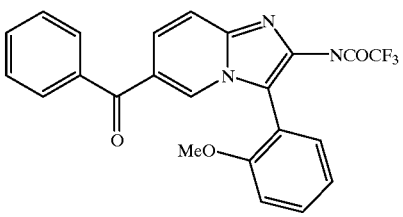

The 1,2-dihydro-2-toluenesulfonylimido-5-benzoyl-N-(1-[2-methoxyphenyl]-carbamoylmethyl)-pyridine (10.4 g, 20.3 mmol) was converted to product in a manner substantially analogous to Example 1 to yield 7.40 g. (83%). EA, MS(FD).

Example 31

2-Trifluoroacetamido-3-(4-carbomethoxyphenyl)-6-benzoyl-imidazo[1,2-a]pyridine

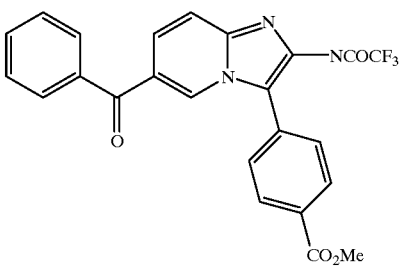

The 1,2-dihydro-2-toluenesulfonylimido-5-benzoyl-N-(1-[2-methoxyphenyl]-carbamoylmethyl)-pyridine (15.5 g, 28.5 mmol) was converted to product in a manner substantially analogous to Example 1 to yield 12.6 g. (94.5%). EA, MS(FD).

Example 32

2-Trifluoroacetamido-3-(4-nitrophenyl)-6-benzoyl-imidazo[1,2-a]pyridine

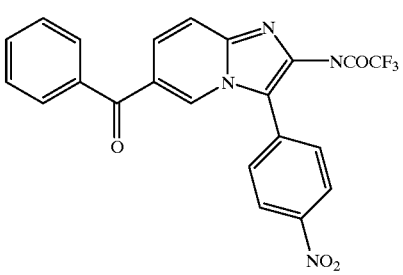

The 1,2-dihydro-2-toluenesulfonylimido-5-benzoyl-N-(1-[2-methoxyphenyl]-carbamoylmethyl)-pyridine (15.3 g, 28.9 mmol) was converted to product in a manner substantially analogous to Example 1 to yield 11.2 g. (85.1%). EA, MS(FD).

Example 33

2-Trifluoroacetamido-3-benzyl-6-benzoyl-imidazo[1,2-a]pyridine

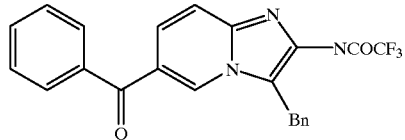

The 1,2-dihydro-2-toluenesulfonylimido-5-benzoyl-N-(1-benzyl-carbamoylmethyl)-pyridine (3.44 g, 6.89 mmol) was converted to product in a manner substantially analogous to Example 1 to yield 2.19 g. (74.0%). EA, MS(FD).

Example 34

2-Trifluoroacetamido-3-isobutyl-6-benzoyl-imidazo[1,2-a]pyridine

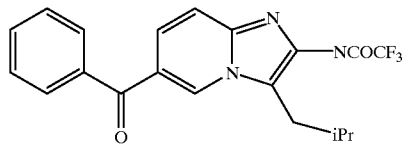

The 1,2-dihydro-2-toluenesulfonylimido-5-benzoyl-N-(1-isobutyl-carbamoylmethyl)-pyridine (3.30 g, 7.09 mmol) was converted to product in a manner substantially analogous to Example 1 to yield 2.37 g. (85.9%). EA, MS(FD).

Example 35

2-Trifluoroacetamido-3-(4-fluorophenyl)-6-(4-fluorobenzoyl)-imidazo[1,2-a]pyridine

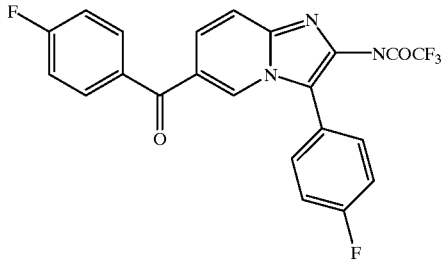

The 1,2-dihydro-2-toluenesulfonylimido-5-(4-fluorobenzoyl)-N-(1-[4-fluorophenyl]-carbamoylmethyl)-pyridine (9.15 g, 17.6 mmol) was converted to product in a manner substantially analogous to Example 1 to yield 7.11 g. (91%). EA, MS(FD).

Example 36

2-Trifluoroacetamido-3-fluoro-4-trifluoromethylphenyl)-6-(4-fluorobenzoyl)-imidazo[1,2-a]pyridine

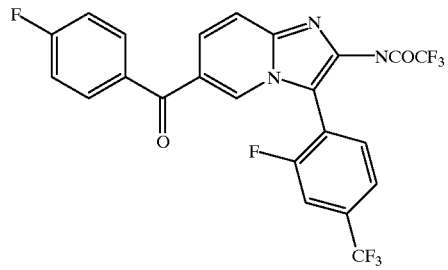

The 1,2-dihydro-2-toluenesulfonylimido-5-(4-fluorobenzoyl)-N-(1-[2-fluoro-4-trifluoromethylphenyl]-carbamoylmethyl)-pyridine (8.95 g, 15.2 mmol) was converted to product in a manner substantially analogous to Example 1 to yield 6.75 g. (87%). EA, MS(FD).

Example 37

2-Trifluoroacetamido-6-benzoyl-imidazo[1,2-a]pyridine

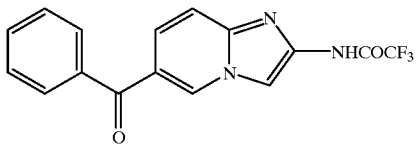

To a suspension of 1-carbamoylmethyl-1,2-dihydro-2-toluenesulfonimido-6-benzoylpyridine (7.15 g, 17.46 mmol) in 85 ml of dry $CH_2Cl_2$ was added trifluoroacetic anhydride (62 ml, 439 mmol). The mixture was stirred for 2.5 hours at 30° C. under an argon atmosphere. The solvents were removed in vacuo and the foam was taken-up in EtOAc (600 ml), then washed with $NaHCO_3$ (2×250 ml) and brine (1×250 ml). The organic layer was dried ($Na_2SO_4$) and the solvents were removed in vacuo to afford 5.5 g (92%) of product as a white solid. EIMS, NMR.

Example 38

2-Trifluoroacetamido-3-iodo-6-benzoyl-imidazo[1,2-a]pyridine

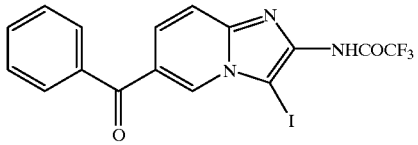

To a solution of 2-trifluoroacetamido-6-benzoyl-imidazo[1,2-a]pyridine (2.0 g, 6.0 mmol) in 50 ml of dry $CH_3CN$ cooled at 0° C., was added N-iodosuccinimide (1.35 g, 6.0 mmol) portionwise. The mixture was stirred for 10 minutes. Acetonitrile was removed in vacuo and the residue was dissolved in EtOAc (250 ml), washed with $NaHSO_3$ (40% p/v, 2×200 ml) and $NaHCO_3$ (2×200 ml). The organic layer was dried (Na$_2$SO$_4$) and EtOAc was removed in vacuo to afford 2.60 g (95%) of product as a yellow solid. EIMS, NMR.

Example 39

2-Trifluoroacetamido-3-methylthio-6-benzoyl-imidazo[1,2-a]pyridine

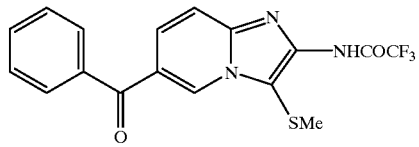

The 2-trifluoroacetamido-3-iodo-6-benzoyl-imidazo[1,2-a]pyridine (1.00 g, 2.17 mmol) was dissolved in 20 ml of pyridine (predried over KOH and then molecular sieve 3A, 0.04% H$_2$O) under argon atmosphere. Copper bronze (207 mg, 3.25 mmol) was added. To the golden suspension in brown solution was added methyldisulfide (160 μl, 2.17 mmol) via syringe. The reaction mixture was heated for 1 hour at 104° C. then 68 hours at 100° C. The evolution of the reaction was followed by NMR (in each case, a sample was taken, hydrolized and washed with ammonia/NH$_4$Cl (1:9) before checking by NMR). When the reaction was complete, the reaction mixture was diluted in 3 L of EtOAc and stirred for 15 minutes. Two liters of NH$_4$OH/NH$_4$Cl 1:9 were added and the mixture was strongly stirred for 30 minutes in a 10 L funnel. The layers were separated and 2 L of NH$_4$OH/NH$_4$Cl (1:9) were added to the organic layer. The mixture was again stirred for 30 minutes and then left without stirring for 5 to 10 minutes. The layers were separated and the organic layer was washed with brine. The organic layers were removed in vacuo and the resulting brown solid was subjected to a vary rapid column chromatography (MeOH/CH$_2$Cl$_2$, 2:98) to give 670 mg (81%) of a yellow solid. NMR

Example 40

2-Trifluoroacetamido-3-methylsulfonyl-6-benzoyl-imidazo[1,2-a]pyridine

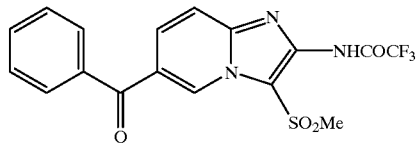

The 2-trifluoroacetamido-3-methylthio-6-benzoyl-imidazo[1,2-a]pyridine (500 mg, 1.37 mmol) was mixed with mCPBA (563 mg, 2.62 mmol) in 20 ml of dry CH$_2$Cl$_2$. The reaction mixture was stirred for 3 hours at 0° C. and then washed with 1 ml of saturated NaHCO$_3$. The mixture was filtered through celite and washed with EtOAc. The filtrate was removed in vacuo and the residue was purified by column chromatography to yield 385 mg (67%) of a white yellow solid. NMR.

Example 41

2-Trifluoroacetamido-3-isopropylthio-6-benzoyl-imidazo[1,2-a]pyridine

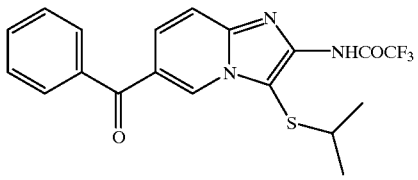

The 2-trifluoroacetamido-3-iodo-6-benzoyl-imidazo[1,2-a]pyridine (100 mg, 0.22 mmol) was dissolved in dry pyridine (10 ml) at RT under an argon atmosphere. Copper bronze (21 mg, 0.33 mmol) was added followed by diisopropyl disulfide (35 μl, 0.22 mmol). The mixture was stirred and heated at 100–102° C. for 83 hours. The reaction was cooled to RT, poured onto 1 L of EtOAc and stirred for 1 hour. A 9:1 solution of NH$_4$Cl/NH$_4$OH (750 ml) was then added and the mixture stirred for 15 minutes with a mechanical stirrer. The aqueous layer turned light-blue and the organic extract was washed again with 750 ml of the 9:1 NH$_4$Cl/NH$_4$OH solution (15 minutes) followed by brine (750 ml). The EtOAc was removed in vacuo and the residue was purified by flash chromatography (EtOAc:Hexane 1:1). The product was obtained as a brown oil in 20% yield (18 mg). $^1$H-NMR, $^{13}$C-NMR.

Example 42

2-Trifluoroacetamido-6-[(E)-1-phenyl-2-N-methylcarbamoylvinyl]-imidazo[1,2-a]pyridine

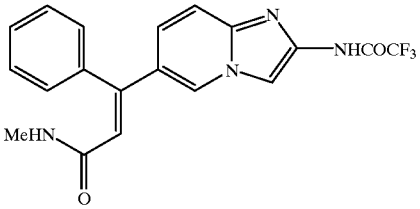

The diethyl-(N-methylcarbamoylmethyl)phosphonate (1.88 g, 9.00 mmol) and 250 mL of dry THF were placed in a flame dried flask under an argon atmosphere. The solution was cooled to −78° C. before the dropwise addition of potassium hexamethyldisilazide (30 mL, 22.5 mmol; 0.5M in toluene). The mixture was stirred for 2 hours at −78° C. A solution of 2-trifluoroacetamido-6-benzoyl-imidazo[1,2-a] pyridine (2.00 g, 6.00 mmol) in 100 mL of dry THF was added dropwise. The reaction mixture was stirred at −78° C. for 2 hours and then allowed to warm to room temperature. The resulting brown solution was stirred at RT for 60 hours. The THF was removed in vacuo and the residue was taken up in 400 mL of EtOAc and washed with saturated NH$_4$Cl (2×100 ml) and once with brine. After drying over MgSO$_4$, the solvents were removed in vacuo to give a brown solid. NMR analysis of the crude showed only the somer along with some other side products that were not identified. The crude was purified by column chromatography CH$_3$CN:CH$_2$Cl$_2$ (2:1) to give 920 mg (40%) of product. EIMS, NMR.

Example 43

2-Trifluoroacetamido-3-iodo-6-[(E)-1-phenyl-2-N-methylcarbamoylvinyl]-imidazo[1,2-a]pyridine

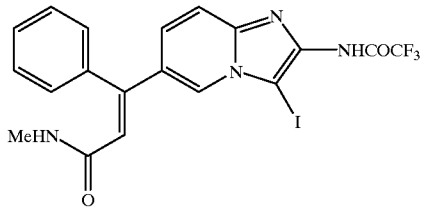

To a solution of 2-trifluoroacetamido-6-[(E)-2-N-methylcarbamoyl-1-phenylvinyl]-imidazo[1,2-a]pyridine (423 mg, 1.22 mmol) in 20 ml of dry $CH_3CN$ cooled at 0° C., was added N-iodosuccinimide (1,34 mmol, 302 mg) portionwise and the mixture was stirred for 10 minutes. The desired product precipitates as a white solid which is filtered and air-dried affording 375 mg of crude product. The $CH_3CN$ was removed in vacuo and the residue dissolved in EtOAc (50 ml). The EtOAc was washed with $NaHSO_3$ (40%) (2×50 ml) and $NaHCO_3$ (2×50 ml). The organic layer was dried ($Na_2SO_4$) and the EtOAc removed in vacuo, affording 240 mg (98% overall yield) of product as a white solid. EIMS, NMR.

Example 44

2-Trifluoroacetamido-3-isopropylsulfonyl-6-[(E)-1-phenyl-2-N-methylcarbamoylvinyl]-imidazo1,2-a]pyridine

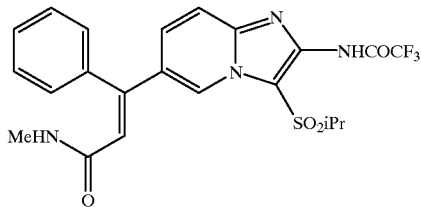

To a solution of 2-trifluoroacetamido-3-iodo-6-[(E)-2-N-methylcarbamoyl-1-phenylvinyl]-imidazo[1,2-a]pyridine (70 mg, 0.15 mmol) in 5 ml of THF cooled to −78° C. was added phenyl lithium (230 μl, 0.33 mmol) under an argon atmosphere. The reaction mixture was stirred for 3 minutes before injecting t-butyl lithium (310 μl, 0.38 mmol). After stirring for a 10 minute period, a solution of isopropyl isopropanethiol-sulfonate (109 mg, 0.60 mmol) in 5 ml of THF was added. The reaction mixture was stirred for 30 minutes at −78° C. and then quenched with 2 drops of $H_2O$ and 10 ml of THF. Ethyl acetate (15 ml) was added and the mixture was allowed to warm to RT. The solution was filtered through celite and the solvents were removed in vacuo. The residue was then dissolved in dry $CH_2Cl_2$ (10 ml) and cooled to 0° C. Previously dried mCPBA (208 mg, 5 equiv. excess calculated over 100% theoretical yield of sulfide coupling product) dissolved in $CH_2Cl_2$ (40 ml) was then added dropwise until the starting material was completely converted to the sulfone (monitor by TLC). The solution was then washed with $Na_2SO_3$ (50 ml) and $NaHCO_3$ (2×50 ml). The organics were dried ($Na_2SO_4$) and the solvent removed in vacuo. The residue was purified by flash chromatography in silica gel ($CH_3CN:CH_2Cl_2$ 1:1) to give 47 mg of product as a white solid. (63%). NMR.

Example 45

2-Trifluoroacetamido-6-(2,3-difluorobenzoyl)-imidazo[1,2-a]pyridine

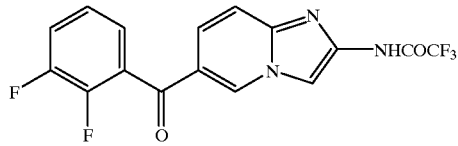

To a solution of 1-bromo-2,3-difluorobenzene (480 ml, 4.32 mmol) in THF was added n-butyl lithium (2.05 ml, 4.42 mmol) in 10 ml of dry THF at −78° C. under an argon atmosphere. After 10 minutes stirring, a solution of 2-trifluoroacetamido-6-(N-methoxy-N-methylamido)-imidazo[1,2-a]pyridine (513 mg, 1.88 mmol) in THF (15 ml) was added dropwise. The reaction mixture was stirred at −78° C. for 1 hour. $NH_4Cl$ was then added and the reaction was extracted with EtOAc (25 ml) and washed with $NH_4Cl$ (2×20 ml). The solvents were removed in vacuo and the residue was purified by flash chromatography on silica gel ($CH_2Cl_2:CH_3CN$ 2.5:1) affording 395 mg of product as a white solid. (57%). EIMS, NMR.

Example 46

2-Trifluoroacetamido-6-[(E)-1-(2,3-difluorophenyl)-2-N-methylcarbamoylvinyl]-imidazo [1,2-a]pyridine

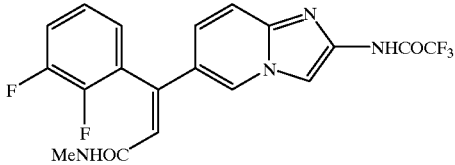

The 2-trifluoroacetamido-6-(2,3-difluorobenzoyl)-imidazo[1,2-a]pyridine (0.454 g, 1.27 mmol) was converted to product in a manner substantially analogous to Preparation 183 to yield 120 mg. (23%). $^1$H-NMR, $^{13}$C-NMR.

Example 47

2-Trifluoroacetamido-3-iodo-6-[(E)-1-(2,3-a] pyridine

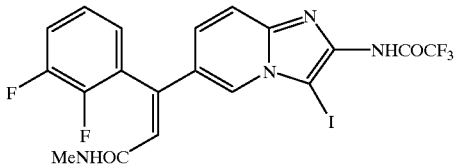

To a solution of 2-trifluoroacetamido-6-[(E)-1-(2,3-difluorophenyl)-2-N-methylcarbamoylvinyl]-imidazo[1,2- a]pyridine (116 mg, 0.27 mmol) in 10 ml of dry CH₃CN cooled at 0° C., was added N-iodosuccinimide (67 mg, 0.30 mmol) portionwise. The reaction mixture was stirred for 15 minutes. The solvent was removed in vacuo, the residue was dissolved in EtOAc (25 ml), washed with NaHSO₃ (40% p/v, 2×25 ml), and then with NaHCO₃ (2×25 ml). The organic layer was dried (Na₂SO₄) and the EtOAc removed in vacuo, affording 130 mg (86%) of product. ¹H-NMR, ¹³C-NMR.

Example 48

2-Trifluoroacetamido-3-phenyl-6-(2,3-difluorobenzoyl)-imidazo[1,2-a]pyridine

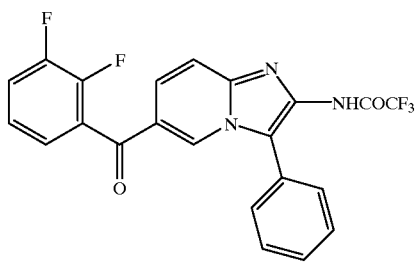

To a solution of 2,3-difluorobromobenzene (471 ml, 4.206 mmol) in dry THF (20 mL) was added a solution of n-butyl lithium (1.6M in hexanes, 2.63 mL) at −78° C. The resulting yellow solution was stirred at the same temperature for 70 minutes, then a solution of 2-trifluoroacetamido-3-phenyl-6-(N-methyl-N-methoxycarbamoyl)imidazo[1,2-a]pyridine (0.500 g, 1.28 mmol) in dry THF (20 mL), was added dropwise via a cannula. The red-orange solution was allowed to warm over 60 minutes. Saturated NH₄Cl was added and the mixture was stirred for 25 minutes before extracting with EtOAc. The organic layer was washed with brine, dried (Na₂SO₄), concentrated in vacuo and purified by column chromatography (CH₂Cl₂/CH₃CN 4/1) to give 390 mg of an orange solid. (69%). MS(FAB), NMR.

Example 49

2-Trifluoroacetamido-3-phenyl-6-[(E)-1-(2,3-difluorophenyl)-2-methylcarbamoylvinyl]-imidazo[1,2-a]pyridine

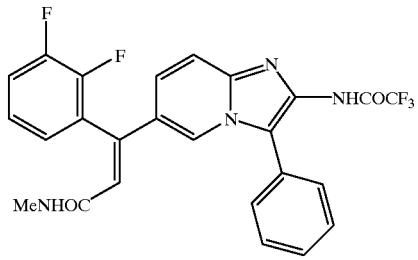

The diethyl-(N-methylcarbamoylmethyl)phosphonate (217 mg, 1.04 mmol) in 250 mL of dry THF was placed in a flame dried flask under an argon atmosphere. The solution was cooled to −78° C. before the dropwise addition of potassium hexamethyldisilazide (5.13 mL, 2.56 mmol; 0.5 M in toluene). The mixture was stirred for 2 hours at −78° C. A solution of the 2-trifluoroacetamido-3-phenyl-6 -(2,3-difluorobenzoyl)-imidazo[1,2-a]pyridine (300 mg, 0.693 mmol) in 100 mL of dry THF was added dropwise. The reaction mixture was stirred at −78° C. for 2 hours and then allowed to warm to RT. The resulting brown solution was stirred at RT for 48 hours (as it is noted a high amount of sovent was required in order to avoid dealing with heterogenous medium once the reagents were mixed). The THF was removed in vacuo and the mixture was diluted in 400 mL of EtOAc and washed with saturated NH₄Cl (2×100 mL) and once with brine. After drying over MgSO₄, the solvents were removed in vacuo to give a brown solid. The residue was purified by column chromatography (CH₃CN:CH₂Cl₂, 2:1) to give 57.6 mg of product. (22%). ¹H NMR, ¹³C NMR.

Example 50

2-Trifluoroacetamido-3-phenyl-6-[(E)-1-phenyl-2-N-methylcarbamoylvinyl]-imidazo[1,2-a]pyridine

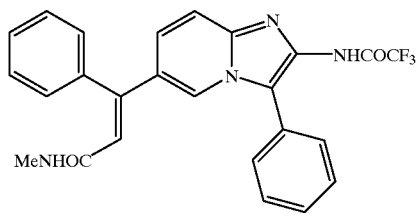

The 2-trifluoroacetamido-3-phenyl-6-benzoyl-imidazo[1, 2-a]pyridine (618 mg, 1.27 mmol) was converted to product in a manner substantially analogous to Example 49 to yield 526 mg. (75%). EIMS, NMR.

Example 51

2-Trifluoroacetamido-3-(2,5-difluorophenyl)-6-[(E)-1-phenyl-2-N-methylcarbamoylvinyl]-imidazo[1,2-a]pyridine

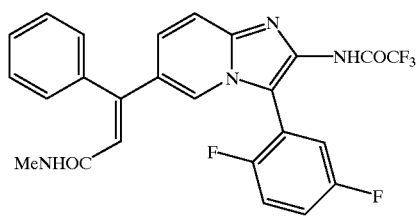

The 2-trifluoroacetamido-3-(2,5-difluorophenyl)-6-benzoylimidazo[1,2-a]pyridine (500 mg, 1.15 mmol) was converted to product in a manner substantially analogous to Example 49 to give 483 mg. (86%). EIMS, NMR.

Example 52

2-Trifluoroacetamido-3-(2-trifluoromethyl-4-fluorophenyl)-6-[(E)-1-phenyl-2-N-methylcarbamoylvinyl]-imidazo[1,2-a]pyridine

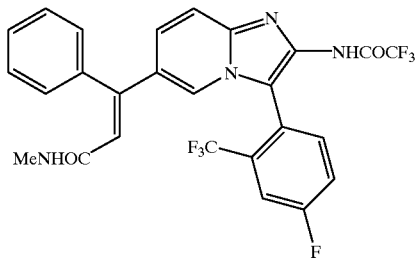

The 2-trifluoroacetamido-3-(2-trifluoromethyl-4-fluorophenyl)-6-benzoylimidazo[1,2-a]pyridine (500 mg, 1.04 mmol) was converted to product in a manner substantially analogous to Example 49 to give 439 mg. (79%). EIMS, NMR.

Example 53

2-Trifluoroacetamido-3-(2,3,4-trifluorophenyl)-6-[(E)-1-phenyl-2-N-methylcarbamoylvinyl]-imidazo[1,2-a]pyridine

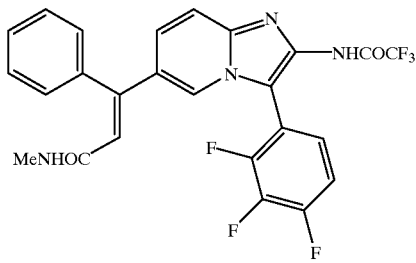

The 2-trifluoroacetamido-3-(2,3,4-trifluorophenyl)-6-benzoylimidazo[1,2-a]pyridine (303 mg, 0.672 mmol) was converted to product in a manner substantially analogous to Example 49 to give 168 mg. (50%). NMR.

Example 54

2-Trifluoroacetamido-3-(3,5-difluorophenyl)-6-[(E)-1-phenyl-2-N-methylcarbamoylvinyl]-imidazo[1,2-a]pyridine

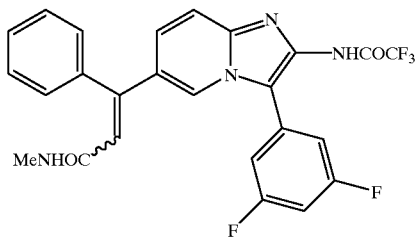

The 2-trifluoroacetamido-3-(3,5-difluorophenyl)-6-benzoylimidazo[1,2-a]pyridine (240 mg, 0.554 mmol) was converted to product in a manner substantially analogous to Example 49 to give 161 mg of two isomers E:Z in 1:1 ratio. Yield: 60%. EIMS, NMR.

Example 55

2-Trifluoroacetamido-3-(3-trifluoromethylphenyl)-6-[(E)-1-phenyl-2-N-methylcarbamoylvinyl]-imidazo[1,2-a]pyridine

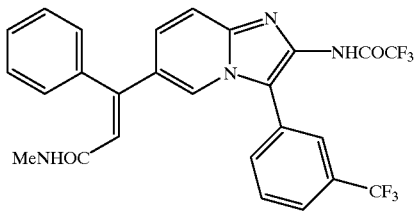

The 2-trifluoroacetamido-3-(3-trifluoromethylphenyl)-6-benzoylimidazo[1,2-a]pyridine (228 mg, 0.491 mmol) was converted to product in a manner substantially analogous to Example 49 to give 228 mg. (57%). EIMS, NMR.

Example 56

2-Amino-3-(2,4-difluorophenyl)-6-benzoyl-imidazo[1,2-a]pyridine

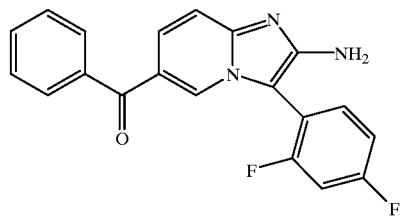

The 2-trifluoroacetamido-3-(2,4-difluorophenyl)-6-benzoyl-imidazo[1,2-a]pyridine (9.24 g, 20.8 mmol) was dissolved in 250 ml of MeOH and 170 ml of 1N NaOH. The solution was stirred at RT under $N_2$ for 2 weeks. The precipitant was filtered and the filter cake was dissolved in 900 ml of EtOAc. The solution was washed with brine (3×50 ml), dried over $Na_2SO_4$, filtered, and concentrated in vacuo. The residue was recrystalized from EtOAc/hexane to give 2 crops yielding 5.57 g. (76.8%). EA, MS(FD).

Example 57

2-Amino-3-(3,5-difluorophenyl)-6-benzoyl-imidazo[1,2-a]pyridine

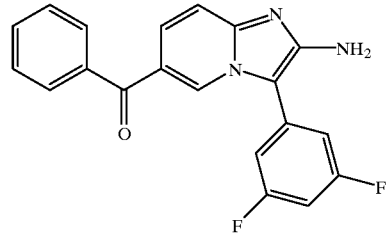

The 2-trifluoroacetamido-3-(3,5-difluorophenyl)-6-benzoyl-imidazo[1,2-a]pyridine (10.2 g, 22.9 mmol) was converted to product in a manner substantially analogous to Example 56 to yield 4.93 g. (61.6%). EA, MS(FD).

Example 58

2-Amino-3-(napth-2-yl)-6-benzoyl-imidazo[1,2-a]pyridine

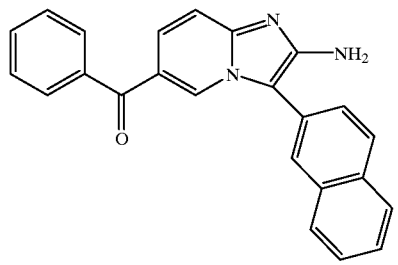

The 2-trifluoroacetamido-3-(napth-2-yl)-6-benzoyl-imidazo[1,2-a]pyridine (6.05 g, 13.7 mmol) was converted to product in a manner substantially analogous to Example 56 to yield 3.50 g. (70.4%). MS(FD), NMR.

Example 59

2-Amino-3-napthyl-6-benzoyl-imidazo[1,2-a]pyridine

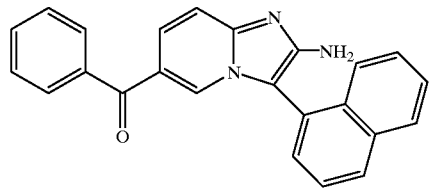

The 2-trifluoroacetamido-3-napthyl-6-benzoyl-imidazo[1,2-a]pyridine (8.25 g, 18.0 mmol) was converted to product in a manner substantially analogous to Example 56 to yield 4.73 g. (73%). EA, MS(FD).

Example 60

2-Amino-3-(2,5-difluorophenyl)-6-benzoyl-imidazo[1,2-a]pyridine

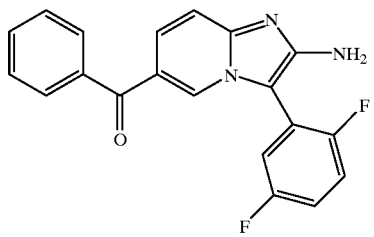

The 2-trifluoroacetamido-3-(2,5-difluorophenyl)-6-benzoyl-imidazo[1,2-a]pyridine (12.1 g, 27.1 mmol) was converted to product in a manner substantially analogous to Example 56 to yield 6.10 g. (64.6%) EA, MS (FD).

Example 61

2-Amino-3-(2,6-difluorophenyl)-6-benzoyl-imidazo[1,2-a]pyridine

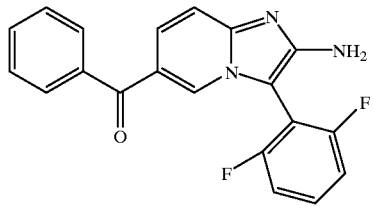

The 2-trifluoroacetamido-3-(2,6-difluorophenyl)-6-benzoyl-imidazo[1,2-a]pyridine (6.01 g, 13.5 mmol) was converted to product in a manner substantially analogous to Example 56 to yield 3.42 9. (72.6%). EA, MS(FD).

Example 62

2-Amino-3-(4-trifluoromethylphenyl)-6-benzoyl-imidazo[1,2-a]pyridine

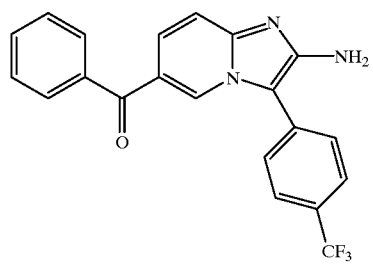

The 2-trifluoroacetamido-3-(4-trifluoromethylphenyl)-6-benzoyl-imidazo[1,2-a]pyridine (10.1 g, 21.2 mmol) was converted to product in a manner substantially analogous to Example 56 to yield 4.43 g. (54.8%). EA, MS(FD).

Example 63

2-Amino-3-(2-fluorophenyl)-6-benzoyl-imidazo[1,2-a]pyridine

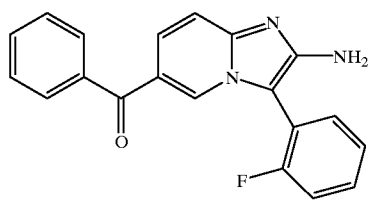

The 2-trifluoroacetamido-3-(2-fluorophenyl)-6-benzoyl-imidazo[1,2-a]pyridine (9.46 g, 22.2 mmol) was converted to product in a manner substantially analogous to Example 56 to yield 6.70 g. (91.4%). EA, MS(FD).

Example 64

2-Amino-3-(3-fluorophenyl)-6-benzoyl-imidazo[1,2-a]pyridine

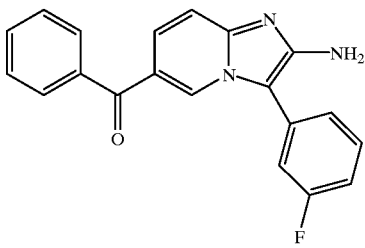

The 2-trifluoroacetamido-3-(3-fluorophenyl)-6-benzoyl-imidazo[1,2-a]pyridine (14.3 g, 33.6 mmol) was converted to product in a manner substantially analogous to Example 56 to yield 8.30 g. (74.7%). EA, MS(FD).

Example 65

2-Amino-3-(4-fluorophenyl)-6-benzoyl-imidazo[1,2-a]pyridine

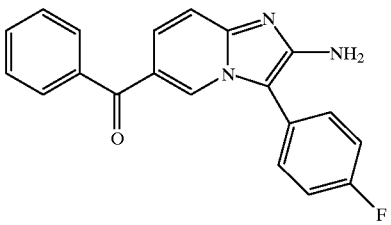

The 2-trifluoroacetamido-3-(4-fluorophenyl)-6-benzoyl-imidazo[1,2-a]pyridine (18.6 g, 43.7 mmol) was converted to product in a manner substantially analogous to Example 56 to yield 11.2 g. (77.2%). EA, MS(FD).

Example 66

2-Amino-3-benzyl-6-benzoyl-imidazo[1,2-a]pyridine

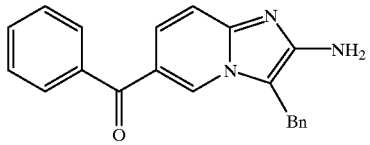

The 2-trifluoroacetamido-3-benzyl-6-benzoyl-imidazo[1,2-a]pyridine (2.14 g, 5.06 mmol) was converted to product in a manner substantially analogous to Example 56 to yield 1.29 g. (78.2%). EA, MS(FD).

Example 67

2-Amino-3-(3-trifluoromethylphenyl)-6-benzoyl-imidazo[1,2-a]pyridine

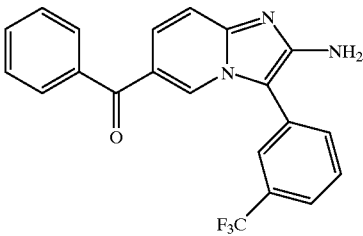

The 2-trifluoroacetamido-3-(3-trifluoromethylphenyl)-6-benzoyl-imidazo[1,2-a]pyridine (9.39 g, 19.7 mmol) was dissolved in 200 ml of MeOH and diisopropylethylamine (100 ml, 574 mmol) was added. The solution was heated to reflux and then stirred at reflux under $N_2$ for 2 days. The solution was concentrated in vacuo and the residue recrystalized from EtOAc/hexane to yield 6.59 g of product. (87.9%). EA, MS(FD).

Example 68

2-Amino-3-(4-methoxyphenyl)-6-benzoyl-imidazo[1,2-a]pyridine

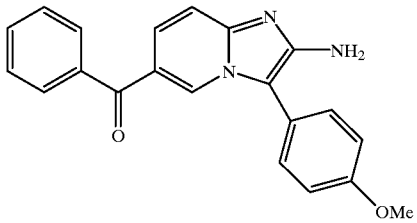

The 2-trifluoroacetamido-3-(4-methoxyphenyl)-6-benzoyl-imidazo[1,2-a]pyridine (4.89 g, 11.1 mmol) was converted to product in a manner substantially analogous to Example 67 to yield 3.08 g. (80%). EA, MS(FD).

Example 69

2-Amino-3-(4-bromophenyl)-6-benzoyl-imidazo[1,2-a]pyridine

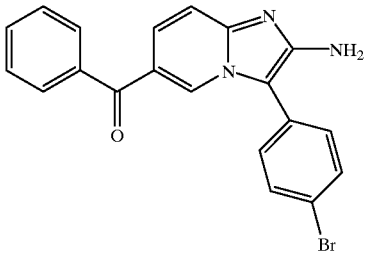

The 2-trifluoroacetamido-3-(4-bromophenyl)-6-benzoyl-imidazo[1,2-a]pyridine (3.00 g, 6.15 mmol) was converted to product in a manner substantially analogous to Example 67 to yield 1.80 g. (75%). EA, MS(FD).

Example 70

2-Amino-3-(2,3,4-trifluorophenyl)-6-benzoyl-imidazo[1,2-a]pyridine

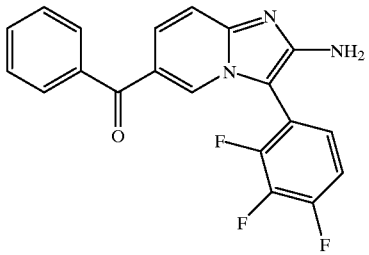

The 2-trifluoroacetamido-3-(2,3,4-trifluorophenyl)-6-benzoyl-imidazo[1,2-a]pyridine (8.43 g, 18.2 mmol) was converted to product in a manner substantially analogous to Example 67 to yield 5.82 g. (87%). EA, MS(FD).

Example 71

2-Amino-3-(3,4-difluorophenyl)-6-benzoyl-imidazo[1,2-a]pyridine

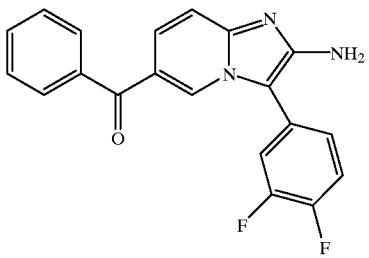

The 2-trifluoroacetamido-3-(3,4-difluorophenyl)-6-benzoyl-imidazo[1,2-a]pyridine (7.44 g, 16.7 mmol) was converted to product in a manner substantially analogous to Example 67 to yield 5.09 g. (87.2%). EA, MS(FD).

Example 72

2-Amino-3-(3,4-dichlorophenyl)-6-benzoyl-imidazo[1,2-a]pyridine

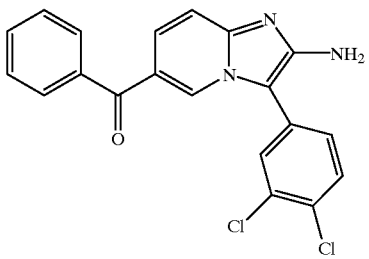

The 2-trifluoroacetamido-3-(3,4-dichlorophenyl)-6-benzoyl-imidazo[1,2-a]pyridine (9.91 g, 20.8 mmol) was converted to product in a manner substantially analogous to Example 67 to yield 7.17 g. (90.4%). EA, MS(FD).

Example 73

2-Amino-3-(2,4,5-trifluorophenyl)-6-benzoyl-imidazo[1,2-a]pyridine

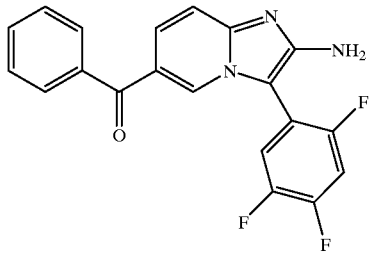

The 2-trifluoroacetamido-3-(2,4,5-triifluorophenyl)-6-benzoyl-imidazo[1,2-a]pyridine (9.28 g, 20.0 mmol) was converted to product in a manner substantially analogous to Example 67 to yield 7.28 g. (98.9%). EA, MS(FD).

Example 74

2-Amino-3-(2-chlorophenyl)-6-benzoyl-imidazo[1,2-a]pyridine

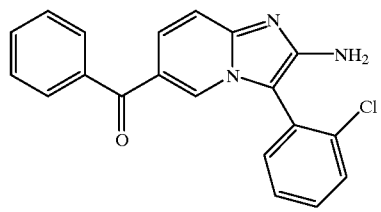

The 2-trifluoroacetamido-3-(2-chlorophenyl)-6-benzoyl-imidazo[1,2-a]pyridine (10.8 g, 24.2 mmol) was converted to product in a manner substantially analogous to Example 67 to yield 7.45 g. (88.5%). EA, MS(FD).

Example 75

2-Amino-3-(3-chlorophenyl)-6-benzoyl-imidazo[1,2-a]pyridine

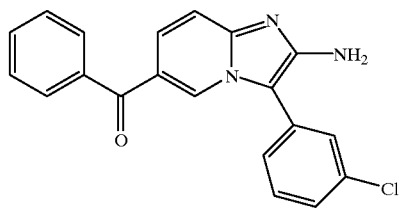

The 2-trifluoroacetamido-3-(3-chlorophenyl)-6-benzoyl-imidazo[1,2-a]pyridine (8.97 g, 20.2 mmol) was converted to product in a manner substantially analogous to Example 67 to yield 6.05 g. (86.1%). EA, MS(FD).

Example 76

2-Amino-3-(4-chlorophenyl)-6-benzoyl-imidazo[1,2-a]pyridine

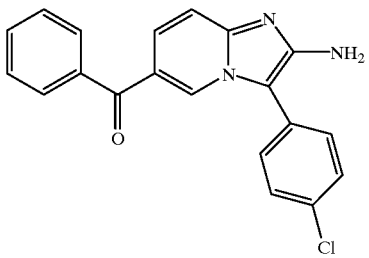

The 2-trifluoroacetamido-3-(4-chlorophenyl)-6-benzoyl-imidazo[1,2-a]pyridine (10.8 g, 24.2 mmol) was converted to product in a manner substantially analogous to Example 67 to yield 7.17 g. (85.2%). EA, MS(FD).

Example 77

2-Amino-3-(4-trifluoromethoxyphenyl)-6-benzoyl-imidazo[1,2-a]pyridine

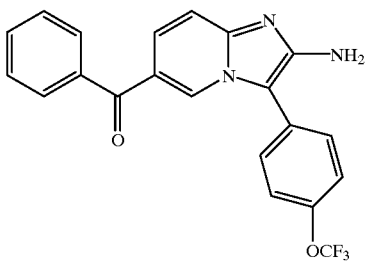

The 2-trifluoroacetamido-3-(4-trifluoromethoxyphenyl)-6-benzoyl-imidazo[1,2-a]pyridine (10.6 g, 21.5 mmol) was converted to product in a manner substantially analogous to Example 67 to yield 8.24 g. (96.7%). EA, MS(FD).

Example 78

2-Amino-3-(3-trifluoromethoxyphenyl)-6-benzoyl-imidazo[1,2-a]pyridine

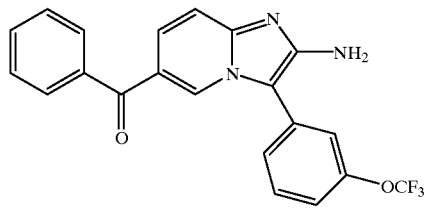

The 2-trifluoroacetamido-3-(3-trifluoromethoxyphenyl)-6-benzoyl-imidazo[1,2-a]pyridine (10.4 g, 21.1 mmol) was converted to product in a manner substantially analogous to Example 67 to yield 7.89 g. (94.4%). MS(FD), NMR.

Example 79

2-Amino-3-(2-fluoro-4-trifluoromethylphenyl)-6-benzoyl-imidazo[1,2-a]pyridine

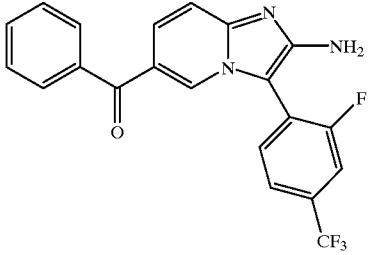

The 2-trifluoroacetamido-3-(2-fluoro-4-trifluoromethylphenyl)-6-benzoyl-imidazo[1,2-a]pyridine (8.03 g, 16.2 mmol) was converted to product in a manner substantially analogous to Example 67 to yield 6.00 g. (92.8%). EA, MS(FD).

Example 80

2-Amino-3-(2,3,4,5,6-pentafluorophenyl)-6-benzoyl-imidazo[1,2-a]pyridine

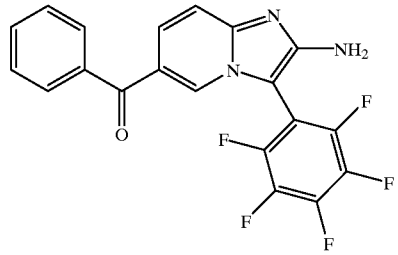

The 2-trifluoroacetamido-3-(2,3,4,5,6-pentafluorophenyl)-6-benzoyl-imidazo[1,2-a]pyridine (5.03 g, 10.1 mmol) was converted to product in a manner substantially analogous to Example 67 to yield 3.79 g. (93.3%). EA, MS(FD).

Example 81

2-Amino-3-(2-trifluoromethylphenyl)-6-benzoyl-imidazo[1,2-a]pyridine

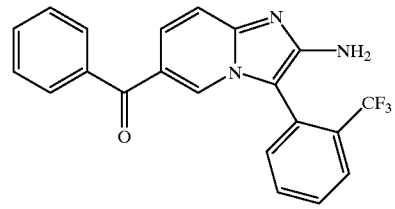

The 2-trifluoroacetamido-3-(2-trifluoromethylphenyl)-6-benzoyl-imidazo[1,2-a]pyridine (6.22 g, 13.0 mmol) was converted to product in a manner substantially analogous to Example 67 to yield 4.25 g. (85.5%). EA, MS(FD).

Example 82

2-Amino-3-(thiophen-3-yl)-6-benzoyl-imidazo[1,2-a]pyridine

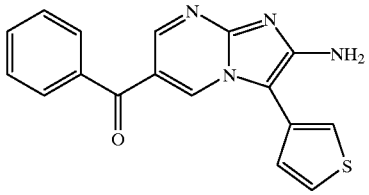

The 2-trifluoroacetamido-3-(thiophen-3-yl)-6-benzoyl-imidazo[1,2-a]pyridine (8.88 g, 21.4 mmol) was converted to product in a manner substantially analogous to Example 67 to yield 5.51 g. (80.7%). EA, MS(FD).

Example 83

2-Amino-3-(2-trifluoromethyl-4-fluorophenyl)-6-benzoyl-imidazo[1,2-a]pyridine

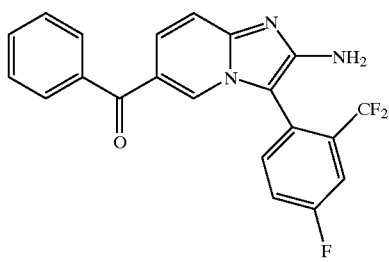

The 2-trifluoroacetamido-3-(2-trifluoromethyl-4-fluorophenyl)-6-benzoyl-imidazo[1,2-a]pyridine (11.0 g, 22.2 mmol) was converted to product in a manner substantially analogous to Example 67 to yield 8.60 g. (97.2%). MS(FD).

Example 84

2-Amino-3-(2-fluoro-6-trifluoromethylphenyl)-6-benzoyl-imidazo[1,2-a]pyridine

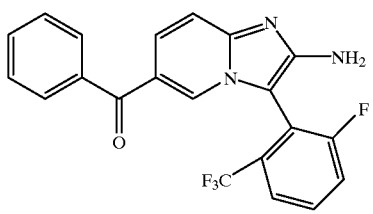

The 2-trifluoroacetamido-3-(2-fluoro-6-trifluoromethylphenyl)-6-benzoyl-imidazo[1,2-a]pyridine 2-trifluoroacetamido-3-(2,3,4,5,6-pentafluorophenyl)-6-benzoyl-imidazo[1,2-a]pyridine (1.80 g, 3.64 mmol) was converted to product in a manner substantially analogous to Example 67 to yield 1.28 g. (88.3%). EA, MS(FD).

Example 85

2-Amino-3-(2-methoxyphenyl)-6-benzoyl-imidazo[1,2-a]pyridine

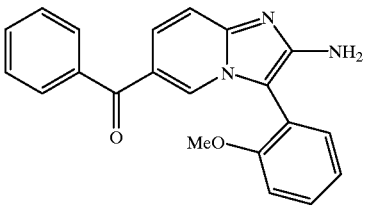

The 2-trifluoroacetamido-3-(2-methoxyphenyl)-6-benzoyl-imidazo[1,2-a]pyridine (7.40 g, 16.8 mmol) was converted to product in a manner substantially analogous to Example 67 to yield 5.0 g. (87%). EA, MS(FD).

Example 86

2-Amino-3-(4-carbomethoxyphenyl)-6-benzoyl-imidazo[1,2-a]pyridine

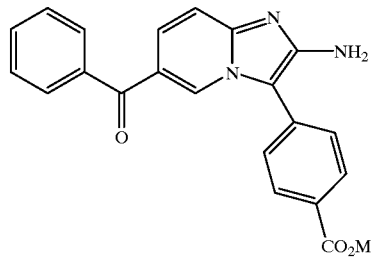

The 2-trifluoroacetamido-3-(4-carbomethoxyphenyl)-6-benzoyl-imidazo[1,2-a]pyridine (2.13 g, 16.8 mmol) was converted to product in a manner substantially analogous to Example 67 to yield 1.44 g. (85%). EA, MS(FD).

Example 87

2-Amino-3-(4-nitrophenyl)-6-benzoyl-imidazo[1,2-a]pyridine

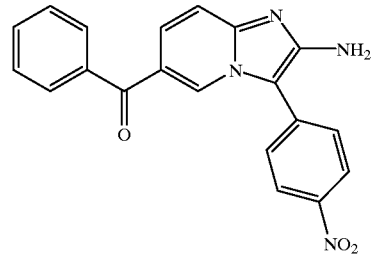

The 2-trifluoroacetamido-3-(4-nitrophenyl)-6-benzoyl-imidazo[1,2-a]pyridine (8.59 g, 18.9 mmol) was converted to product in a manner substantially analogous to Example 67 to yield 5.04 g. (74.4%). EA, MS(FD).

Example 88

2-Amino-3-isobutyl-6-benzoyl-imidazo[1,2-a]pyridine

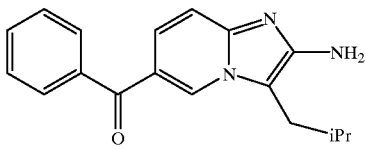

The 2-trifluoroacetamido-3-isobutyl-6-benzoyl-imidazo[1,2-a]pyridine (2.37 g, 6.09 mmol) was converted to product in a manner substantially analogous to Example 67 to yield 1.49 g. (83.5%). EA, MS(FD).

Example 89

2-Amino-3-(4-carboxyphenyl)-6-benzoyl-imidazo[1,2-a]pyridine

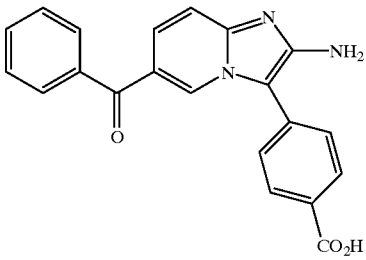

The 2-amino-3-(4-carbomethoxyphenyl)-6-benzoyl-imidazo[1,2-a]pyridine (3.00 g, 8.09 mmol) was dissolved in 25 ml of THF and 8 ml of $H_2O$ and stirred at RT. Lithium hydroxide (968 mg, 40.4 mmol) was added and the reaction stirred overnight. The solvents were removed, and $H_2O$ added to solids which were then filtered and washed with $H_2O$. The solids were recrystalized from MeOH to yield 2.62 g of product. (91%). EA, MS(FD).

Example 90

2-Amino-3-(4-N-methoxyamido)-6-benzoyl-imidazo[1,2-a]pyridine

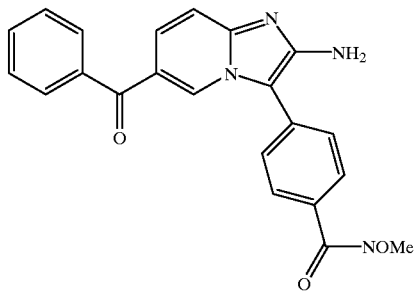

The 2-amino-3-(4-carboxyphenyl)-6-benzoyl-imidazo[1,2-a]pyridine (714 mg, 2.00 mmol), methoxyamine hydrochloride (1.34 g, 16.0 mmol), and diisopropylethylamine (2.93 ml, 16.0 mmol) were suspended in 20 ml of dry DMF under $N_2$. Within 20 minutes the solution was clear to yellow-orange. The reaction was stirred overnight at RT. The DMF was removed in vacuo and the residue poured onto $H_2O$ and stirred for 1 hour. The solids were then filtered and air dried. The crude product was recrystalized from EtOAc to give 317 mg of product. (41.0%). EA, MS(FD).

Example 91

2-Amino-3-(4-fluorophenyl)-6-(4-fluorobenzoyl)-imidazo[1,2-a]pyridine

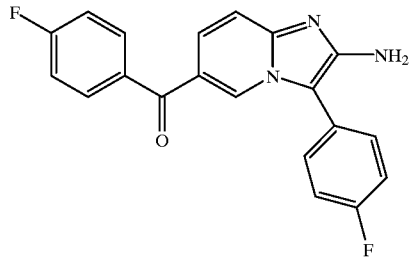

The 2-trifluoroacetamido-3-(4-fluorophenyl)-6-(4-fluorobenzoyl)-imidazo[1,2-a]pyridine (7.11 g, 16.0 mmol) was converted to product in a manner substantially analogous to Example 67 to yield 4.80 g. (86.2%). MS(FD), NMR.

Example 92

2-Amino-3-(2-fluoro-4-trifluoromethylphenyl)-6-(4-fluorobenzoyl)-imidazo[1,2-a]pyridine

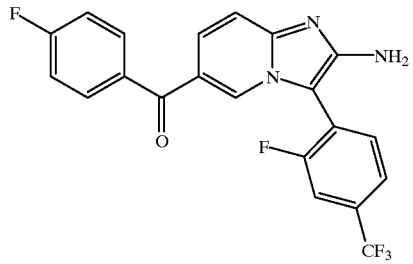

The 2-trifluoroacetamido-3-(2-fluoro-4-trifluoromethylphenyl)-6-(4-fluorobenzoyl)-imidazo[1,2-a]pyridine (6.75 g, 13.2 mmol) was converted to product in a manner substantially analogous to Example 67 to yield 4.66 g. (85%). EA, MS(FD).

Example 93

2-amino-3-phenyl-6-(α-phenylacetyl)-imidazo[1,2-a]pyridine

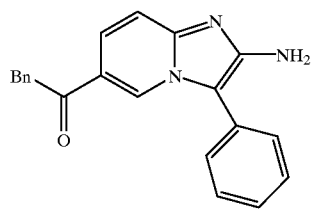

The N-(3-phenyl-6-[N-methyl-N-methoxycarbamoyl]imidazo[1,2-a]pyridin-2-yl)-2,2,5,5-tetramethyl-1-aza-2,5- disilacyclopentane (812 mg, 4 mmol) was dissolved in 30 ml of THF under $N_2$ and benzylmagnesiumchloride (2 M in THF, 6 ml, 12.0 mmol) was added. The mixture was allowed to stir for 18 hours at RT before adding 15 ml of MeOH and 3 ml of acetic acid. The mixture was allowed to stir for 1 hour at RT. The solvents were removed in vacuo and the residue taken up in 400 ml of EtOAc and 60 ml of $NaHCO_3$. The EtOAc was separated and washed with with brine (2×75 ml), dried over $NaSO_4$, and then concentrated in vacuo. The residue was purified by normal phase flash chromatography (EtOAc). The product fractions were recrystalized from EtOAc to yield 398 mg of product. (31.6%). MS(FD), NMR.

Example 94

2-Amino-3-phenyl-6-(picolinoyl)-imidazo[1,2-a]pyridine

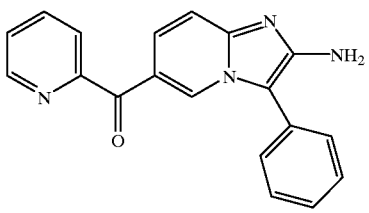

The 2-iodopyridine (1.23 g, 6.00 mmol) was dissolved in 40 ml of THF under $N_2$ and ethylmagnesiumbromide (2 ml, 3 M, 6 mmol) was added. The mixture was allowed to stir for 30 minutes at RT before adding N-(3-phenyl-6-[carboxyl]imidazo[1,2-a]pyridin-2-yl)-2,2,5,5-tetramethyl-1-aza-2,5-disilacyclopentane (820 mg, 2 mmol) in 25 ml THF via cannula. The resulting mixture was allowed to stir for 18 hours at RT. Methanol (4 ml) and 2 ml of acetic acid were added and the mixture was allowed to stir for 1 hour at RT. The solvents were removed in vacuo and the residue purified by normal phase chromatography. The product fractions were recrystalized from EtOAc to yield 205 mg of product. (10.9%). MS(FD), NMR.

Example 95

2-Amino-3-phenyl-6-(nicotinoyl)-imidazo[1,2-a]pyridine

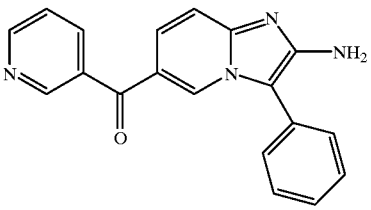

The N-(3-phenyl-6-[carboxyl]imidazo[1,2-a]pyridin-2-yl)-2,2,5,5-tetramethyl-1-aza-2,5-disilacyclopentane (820 mg, 2.00 mmol) was converted to product using 3-iodopyridine in a manner substantially analogous to Example 94 to yield 271 mg. (14.4%). EA, MS(FD).

Example 96

2-Amino-3-phenyl-6-(isonicotinoyl)-imidazo[1,2-a]pyridine

The N-(3-phenyl-6-[carboxyl]imidazo[1,2-a]pyridin-2-yl)-2,2,5,5-tetramethyl-1-aza-2,5-disilacyclopentane (3.28 g, 8.00 mmol) was converted to product using 4-iodopyridine in a manner substantially analogous to Example 94 to yield 1.74 g. (69.3%). EA, MS(FD).

Example 97

2-Amino-3-(2,4-difluorophenyl)-6-[(E)-benzyloxim-α-yl]-imidazo[1,2-a]pyridine

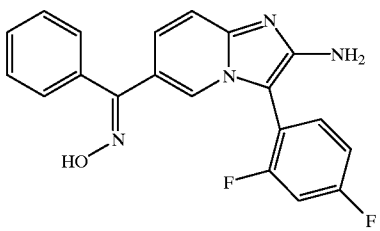

The 2-amino-3-(2,4-difluorophenyl)-6-benzoyl-imidazo[1,2-a]pyridine (1.00 g, 2.87 mmol) was dissolved in 40 ml of 80% EtOH/$H_2O$. Hydroxylamine hydrochloride (2.39 g, 34.4 mmol) and NaOAc (2.82 g, 34.4 mmol) were added and this mixture was heated to reflux for 4 hours, monitoring the progress of the reaction by HPLC. The reaction was worked up by removing the solvents in vacuo and taking the residue up in 900 ml of EtOAc. The solution was washed with saturated $NaOHCO_3$ (3×100 ml), brine (3×100 ml), dried over $Na_2SO_4$, filtered, and concentrated in vacuo. The residue was recrystalized with EtOAc and further purified by HPLC to yield 130 mg of the E-isomer. (17.2%). MS(FD), UV.

Example 98

2-Amino-3-(4-methoxyphenyl)-6-(benzyloxim-α-yl)-imidazo[1,2-a]pyridine

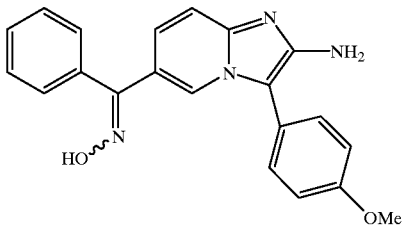

The 2-amino-3-(4-methoxyphenyl)-6-benzoyl-imidazo[1,2-a]pyridine (2.00 g, 5.83 mmol) was converted to product in a manner substantially analogous to Example 97 to yield 490 mg of E-product, (24.0%), EA, MS(FD), and a small but unspecified amount of Z-product. EA, MS(FD).

Example 99

2-Amino-3-(napth-2-yl)-6-[(E)-benzyloxim-α-yl]-imidazo[1,2-a]pyridine

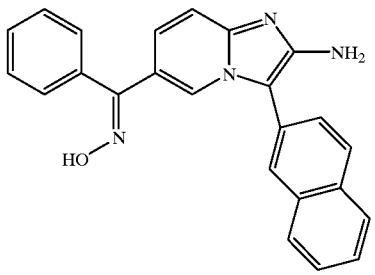

The 2-amino-3-(napth-2-yl)-6-benzoyl-imidazo[1,2-a]pyridine (2.00 g, 5.51 mmol) was converted to product in a manner substantially analogous to Example 97 to yield 115 mg of E-product. (5.52%). EA, MS(FD).

Example 100

2-Amino-3-napthyl-6-(benzyloxim-α-yl)-imidazo[1,2-a]pyridine

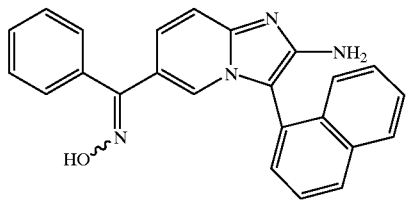

The 2-amino-3-napthyl-6-benzoyl-imidazo[1,2-a]pyridine (2.00 g, 5.51 mmol) was converted to product in a manner substantially analogous to Example 97 to yield 470 mg of E-product, (22.60%), EA, MS(FD), and 810 mg of Z-product. (38.9%). NMR.

Example 101

2- Amino-3-(2-fluorophenyl)-6-[(E)-benzyloxim-α-yl]-imidazo[1,2-a]pyridine

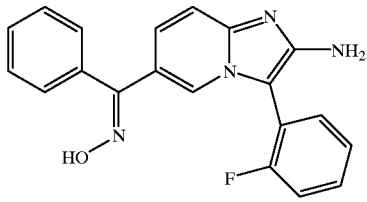

The 2-amino-3-(2-fluorophenyl)-6-benzoyl-imidazo[1,2-a]pyridine (2.62 g, 7.92 mmol) was converted to product in a manner substantially analogous to Example 97 to yield 1.08 g of E-product. (39.3%). MS(FD), NMR.

Example 102

2-Amino-3-(3-fluorophenyl)-6-[(E)-1-benzyloxim-α-yl]-imidazo[1,2-a]pyridine

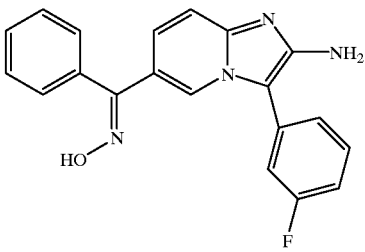

The 2-amino-3-(3-fluorophenyl)-6-benzoyl-imidazo[1,2-a]pyridine (2.00 g, 6.04 mmol) was converted to product in a manner substantially analogous to Example 97 to yield 463 mg of E-product. (22.2%), EA, MS(FD).

Example 103

2-Amino-3-(4-fluorophenyl)-6-[(E)-benzyloxim-α-yl]-imidazo[1,2-a]pyridine

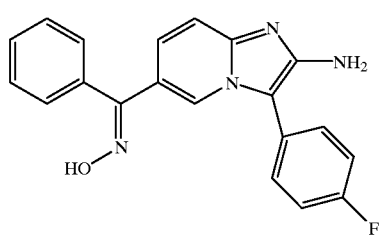

The 2-amino-3-(4-fluorophenyl)-6-benzoyl-imidazo[1,2-a]pyridine (3.00 g, 9.06 mmol) was converted to product in a manner substantially analogous to Example 97 to yield 2.78 g of B-product. (88.8%). EA, MS(FD).

Example 104

2-Amino-3-(3,5-difluorophenyl)-6-[(E)-benzyloxim-α-yl]-imidazo[1,2-a]pyridine

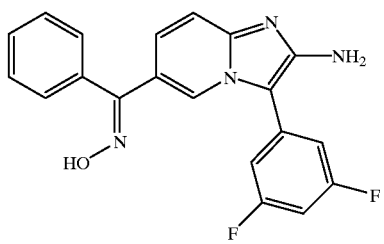

The 2-amino-3-(3,5-difluorophenyl)-6-benzoyl-imidazo[1,2-a]pyridine (1.00 g, 2.87 mmol) was converted to product in a manner substantially analogous to Example 97 to yield 65 mg of E-product. (6.22%). EA, MS(FD).

Example 105

2-Amino-3-(2,5-difluorophenyl)-6-[(E)-benzyloxim-α-yl]-imidazo[1,2-a]pyridine

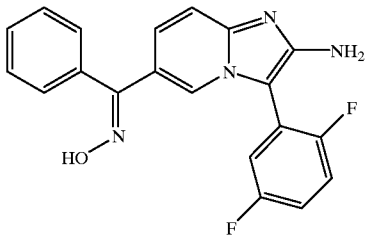

The 2-amino-3-(2,5-difluorophenyl)-6-benzoyl-imidazo[1,2-a]pyridine (1.00 g, 2.87 mmol) was converted to product in a manner substantially analogous to Example 97 to yield 315 mg of E-product. (30.2%). EA, MS(FD).

Example 106

2-Amino-3-(3-trifluoromethylphenyl)-6-[(E)-benzyloxim-α-yl]-imidazo[1,2-a]pyridine

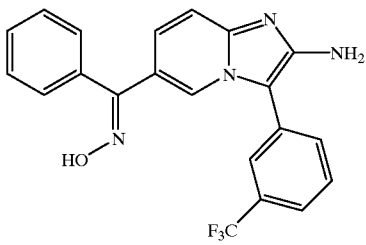

The 2-amino-3-(3-trifluoromethylphenyl)-6-benzoyl-imidazo[1,2-a]pyridine (2.00 g, 5.24 mmol) was converted to product in a manner substantially analogous to Example 97 to yield 579 mg of E-product. (27.9%). EA, MS(FD).

Example 107

2-Amino-3-(4-bromophenyl)-6-(benzyloxim-α-yl)-imidazo[1,2-a]pyridine

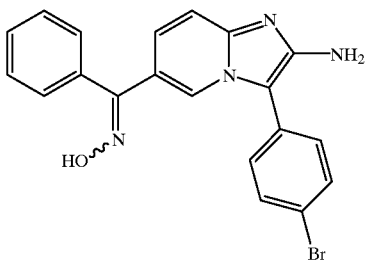

The 2-amino-3-(4-bromophenyl)-6-benzoyl-imidazo[1,2-a]pyridine (1.80 g, 4.59 mmol) was converted to product in a manner substantially analogous to Example 97 to yield 1.20 g of a 1:1 mixture of E and Z isomer products. (64.2%). EA, MS(FD).

Example 108

2-Amino-3-(2,3,4-trifluorophenyl)-6-[(E)-benzyloxim-α-yl]-imidazo[1,2-a]pyridine

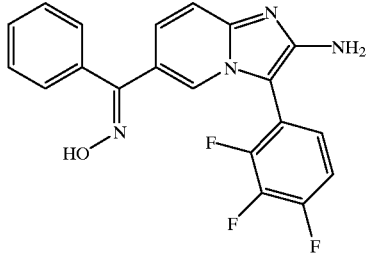

The 2-amino-3-(2,3,4-trifluorophenyl)-6-benzoyl-imidazo[1,2-a]pyridine (2.00 g, 5.45 mmol) was converted to product in a manner substantially analogous to Example 97 to yield 508 mg of E-product. (24.1%). EA, MS(FD).

Example 109

2-Amino-3-(3,4-difluorophenyl)-6-[(E)-benzyloxim-α-yl]-imidazo[1,2-a]pyridine

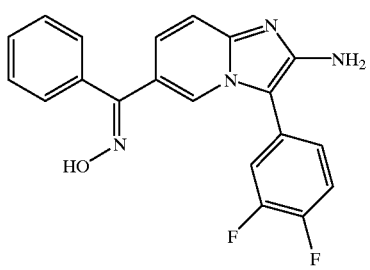

The 2-amino-3-(3,4-difluorophenyl)-6-benzoyl-imidazo[1,2-a]pyridine (2.00 g, 5.73 mmol) was converted to product in a manner substantially analogous to Example 97 to yield 507 mg of E-product. (24.2%). EA, MS(FD).

Example 110

2-Amino-3-(3,4-dichlorophenyl)-6-[(E)-benzyloxim-α-yl]-imidazo[1,2-a]pyridine

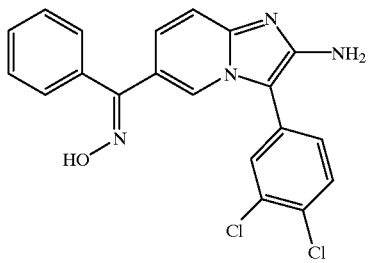

The 2-amino-3-(3,4-dichlorophenyl)-6-benzoyl-imidazo[1,2-a]pyridine (2.00 g, 5.25 mmol) was converted to product in a manner substantially analogous to Example 97 to yield 643 mg of E-product. (31.1%). EA, MS(FD).

Example 111

2-Amino-3-(2,4,5-trifluorophenyl)-6-[(E)-benzyloxim-α-yl]-imidazo[1,2-a]pyridine

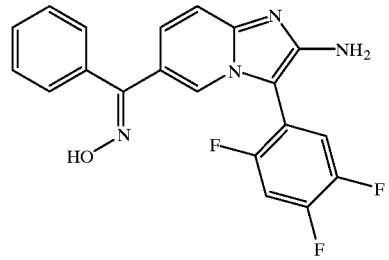

The 2-amino-3-(2,4,5-trifluorophenyl)-6-benzoyl-imidazo[1,2-a]pyridine (2.00 g, 5.45 mmol) was converted to product in a manner substantially analogous to Example 97 to yield 344 mg of E-product. (16.6%). EA, MS(FD).

Example 112

2-Amino-3-(2-chlororophenyl)-6-[(E)-benzyloxim-α-yl]-imidazo[1,2-a]pyridine

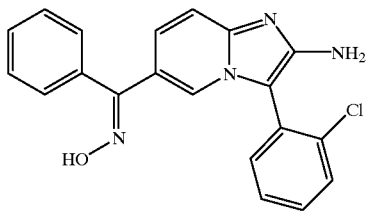

The 2-amino-3-(2-chlorophenyl)-6-benzoyl-imidazo[1,2-a]pyridine (2.00 g, 5.76 mmol) was converted to product in a manner substantially analogous to Example 97 to yield 180 mg of E-product. (8.61%). EA, MS(FD).

Example 113

2-Amino-3-(3-chlorophenyl)-6-[(E)-benzyloxim-yl]-imidazo[1,2-a]pyridine

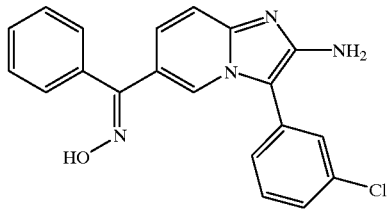

The 2-amino-3-(3-chlorophenyl)-6-benzoyl-imidazo[1,2-a]pyridine (2.00 g, 5.75 mmol) was converted to product in a manner substantially analogous to Example 97 to yield 551 mg of E-product. (26.4%). EA, MS(FD).

Example 114

2-Amino-3-(4-chlorophenyl)-6-[(E)-benzyloxim-α-yl]-imidazo[1,2-a]pyridine

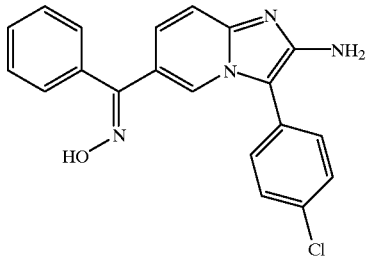

The 2-amino-3-(4-chlorophenyl)-6-benzoyl-imidazo[1,2-a]pyridine (2.00 g, 5.75 mmol) was converted to product in a manner substantially analogous to Example 97 to yield 180 mg of E-product. (8.61%). EA, MS(FD).

Example 115

2-Amino-3-(4-trifluoromethoxyphenyl)-6-[(E)-benzyloxim-α-yl]-imidazo[1,2-a]pyridine

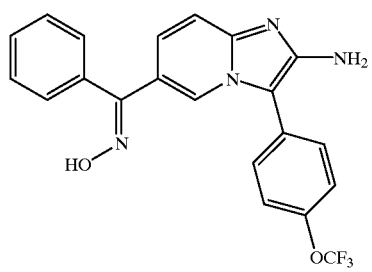

The 2-amino-3-(4-trifluoromethoxyphenyl)-6-benzoyl-imidazo[1,2-a]pyridine (2.00 g, 5.04 mmol) was converted to product in a manner substantially analogous to Example 97 to yield 383 mg of E-product. (18.4%). EA, MS(FD).

Example 116

2-Amino-3-(3-trfluoromethoxyphenyl)-6-[(E)-benzyloxim-α-yl]-imidazo[1,2-a]pyridine

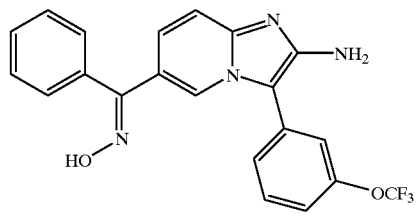

The 2-amino-3-(3-trifluoromethoxyphenyl)-6-benzoyl-imidazo[1,2-a]pyridine (2.00 g, 5.04 mmol) was converted to product in a manner substantially analogous to Example 97 to yield 224 mg of E-product. (10.80%). EA, MS(FD).

Example 117

2-Amino-3-(2-fluoro-4-trifluoromethylphenyl)-6-(benzyloxim-α-yl)-imidazo[1,2-a]pyridine

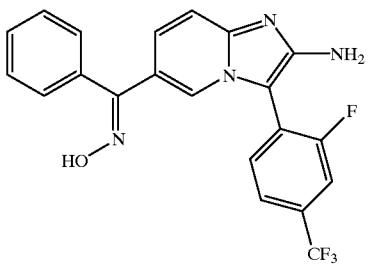

The 2-amino-3-(2-fluoro-4-trifluoromethylphenyl)-6-benzoyl-imidazo[1,2-a]pyridine (2.00 g, 5.01 mmol) was converted to product in a manner substantially analogous to Example 97 to yield 742 mg of E-product. (35.7%). EA, MS(FD).

Example 118

2-Amino-3-phenyl-6-[(E)-benzyloxim-α-yl]-imidazo[1,2-a]pyridine

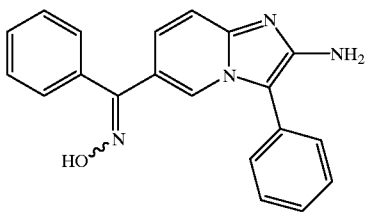

The 2-amino-3-phenyl-6-benzoyl-imidazo[1,2-a]pyridine (133 mg, 0.426 mmol) was treated with hydroxylamine hydrochloride (500 mg, 7.20 mmol), 2.5 ml of pyridine, and 7.5 ml of dry EtOH. After refluxing for 2.5 hours, 200 ml of EtOAc was added and the solution washed twice with saturated NaHSO₃. THe organic layer was dried over MgSO₄ and the solvent removed in vacuo. The product crystalized out in EtOAc to yield 64 mg of B-product, (45.79), MS(FD), and 68 mg of the Z isomer. (48.6%). MS(FD).

Example 119

2-Amino-3-(2,6-difluorophenyl)-6-[(E)-benzyloxim-α-yl]-imidazo [1,2-a]pyridine

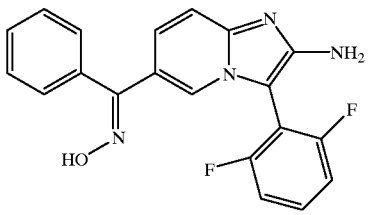

The 2-amino-3-(2,6-difluorophenyl)-6-benzoyl-imidazo[1,2-a]pyridine (2.00 g, 5.73 mmol) was converted to product in a manner substantially analogous to Example 97 to yield 383 mg of E-product. (18.4%). EA, MS(FD).

Example 120

2-Amino-3-(2,3,4,5,6-pentafluorophenyl)-6-[(E)-benzyloxim-α-yl]-imidazo[1,2-a]pyridine

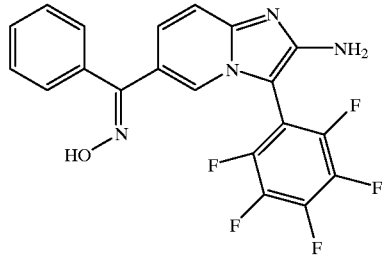

The 2-amino-3-(2,6-difluorophenyl)-6-benzoyl-imidazo[1,2-a]pyridine (4.52 g, 11.2 mmol) was converted to product in a manner substantially analogous to Example 97 to yield 940 mg of E-product. (20%). EA, MS(FD).

Example 121

2-Amino-3-(2-trifluoromethylphenyl)-6-[(E)-benzyloxim-α-yl]-imidazo[1,2-a]pyridine

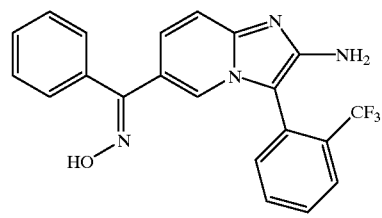

The 2-amino-3-(2-trifluoromethylphenyl)-6-benzoyl-imidazo[1,2-a]pyridine (2.00 g, 5.25 mmol) was converted to product in a manner substantially analogous to Example 97 to yield 146 mg of E-product. (7.02%). EA, MS(FD).

Example 122

2-Amino-3-(thiophen-3-yl)-6-[(E)-benzyloxim-α-yl]-imidazo[1,2-a]pyridine

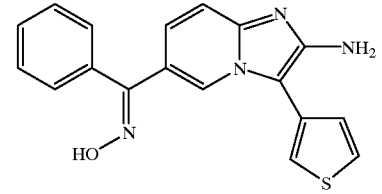

The 2-amino-3-(thiophen-3-yl)-6-benzoyl-imidazo[1,2-a]pyridine (2.00 g, 6.27 mmol) was converted to product in a manner substantially analogous to Example 97 to yield 497 mg of E-product. (23.8%). EA, MS(FD).

Example 123

2-Amino-3-(2-trifluoromethyl-4-fluorophenyl)-6-[(E)-benzyloxim-α-yl]-imidazo[1,2-a]pyridine

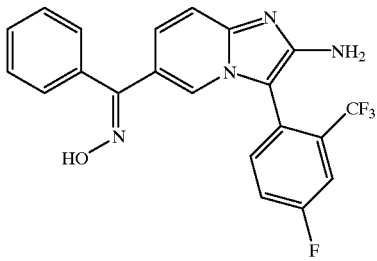

The 2-amino-3-(2-trifluoromethyl-4-fluorophenyl)-6-benzoyl-imidazo[1,2-a]pyridine (2.00 g, 5.01 mmol) was converted to product in a manner substantially analogous to Example 97 to yield 288 mg of E-product. (13.8%). EA, MS (ED).

Example 124

2-Amino-3-(2-fluoro-6-trifluoromethylphenyl)-6-[(E)-benzyloxim-α-yl]-imidazo[1,2-a]pyridine

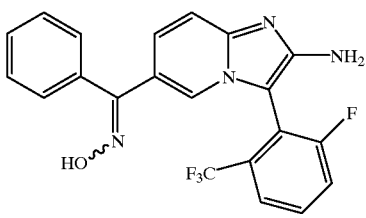

The 2-amino-3-(2-fluoro-6-trifluoromethylphenyl)-6-benzoyl-imidazo[1,2-a]pyridine (1.28 g, 3.21 mmol) was converted to product in a manner substantially analogous to Example 97 to yield 75.0 mg of E-product, (5.64%), EA, MS(FD), and 395 mg of Z-product. (29.7%). MS(FD), NMR.

Example 125

2-Amino-3-(4-trifluoromethylphenyl)-6-[(E)-benzyloxim-α-yl]-imidazo[1,2-a]pyridine

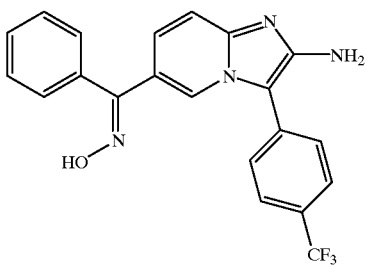

The 2-amino-3-(4-trifluoromethylphenyl)-6-benzoyl-imidazo[1,2-a]pyridine (2.00 g, 5.25 mmol) was converted to product in a manner substantially analogous to Example 97 to yield 512 mg of E-product. (24.6%). EA, MS(FD).

Example 126

2-Amino-3-(4-carbomethoxyphenyl)-6-[(E)-benzyloxim-α-yl]-imidazo[1,2-a]pyridine

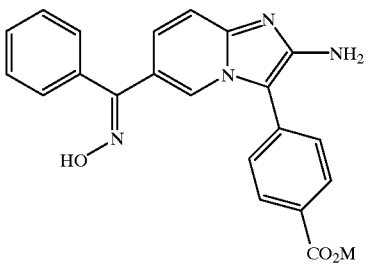

The 2-amino-3-(4-carbomethoxyphenyl)-6-benzoyl-imidazo[1,2-a]pyridine (1.00 g, 2.70 mmol) was converted to product in a manner substantially analogous to Example 97 to yield 437 mg of E-product. (43.5%). EA, MS(FD).

Example 127

2-Amino-3-(4-carboxyphenyl)-6-[benzyloxim-α-yl]-imidazo[1,2-a]pyridine

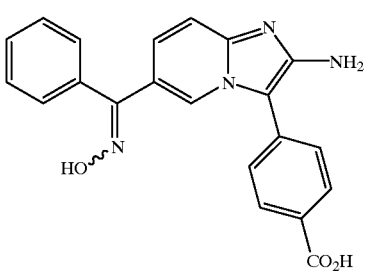

The 2-amino-3-(4-carboxyphenyl)-6-benzoyl-imidazo[1,2-a]pyridine (2.00 g, 5.60 mmol) was converted to product in a manner substantially analogous to Example 97 to yield 990 mg of an E and Z isomer mixture. (46.6% global yield). NMR.

Example 128

2-Amino-3-benzyl-6-[benzyloxim-α-yl]-imidazo[1,2-a]pyridine

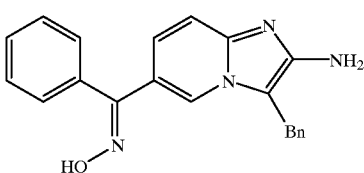

The 2-amino-3-benzyl-6-benzoyl-imidazo[1,2-a]pyridine (2.00 g, 5.60 mmol) was converted to product in a manner substantially analogous to Example 97 to yield 210 mg of the E isomer product. (16.5%). EA, MS(FAB).

Example 129

2-Amino-3-isobutyl-6-[benzyloxim-α-yl]-imidazo[1,2-a]pyridine

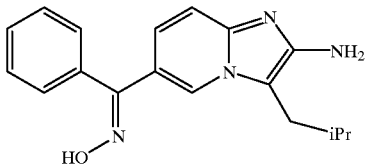

The 2-amino-3-isobutyl-6-benzoyl-imidazo[1,2-a]pyridine (820 mg, 2.80 mmol) was converted to product in a manner substantially analogous to Example 97 to yield 120 mg of the E isomer product. (13.9%). EA, MS(FAB).

Example 130

2-Amino-3-(4-fluorophenyl)-6-[(E)-1-(4-fluorobenzyl)oxim-α-yl]-imidazo[1,2-a]pyridine

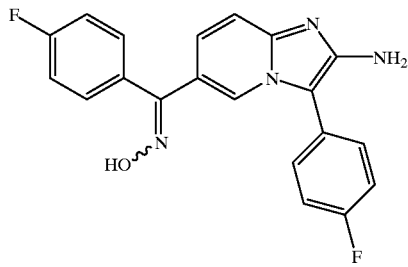

The 2-amino-3-(4-fluorophenyl)-6-(4-fluorobenzoyl)-imidazo[1,2-a]pyridine (2.00 g, 5.73 mmol) was converted to product in a manner substantially analogous to Example 97 to yield 572 mg of E-product, (27.4%), EA, MS(FD), and 198 mg of Z-product. (9.47%). EA, MS(FD).

Example 131

2-Amino-3-(2-fluoro-4-trifluoromethylphenyl)-6-[(E)-1-(4-fluorobenzyl)oxim-α-yl]-imidazo [1,2-a]pyridine

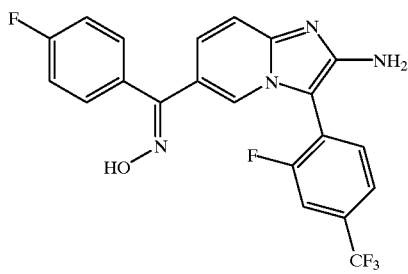

The 2-amino-3-(2-fluoro-4-trifluoromethylphenyl)-6-(4-fluorobenzoyl)-imidazo[1,2-a]pyridine (2.00 g, 4.80 mmol) was converted to product in a manner substantially analogous to Example 97 to yield 310 mg of E-product. (15%). EA, MS(FD).

Example 132

2-Amino-3-phenyl-6-[(E)-phenylacetoxim-α-yl]-imidazo[1,2-a]pyridine

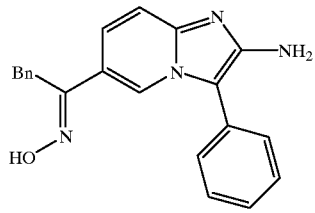

The 2-amino-3-phenyl-6-(α-phenylacetyl)-imidazo[1,2-a]pyridine (732 mg, 2.24 mmol) was converted to product in a manner substantially analogous to Example 97 to yield 485 mg of E-product. (63.3%). EA, MS(FD).

Example 133

2-Amino-3-phenyl-6-(picolinyloxim-α-yl)-imidazo[1,2-a)pyridine

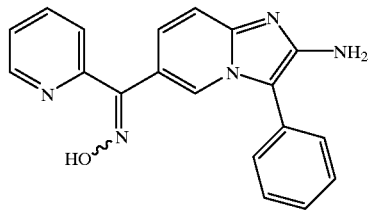

To a suspension of 2-amino-3-phenyl-6-(picolinoyl)-imidazo[1,2-a]pyridine (1.57 g, 5.00 mmol) in 100 ml of 80% aqueous EtOH was added hydroxylamine hydrochloride (4.17 g, 60.0 mmol) and NaOAc (4.92 g, 60.0 mmol). The mixture was refluxed for 6 hours and then the solvent was removed in vacuo. The residue was partitioned between 900 ml of EtOAc and 100 ml of saturated NaHCO$_3$. The EtOAc was separated and washed with brine, dried over Na$_2$SO$_4$, filtered, and concentrated in vacuo. The residue was recrystalized from EtOAc to yield a mixture of both product isomers. The mixture was triturated with CH$_2$Cl$_2$ and the solids filtered. The filtrate was chromatographed (normal phase) to yield 75.8 mg of cis product. (4.6%). EA, MS(FD). The solids were recrystalized twice from MeOH to yield 134 mg of trans product. (8.1%). EA, MS(FD).

Example 134

2-Amino-3-phenyl-6-(nicotinyloxim-α-yl)-imidazo [1,2-a]pyridine

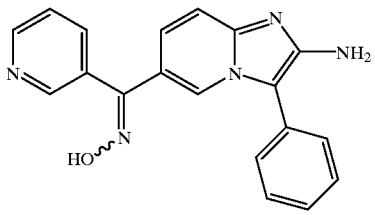

The 2-amino-3-phenyl-6-(nicotinoyl)-imidazo[1,2-a]pyridine (1.18 g, 3.75 mmol) was converted to product in a manner substantially analogous to Example 78 to yield 127 mg of cis product, (10.3%), MS(FD), NMR, and 20.5 mg of 80% trans product. (1.3% corrected). MS(FD), NMR.

Example 135

2-Amino-3-phenyl-6-(cis-isonicotinyloxim-α-yl)-imidazo1,2-a]pyridine

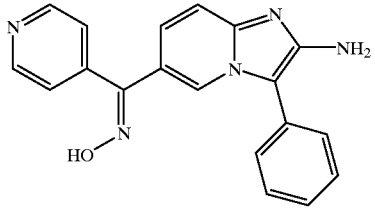

The 2-amino-3-phenyl-6-(isonicotinoyl)-imidazo[1,2-a] pyridine (1.57 g, 5.00 mmol) was converted to product in a manner substantially analogous to Example 78 to yield 466 mg of cis, (28.3%), EA, MS(FD), NMR, and 230 mg of trans. (14%). EA, MS(FD).

Example 136

2-Amino-3-phenyl-6-(1-phenyl-2-cyanovinyl)-imidazo[1,2-a]pyridine

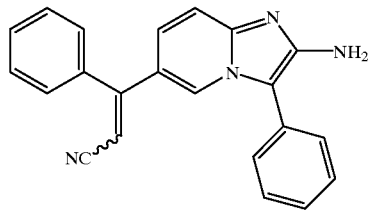

The 2-amino-3-phenyl-6-benzoyl-imidazo[1,2-a]pyridine (1.57 g, 5.00 mmol) was dissolved in 30 ml of THF and diethylcyanophosphonate (1.63 g, 10.0 mmol) followed by potassium bistrimethylsilylamide (0.5 M in toluene, 5 ml, 10 mmol) were added. The reaction was allowed to stir for 5 days. The THF was removed in vacuo and the residue dissolved in 500 ml of EtOAc. The EtOAc was washed with 50 ml of $H_2O$, brine (2×50 ml), dried over $NaSO_4$, and then concentrated in vacuo. The residue was purified by normal phase flash chromatography (EtOAc) to yield 250 mg of product which was recrystalized from EtOAc to yield 98 mg of Z-product, (5.82%), ERA, MS(FD), and 128 mg of E-product. (7.60%). EA, MS(FD).

Example 137

2-Amino-3-isobutyl-6-(1-phenyl-2-cyanovinyl)-imidazo[1,2-a]pyridine

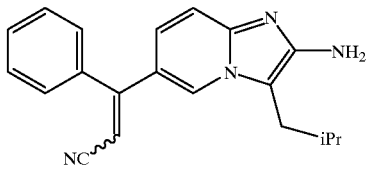

The 2-amino-3-isobutyl-6-benzoyl-imidazo[1,2-a] pyridine (1.46 g, 5.00 mmol) was converted to product in a manner substantially analogous to Example 136 to yield 200 mg of Z-product, (12.7%), MS(FD), NMR, and 130 mg of E-product. (8.23%). EA, MS(FD).

Example 138

2-Amino-3-methylthio-6-benzoyl-imidazo[1,2-a]pyridine

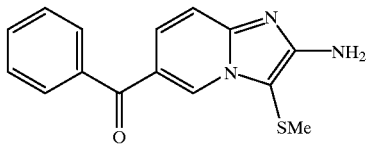

The 2-trifluoroacetamido-3-methylthio-6-benzoyl-imidazo[1,2-a]pyridine (100 mg, 263 mmol) was dissolved in 20 mL of a mixture of $MeOH/CH_2Cl_2$ 1:1, and 5 g of silica gel was added. The mixture was stirred at RT for 2 days. The residue was filtered and washed with $CH_2Cl_2$ and the solution was concentrated in vacuo to give 63 mg (850%) of a yellow solid. $^1$H-NMR (200 MHz, $CDCl_3$) d 2.12 (s, 3H, SMe), 4.40 (bs, 2H, NH2), 7.46–7.80 (m, 7H, ArH+H7+H8), 8.68 (d, J57=1.7, H5). $^{13}$C-NMR (50 MHz, CDCl3) d 18.0 (SMe), 95.0, 122.7, 125.8, 127.7, 128.5, 129.6, 132.6, 137.4, 145.3, 156.1, 193.5.

Example 139

2-Amino-3-methylsulfonyl-6-benzoyl-imidazo[1,2-a)pyridine

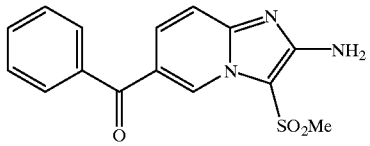

The 2-trifluoroacetamido-3-methylsulfonyl-6-benzoyl-imidazo[1,2-a]pyridine (160 mg, 0.438 mmol) was converted to product in a manner substantially analogous to Example 138 to give 92 mg. (78%). $^1$H-NMR (200 MHz, $CDCl_3$) d 3.06 ( s, 3H, SO2Me), 4.82 (bs, 2H, NH2), 7.53–7.82 (m, 6H, ArH+H7+H8), 8.78 (d, J57=1.6, H5).

Example 140

2-Amino-3-isopropylthio-6-benzoyl-imidazo[1,2-a]pyridine

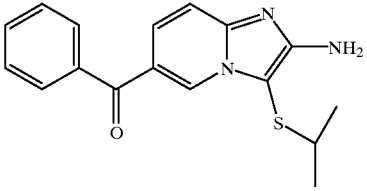

The 2-trifluoroacetamido-3-isopropylsulfonyl-6-benzoyl-imidazo[1,2-a]pyridine (16 mg, 0.0393 mmol) was converted to product in a manner substantially analogous to Example 138 to give 11 mg. (88%). EIMS m/z 311 M$^+$(28), 268 (100), 224 (27), 105 (41), 77 (29), $^1$H-NMR (CDCl$_3$) d 8.75 (s, 1H, H5), 7.79–7.47 (m, 7H, Ar), 4.62 (broad, s, 2H, NH$_2$), 3.09 (hept., 1H, J=6.4 Hz, C$\underline{H}$—(CH$_3$)$_2$, 1.22 (d, 6H, J=6.7 Hz, (C$\underline{H}_3$)$_2$—CH), $^{13}$C-NMR (CDCl$_3$) d 199.3, 157.1, 145.2, 137.3, 132.6, 129.5, 128.4, 127.9, 126.0, 122.8, 113.6, 40.8, 23.4.

Example 141

2-Amino-3-phenyl-6-(2-fluorobenzoyl)-imidazo[1,2-a]pyridine

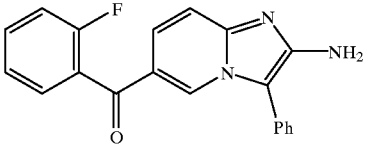

To a solution of 1-bromo-2-fluorobenzene (191 mL, 1.75mmol) in dry THF (2 mL) under an argon atmosphere was added t-butyl lithium dropwise. After stirring for 50 minutes at −78° C., a solution of 2-amino-3-phenyl-6-(N-methyl-N-methoxycarbamoyl)imidazo[1,2-a]pyridine (148 mg, 0.5 mmol) in dry THF (3 mL) was added. The resulting red-orange solution was stirred at the same temperature for another 50 minutes and then allowed to warm to RT. The solution was poured into H$_2$O (20 mL) and extracted with EtOAc (2×20 mL). The organic layer was washed with H$_2$O, dried (Na$_2$SO$_4$), and removed in vacuo to give a brown solid. The crude solid was purified by column chromatography (CH$_2$Cl$_2$/CH$_3$CN 2.5/1) to give 84.0 mg (50.6%) of product as a yellow solid. MS(FAB) m/z 332.2 (M$^+$+1, 51.99), NMR (200 MHz, CDCl$_3$) d 4.27 (bs, 2H, NH), 7.12–7.58 (m, 11H, ArH+H$_7$+H$_8$), 8.71 (s, H$_5$).

Example 142

2-Amino-3-phenyl-6-(3-fluorobenzoyl)-imidazo[1,2-a]pyridine

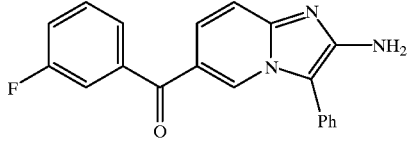

The 2-amino-3-phenyl-6-(N-methyl-N-methoxycarbamoyl)imidazo[1,2-a]pyridine (148 mg, 0.500 mmol) and 1-bromo-3-fluorobenzene were converted to product in a manner substantially analogous to Example 141 to give 37 mg. (37%). MS(FAB$^+$) m/z 332.2 (M$^+$+1, 86.6), NMR (200 MHz, CDCl$_3$) d 4.22 (bs, 2H, NH), 7.21–7.55 (m, 11H, ArH+H$_7$+H$_8$), 8.69 (d, J$_{57}$=1.1, H$_5$).

Example 143

2-Amino-3-phenyl-6-(4-fluorobenzoyl)-imidazo[1,2-a]pyridine

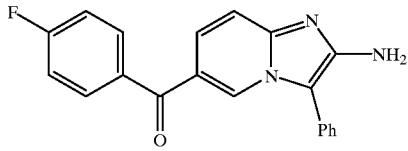

The 2-amino-3-phenyl-6-(N-methyl-N-methoxycarbamoyl)imidazo[1,2-a]pyridine (584 mg, 1.97 mmol) and 1-bromo-4-fluorobenzene were converted to product in a manner substantially analogous to Example 141 to yield 205 mg. (52%). NMR (200 MHz, CDCl$_3$) d 4.31 (bs, 2H, NH), 7.15 (m, 2H, F—ArH ), 7.25–7.56 (m, 7H, ArH+H$_7$+H$_8$), 7.78 (m, 2H, F—ArH), 8.69 (s, H$_5$).

Example 144

2-Amino-3-phenyl-6-(2,3-difluorobenzoyl)-imidazo[1,2-a]pyridine

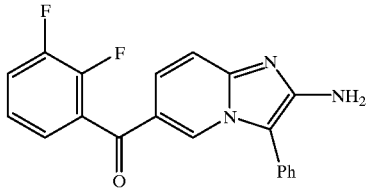

To a solution of 2,3-difluorobromobenzene (0.945 g, 8.44 mmol) in dry THF (20 mL), was added n-butyl lithium (1.6M in hexanes, 5.27 mL) at −78° C. The resulting yellow solution was stirred at the same temperature for 70 minutes, then a solution of 2-amino-3-phenyl-6-(N-methyl-N-methoxycarbamoyl)imidazo,2-a]pyridine (500 mg, 1.69 mmol) in dry THF (20 mL), under argon, was added dropwise via a cannula. The resulting orange solution was allowed to warm very slowly to RT during a 2.5 hour period. Saturated NH$_4$Cl was added, and the mixture was stirred for 25 minutes then extracted with EtOAc. The organic layer was washed with brine, and dried (Na$_2$SO$_4$). The solvents were evaporated and the residue was purified by column chromatography (CH$_2$Cl$_2$/CH$_3$CN, 4/1) to give 440 mg (74.7%) of product as a yellow solid. MS(FAB) m/z 350.1 (M$^+$+1,100.0 ), NMR (200 MHz, DMSO d6) d 5.71 (bs, 2H, NH), 7.27–7.70 (m, 11H, F—ArH+ArH+H$_7$+H8), 8.58 (dd, J$_{57}$=1.8, J$_{58}$=0.9, H$_5$).

Example 145

2-Amino-3-methylthio-6-(1-phenyl-2-cyanovinyl)-imidazo[1,2-a]pyridine

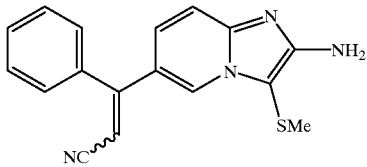

To a solution of 2-amino-3-methylthio-6-benzoyl-imidazo[1,2-a]pyridine (40 mg, 0.14 mmol) in 4 mL of dry THF was added diethyl phospononitrile (265 mg, 1.5 mmol) dropwise at −78° C. An orange solid formed. Two ml of THF was added and the reaction mixture was stirred for 2 hours at −78° C. The reaction mixture was allowed to warm to RT over 3 hours. The solution turned green. The mixture was hydrolized with a drop of H$_2$O, the solvent was removed in vacuo, and the residue was subjected to column chromatography (EtOAc) to yield 23 mg, (51%), of the E-isomer, $^1$H-NMR (200 MHz, CDCl$_3$) d 2.22 ( s, 3H, SMe, 4.43 (bs, 2H, NH2), 5.75 (s, 1H, Hvinilic), 7.04 (dd, 1H, J57=2.0, J78=9.1, H7), 7.32–7.50 (m, 6H, ArH+H8), 8.54 (dd, J58=0.9, J57=2.0, H5), and 14 mg, (32%) of the Z-isomer, $^1$H-NMR (200 MHz, CDCl$_3$) d 2.10 ( s, 3H, SMe, 4.40 (bs, 2H, NH2), 5.79 (s, 1H, Hvinilic), 7.13 (dd, 1H, J57=1.9, J78=9.2, H7), 7.32 (dd, J58=0.8, J78=9.2, H8),7.47–7.53 (m, 5H, ArH), 8.07 (dd, J58=0.8, J57=1.9, H5).

Example 146

2-Amino-3-methylsulfonyl-6-(1-phenyl-2-cyanovinyl)imidazo[1,2-a]pyridine

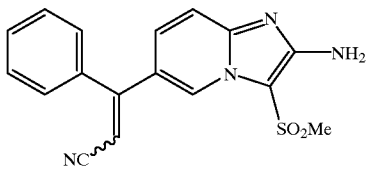

The 2-amino-6-benzoyl-3-(methylsulfonyl)imidazo[1,2-a]pyridine was converted to product in a manner substantially analogous to Example 145 to give the vinyl nitrile as a mixture of 2 isomers E:Z in 1:2 ratio and 77% global yield. The Z-isomer was isolated by column chromatography (isopropanol:EtOAc/3:7). 1H-NMR (200 MHz, CDCl$_3$) d 3.17 (s, 3H, SO2Me), 4.66 (bs, 2H, NH2), 5.77 (s, 1H, vinylic), 7.10 (dd, 1H, J57=1.8, J78=9.3, H7), 7.30–7.46 (m, 6H, ArH+H8), 8.82 (dd, J58=0.8, J57=1.8, H5).

Example 147

2-Amino-6-[(E)-1-phenyl-2-N-methylcarbamoylvinyl]-imidazo[1,2-a]pyridine

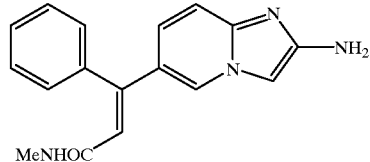

The 2-trifluoroacetamido-6-[(E)-1-phenyl-2-N-methylcarbamoylvinyl]-imidazo[1,2-a]pyridine (300 mg, 0.77 mmol) was stirred in the presence of 0.5 N NaOH (17 ml) at RT for 5 hours. The solution was neutralized to pH=7 with HCl (5% aqueous solution) and extracted with CHCl$_3$ (3×50 ml). The combined organic extracts were dried (Na$_2$SO$_4$) and the solvent was removed in vacuo to yield 130 mg (58%) of product as a light-brown solid. M.P. 97–99° C., NMR (CDCl$_3$) d 7.61 (d, 1H, J=1.4 Hz, H$_5$), 7.47–7.41 (m, 3H, Ar), 7.33–7.27 (m, 3H, Ar), 7.12 (dd, 1H, J=9.3, 1.8 Hz, H$_7$ o H$_8$), 6.77 (s, 1H, H$_3$), 6.36 (s, 1H, H vinyl), 5.13 (broad d, 1H, J=4.9 Hz, NHMe), 3.90 (broad s, 2H, NH$_2$), 2.62 (d, 3H, J=4.9 Hz, CH$_3$NH), EIMS m/z 292 M$^+$(100), 262(32), 234(20), 223(15), 215(13), 178(8), 160(10), 117(6), 105(9), 77(9).

Example 148

2-Amino-3-ispropylthio-6-[(E)-1-phenyl-2-N-methylcarbamoylvinyl]-imidazo[1,2-a]pyridine

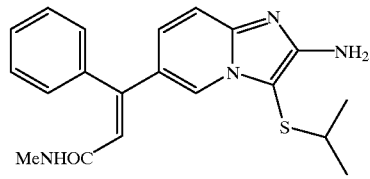

To a solution of 2-trifluoroacetamido-3-iodo-6-[(E)-1-phenyl-2-N-methylcarbamoylvinyl]-imidazo[1,2-a]pyridine (72 mg, 0.15 mmol) in 5 ml of THF cooled to −78° C. was added phenyl lithium (230 μl, 0.33 mmol) under an argon atmosphere. The reaction mixture was stirred for 3 minutes before injecting t-butyl lithium (310 μl, 0.38 mmol). After stirring for a 10 minute period, a solution of isopropyl isopropanethiol-sulfonate (109 mg, 0.600 mmol) in 5 ml of THF was added. The reaction mixture was stirred for 30 minutes at −78° C. and then quenched with 2 drops of H$_2$O and 10 ml THF. Ethyl acetate (15 ml) was added and the mixture was allowed to warm to RT. The solution was filtered through celite and the solvents were removed in vacuo. Radial chromatography affords the isopropyl sulfide with the trifluoroacetyl group cleaved and the intermediate in pure form. The ratio of intermediate/product depends on the speed of the radial chromatography. The trifluoroacetyl material was mixed with silicagel in MeOH/CH$_2$Cl$_2$ and the cake was stirred for 2 days. After filtration the product was obtained in 73% global yield. EIMS m/z 366 M$^+$(33), 323 (100), 293 (18), 237 (15), 196 (10), 178 (7), 102 (6), $^1$H-NMR (CDCl$_3$) d 8.01 (d, 1H, J=1.5 Hz, H$_5$), 7.47–7.20 (m, 7H, Ar), 6.40 (s, 1H, Hvinyl), 5.20 (broad s, 1H, J=4.9 Hz, NHMe), 4.26 (broad s, 2H, NH$_2$), 2.97 (hept, 1H, J=6.8

Hz, C$\underline{\text{H}}$(CH$_3$)$_2$), 2.65 (d, 3H, J=4.9 Hz, C$\underline{\text{H}}_3$NH), 1.13 (d, 6H, J=6.8 Hz, (C$\underline{\text{H}}_3$)$_2$CH).

Example 149

2-Amino-3-isopropylsulfonyl-6-[(E)-1-phenyl-2-N-methylcarbamoylvinyl]-imidazo[1,2-a]pyridine

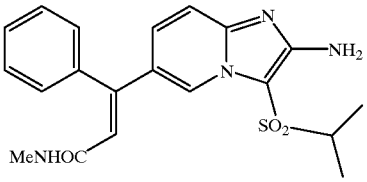

The 2-trifluoroacetamido-3-isopropylsulfonyl-6-[(E)-1-phenyl-2-N-methylcarbamoylvinyl]-imidazo[1,2-a]pyridine (45 mg, 0.09 mmol) was dissolved in a 1:1 mixture of MeOH:CH$_2$Cl$_2$ and silica gel was added until a cake is obtained. The cake was vigorously stirred for 2 days. After filtration through celite, the product is obtained as a white solid. (33 mg, 89%). EIMS m/z 398 M$^+$(44), 292 (100), 262 (27), 233 (15), 215 (9), 205 (8), 178 (7), 77 (6), 58 (8), NMR (CDCl$_3$) d 8.46 (s, 1H, H$_5$), 7.53–7.30 (m, 7H. Ar),. 6.41 (s, 1H, Hvinyl), 5.30 (d, 1H, J=4.8 Hz, N$\underline{\text{H}}$Me), 5.17 (broad s, 2H, NH2), 3.26 (hept, 1H, J=7.0 Hz, C$\underline{\text{H}}$(CH$_3$)$_2$), 2.12 (d, 3H, J=4.8 Hz, C$\underline{\text{H}}_3$NH), 1.34 (d, 6H, J=7.0 Hz, (CH$_3$)$_2$CH).

Example 150

2-Amino-3-phenyl-6-(1-(2,3-difluorophenyl)oxime)-imidazo[1,2-a]pyridine

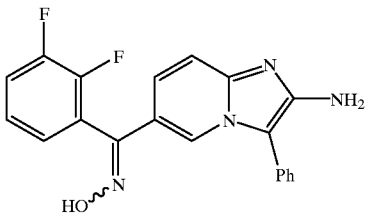

The 2-amino-3-phenyl-6-(2,3-difluorobenzoyl)-imidazo[1,2-a]pyridine (0.15 g, 0.43 mmol) was mixed with hydroxylamine hydrochloride (0.357 g, 5.16 mmol) and NaOAc (0.424 g, 5.16 mmol) in an 80%, solution of EtOH (9 mL). The reaction mixture was refluxed under argon for 20 hours. The solvents were removed in vacuo and the residue was taken up in EtOAc-H$_2$O. The organic layer was washed with saturated NaHCO3 (2×20 mL) and brine (2×25 mL) then dried (Na$_2$SO$_4$), and evaporated to give the product quantitavely as a yellow solid. The ratio E:Z determined by NMR was found to be (2/1). NMR (200 MHz, DMSO-d$_6$) d 5.34 (bs, NH$_2$ E), 5.38 (NH$_2$ Z), 8.04 (s, H$_5$ E), 8.91 (H$_5$ Z), 11.77 (s, OH E), 12.14 (s, OH Z).

Example 151

2-Amino-3-phenyl-6-(1-(2,3-difluorophenyl)-2-N-methylcarbamoylvinyl)-imidazo[1,2-a]pyridine

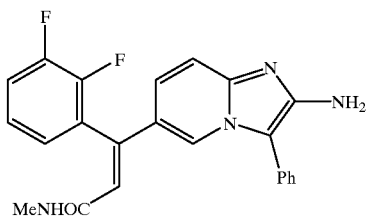

The 2-trifluoroacetamido-3-phenyl-6-[(E)-1-(2,3-difluorophenyl)-2-methylcarbamoylvinyl]-imidazo[1,2-a] pyridine (0.13 g, 0.26 mmol) was dissolved in MeOH/diisopropylethylamine (4 mL 1/1 v/v) and refluxed under argon for 4 days. The solvents were removed in vacuo and the mixture was purified by column chromatography (CH$_2$Cl$_2$/CH$_3$CN/MeOH 55/40/5) to recover 27 mg (32.5%) of product. $^1$H NMR (200 MHz, CDCl$_3$) d 3.86 (d, J=9.0, 3H, CONHCH$_3$), 4.15 (bs, 2H, NH), 6.64 (s, Hvinilic), 7.02–7.45 (m, 10H, F—ArH+ArH+H$_7$+H$_8$), 8.14 (d, J$_{57}$=1.5, H$_5$), $^{13}$C NMR (50 MHz, CDCl$_3$) d 33.7, 114.6, 118.0, 118.4, 121.0, 121.6, 122.4, 122.6, 123.2, 124.2, 127.7, 127.7, 128.9, 129.7, 147.0, 148.7, 161.9.

Example 152

2-Amino-3-phenyl-6-[(E)-1-phenyl-2-N-methylcarbamoylvinyl]-imidazo[1,2-a]pyridine

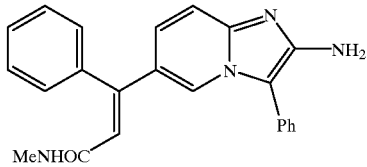

The 2-trifluoroacetamido-3-phenyl-6-[(E)-1-phenyl-2-N-methylcarbamoylvinyl]-imidazo[1,2-a]pyridine (190 mg, 0.420 mmol) was converted to product in a manner substantially analogous to Example 151 to give 127–135 mg. (85–90%). NMR (200 MHz, CD3OD) : d 2.60 (s, 3H NHCH3), 6.44 (s, 1H, H vinilic), 7.20–7.42 (m, 12H, ArH+H7+H8), 7.91 (bs, 1H, H5).

Example 153

2-Amino-3-(2,5-difluorophenyl)-6-[(E)-1-phenyl-2-N-methylcarbamoylvinyl]-imidazo[1,2-a]pyridine

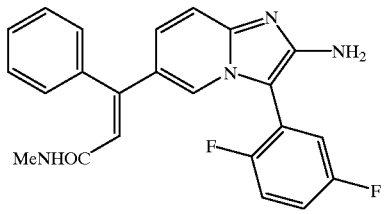

The 2-trifluoroacetamido-3-(2,5-difluorophenyl)-6-[(E)-1-phenyl-2-N-methylcarbamoylvinyl]-imidazo[1,2-a]

pyridine (333 mg, 0.682 mmol) was converted to product in a manner substantially analogous to Example 151 to give 227–241 mg. (85–90%). EIMS m/z 404 M⁺(100), 374(17), 345(12), 207(9), 152(7), 140(7), 105(7), 77(11), NMR (CDCl₃) d 7.62 (dd, 1H, J=2.1, 1.2 Hz, H₅), 7.45–6.99 (m, 10H, Ar). 6.35 (s, 1H, H vinyl), 5.19 (d, 1H, J=4.9 Hz, NH), 4.18 (broad s, 2H, NH₂), 2.63 (d, 3H, J=5.0 Hz, CH₃).

Example 154

2-Amino-3-(2-trifluoromethyl-4-fluorophenyl)-6-[(E)-1-phenyl-2-N-methylcarbamoylvinyl]-imidazo[1,2-a]pyridine

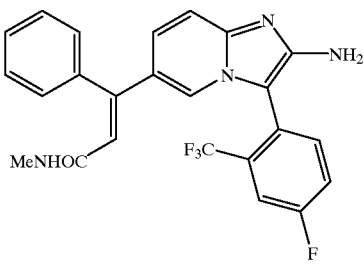

The 2-trifluoroacetamido-3-(2-trifluoromethyl-4-fluorophenyl)-6-[(E)-1-phenyl-2-N-methylcarbamoylvinyl]-imidazo[1,2-a]pyridine (310 mg, 0.576 mmol) was converted to product in a manner substantially analogous to Example 151 to give 216–229 mg. (85–90%). MS(FD) (EI⁺) m/z 454 M⁺(100), 424(19), 395 (12), 356(7), 279(10), 209(11), 77(9), NMR (CDCl₃) d 7.52 (dd, 1H, J=8.4 Hz, H₇ ó H₈), 7.47–7.16 (m, 9H, Ar), 6.94 (d, 1H, J=8.9 Hz, H₇ ó H₈), 6.16 (s, 1H, Hvinyl), 5.39 (broad d, 1H, J=4.6 Hz, NHMe), 3.92 (broad s, 2H, NH₂), 2.55 (d, 3H, J=4.7 Hz, CH₃).

Example 155

2-Amino-3-(2,3,4-trifluorophenyl)-6-[(E)-1-phenyl-2-N-methylcarbamoylvinyl]-imidazo[1,2-a]pyridine

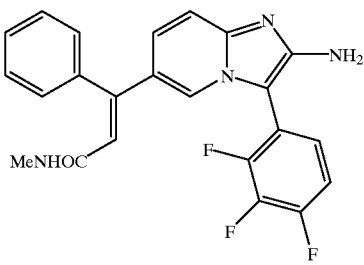

The 2-trifluoroacetamido-3-(2,3,4-trifluorophenyl)-6-[(E)-1-phenyl-2-N-methylcarbamoylvinyl]-imidazo[1,2-a] pyridine (134 mg, 0.265 mmol) was converted to product in a manner substantially analogous to Example 151 to give 92.3–97.7 mg. (85–90%). EIMS m/z 423 M⁺(6), 422 (25), 392 (6), 353 (14), 259 (14), 105 (16), 84 (100) NMR (CDCl₃) d 7.70 (s, 1H, C₇H₃N₂), 7.44–7.00 (m, 9H, Ar), 6.63 (s, 1H, CH=C), 5.20 (s broud, 1H, NH—CH₃) 4.13 (s broud, 2H, NH₂), 2.62 (d, J=4.9 Hz, 3H, NH—CH₃).

Example 156

2-Amino-3-(3,5-difluorophenyl)-6-(1-phenyl-2-N-methylcarbamoylvinyl)-imidazo[1,2-a]pyridine

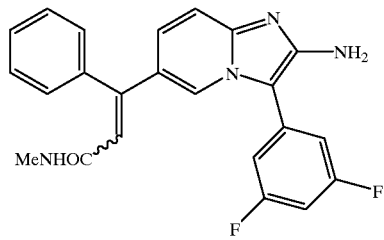

The 2-trifluoroacetamido-3-(3,5-difluorophenyl)-6-(1-phenyl-2-N-methylcarbamoylvinyl)-imidazo[1,2-a]pyridine (113 mg, 0.232 mmol) was converted to product in a manner substantially analogous to Example 151 to give 77.3–81.8. (85–90%). EIMS m/z 405 M⁺(34), 404 (100), 374 (22), 345 (17), 84 (14), NMR (CDCl₃) d 8.28 and 7.92 (s, 1H, C₇H₃N₂), 7.5–6.7 (m, 10H, Ar), 6.36 and 6.28 (s, 1H, CH=C), 5.71 y 5.24 (s broud, 1H, NH—CH₃) 4.22 (s broud, 2H, NH₂), 2.82 and 2.65 (d, J=4.9 and 4.9 Hz, 3H, NH—CH₃).

Example 157

2-Amino-3-(3-trifluoromethylphenyl)-6-[(E)-1-phenyl-2-N-methylcarbamoylvinyl]-imidazo[1,2-a]pyridine

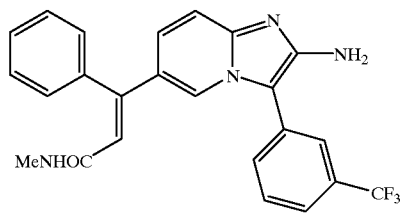

The 2-trifluoroacetamido-3-(3-trifluoromethylphenyl)-6-[(E)-1-phenyl-2-N-methylcarbamoylvinyl]-imidazo[1,2-a] pyridine (142 mg, 0.273 mmol) was converted to product in a manner substantially analogous to Example 151 to give 98.4–104 mg. (85–90%). EIMS m/z 437 M⁺(36), 436 (100), 406 (18), 377 (16), 279 (10), 77 (6), NMR (CDCl₃) d 7.83 (s, 1H, C₇H₃N₂), 7.64 (m, 11H, Ar), 6.42 and 6.38 (s, 1H, CH=C), 5.13 (s broud, 1H, NH—CH₃) 4.11 (s broud, 2H, NH₂), 2.62 (d, J=4.9 Hz, 3H, NH—CH₃)

Example 158

2-Amino-3-benzoyl-6-[(E)-1-phenyl-2-N-methylcarbamoylvinyl]-imidazo[1,2-a]pyridine

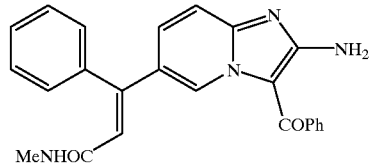

The 1-(2-oxo-2-phenylethyl)-2-chloro-5-[(E)-1-phenyl-2-methylcarbamoylvinyl]pyridinium iodide (0.250 g, 0.482 mmol) was mixed with aminonitrile (220 mg, 0.49 mmol) and $K_2CO_3$ (200 mg, 1.47 mmol) in 10 ml of $CH_3CN$. The reaction mixture was refluxed for 14 hours. After cooling to RT the mixture was filtered and the filter cake was washed with $CH_3CN$. The mother liquor was evaporated and the residue was purified by column chromatography (acetone/EtOAc 1:1) to give 62.8 mg of product as slightly colored solid in 39% yield. MS(HR), NMR.

Example 159

2-Amino-3-(4-fluorobenzoyl)-6-[(E)-1-phenyl-2-N-methylcarbamoylvinyl]-imidazo[1,2-a]pyridine

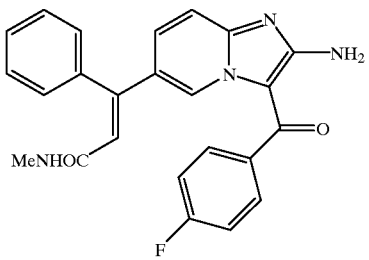

The 1-[2-oxo-2-(4-fluorophenyl)ethyl]-2-chloro-5-[(E)-1-phenyl-2-methylcarbamoylvinyl]pyridinium iodide (400 mg, 0.740 mmol) was converted to product in a manner substantially analogous to Example 158 to give 118 mg. (38%). IR (KBr) u (cm$^{-1}$) 3676, 3457, 3283, 3102, 1735, 1640, 1640, 1448, 1352, 1154, 849, 700, NMR (300 MHz, DMSO-d$_6$) d 8.56(s, 1H); 7.86(d,1H,J=5.12); 7.56–7.49(m, 2H); 7.36(d,1H,J=8.79); 7.3–7.2(m,5H); 7.15(m,2H); 6.44 (s,1H); 6(s,2H); 2.48(s,3E), MS(HR): calcd. for $C_{24}H_{19}N_4O_2$ 414.1492, found 414.1498.

Example 160

2-Amino-3-acetyl-6-[(E)-1-phenyl-2-N-methylcarbamoylvinyl]-imidazo[1,2-a]pyridine

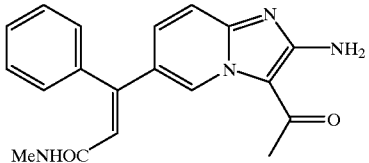

The 1-[2-oxopropyl]-2-chloro-5-[(E)-1-phenyl-2-methylcarbamoylvinyl]pyridinium iodide (400 mg, 0.870 mmol) was converted to product in a manner substantially analogous to Example 158 to give 118 mg. (40%). MS(HR): m/z calcd. for $C_{19}H_{18}N_4O_2$ 334.1430. found.334.1430, IR (KBr) u (cm$^{-1}$) 3440, 1614, 1530, 1458, 1348, 820.

Example 161

2-Amino-3-t-butylacetyl-6-[(E)-1-phenyl-2-N-methylcarbamoylvinyl]-imidazo[1-a]pyridine

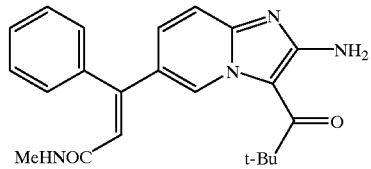

The 1-[2-oxo-3,3-dimethylbutyl]-2-chloro-5-[(E)-1-phenyl-2-methylcarbamoylvinyl]pyridinium iodide (140 mg, 0.280 mmol) was converted to product in a manner substantially analogous to Example 158 to give 31.9 mg. (30%). MS(HR): calcd. for $C_{22}H_{24}N_4O_2$ 376.1899 found 376.1900, NMR (300 MHz, DMSO-d$_6$) d 9.22(s,1H); 7.8 (d,1H,J=4.4); 7.4–7.3(m,4H); 7.18(d,1H,J=4); 7.16(d,1H, J=2.5); 6.43(s,1H); 6.35(sa,2H); 2.52(d,3H,J=4.4); 1.17(s, 9H).

Example 162

2-Amino-3-t-butylacetyl-6-[(E)-1-(2,3-difluorophenyl)-2-N-methylcarbamoylvinyl]-imidazo[1,2-a]pyridine

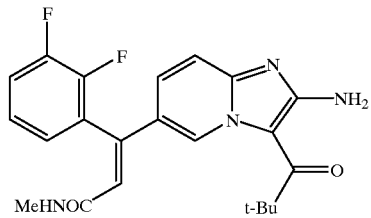

The 1-[2-oxo-3,3-dimethylbutyl]-2-chloro-5-[(E)-1-(2,3-diflurorphenyl)-2-methylcarbamoylvinyl]pyridinium iodide (120 mg, 0.220 mmol) was converted to product in a manner substantially analogous to Example 158 to give 11.2 mg. (12%). MS(HR): calcd. for $C_{22}H_{22}N_4O_2F_2$ 412.1711, found. 412.1713, NMR (300 MHz, CDCl$_3$) d 9.4(s,1H); 7.28(d,1H, J=1.1); 7.21–7.14(m,3H); 6.98(m, 1H);6.49(s,1H); 5.62(sa, 1H); 5.35(s,2H); 2.78((d,3H,J=4.76); 1.32(s,9H).

As described above, the compounds of the present invention are useful as antiviral agents. They show inhibitory activity against various strains of enterovirus and rhinovirus. An embodiment of the present invention is a method of treating or preventing picornaviridae infection comprising administering to a host in need thereof an effective amount of a compound of Formula (I) or a pharmaceutically acceptable salt thereof.

The term "effective amount" as used herein, means an amount of a compound of Formula (I) which is capable of inhibiting viral replication. The picornaviridae inhibition contemplated by the present method includes either therapeutic or prophylactic treatment, as appropriate. The specific dose of compound administered according to this invention to obtain therapeutic or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of Formula (I) or a pharmaceutically acceptable salt thereof and a pharmaceutically acceptable carrier, diluent or excipient thereof.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using well-known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation example is only illustrative and is not intended to limit the scope of the invention in any way.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Test Methods

African green monkey kidney cells (BSC-1) or Hela cells (5-3) were grown in 25 cc Falcon flasks at 37° C. in medium 199 with 5 percent inactivated fetal bovine serum (FBS), penicillin (150 units 1 ml) and streptomycin (150 micrograms per milliliter ($\mu$g/ml)). When confluent monolayers were formed, the supernatant growth medium was removed and 0.3 ml of an appropriate dilution of virus (e.g. echo, Mengo, Coxsackie, polio or rhinovirus) were added to each flask. After absorption for one hour at room temperature, the virus infected cell sheet was overlaid with a medium comprising one part of 1 percent Ionagar No. 2 and one part double strength medium 199 with FBS, penicillin and streptomycin which contains drug at concentrations of 100, 50, 25, 12, 6, 3 and 0 $\mu$g/ml. The flask containing no drug served as the control for the test. The stock solutions of compounds were diluted with dimethylsulfoxide to a concentration of $10^4$ $\mu$g/ml. The flasks were then incubated for 72 hours at 37° C. for polio, Coxsackie, echo and Mengo virus and 120 hours at 32° C. for rhinovirus. Virus plaques were seen in those areas were the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound can be expressed as percentage plaque reduction, or percent inhibition. Alternatively, the drug concentration which inhibits plague formation by 50 percent can be used as a measure of activity. The 50 percent inhibition value is denoted as the "$IC_{50}$". The compounds of the present invention displayed at least 30%, preferably 50% and most preferably over 85% inhibition of plaque formation at a single dose of 50 $\mu$mol. Dose response titrations on the compounds of the present invention reveal $IC_{50}$ values of <10 $\mu$M.

We claim:

1. A compound of the Formula (I):

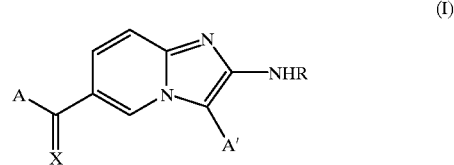

wherein:
A is phenyl, pyridyl, or benzyl;
wherein said phenyl or pyridyl groups may be optionally substituted with 1, 2, or 3 substituents independently selected from the group consisting of halo, $C_1$–$C_4$ alkyl, $C_1$–$C_6$ alkoxy, and trifluoromethyl;
R is hydrogen, $COR^4$, or $COCF_3$;
X is N—OH, O, or $CHR^1$;
$R^1$ is hydrogen, halo, CN, $C_1$–$C_4$ alkyl, —C≡CH, CO($C_1$–$C_4$ alkyl), $CO_2$($C_1$–$C_4$ alkyl), or $CONR^2R^3$;
$R^2$ and $R^3$ are independently hydrogen or $C_1$–$C_4$ alkyl;
A' is hydrogen, halo, $C_1$–$C_6$ alkyl, benzyl, naphthyl, thienyl, furyl, pyridyl, pyrrolyl, $COR^4$, $S(O)_nR^4$, or a group of the formula

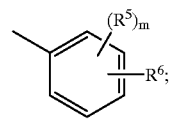

$R^4$ is $C_1$–$C_6$ alkyl, or phenyl;
wherein said phenyl may be optionally substituted with 1, 2, or 3 substituents independently selected from the group consisting of halo, $C_1$–$C_4$ alkyl, $C_1$–$C_6$ alkoxy, and trifluoromethyl;
n is 0, 1, or 2;
$R^5$ is independently at each occurrence hydrogen or halo;

m is 1, 2, 3, or 4; and $R^6$ is hydrogen, halo, $CF_3$, OH, $CO_2H$, $NH_2$, $NO_2$, $CONHOCH_3$, $C_1$–$C_4$ alkyl, or $CO_2(C_1$–$C_4$ alkyl), $C_1$–$C_4$ alkoxy;

with the proviso that when A is unsubstituted phenyl, X is O, A' is hydrogen, and R is $COR^4$, then $R^4$ is not $C_1$–$C_6$ alkyl;

or a pharmaceutically acceptable salt thereof.

2. A compound of claim 1 wherein R is hydrogen.

3. A compound of claim 2 wherein:

A is phenyl;
   wherein said phenyl may be optionally substituted with 1, 2, or 3 substituents independently selected from the group consisting of halo, $C_1$–$C_4$ alkyl, $C_1$–$C_6$ alkoxy, and trifluoromethyl;

A' is $C_1$–$C_6$ alkyl $COR^4$, $S(O)_nR^4$, or a group of the formula

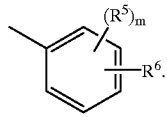

4. A compound o claim 1 wherein X is NOH or $CHR^1$.

5. A compound of claim 3 wherein X is NOH or $CHR^1$.

6. A compound of claim 5 wherein:

X is $CHR^1$;

$R^1$ is CN, $CO(C_1$–$C_4$ alkyl), or $CONR^2R^3$;

A is flourophenyl or diflourophenyl;

A' is a group of the formula

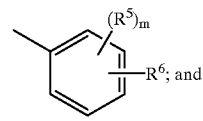

$R^5$ is halo.

7. A method for inhibiting the growth of a picornavirus comprising administering to a host in need thereof, an effective amount of a compound of any of claims 1 through 6.

8. A pharmaceutical formulation comprising as an active ingredient a compound of any of claims 1 through 6, associated with one or more pharmaceutically acceptable carriers, excipients or diluents.

* * * * *